US010420708B2

(12) United States Patent
Arric et al.

(10) Patent No.: US 10,420,708 B2
(45) Date of Patent: Sep. 24, 2019

(54) SYSTEMS AND METHODS FOR MEDICATION MANAGEMENT

(71) Applicant: Arrix, Inc., Irvine, CA (US)

(72) Inventors: James Arric, Irvine, CA (US); Akira Mu, Irvine, CA (US)

( * ) Notice: Subject to any disclaimer, the term of this patent is extended or adjusted under 35 U.S.C. 154(b) by 0 days.

(21) Appl. No.: 16/366,199

(22) Filed: Mar. 27, 2019

(65) Prior Publication Data
US 2019/0240114 A1  Aug. 8, 2019

Related U.S. Application Data

(63) Continuation-in-part of application No. 15/961,805, filed on Apr. 24, 2018.

(51) Int. Cl.
  *A61J 7/04*  (2006.01)
  *A61J 7/00*  (2006.01)
  *B65D 25/04*  (2006.01)

(52) U.S. Cl.
  CPC .......... *A61J 7/0454* (2015.05); *A61J 7/0084* (2013.01); *B65D 25/04* (2013.01)

(58) Field of Classification Search
  CPC .......... B65D 1/04; B65D 25/04; A61J 7/0084; A61J 7/0436; A61J 7/0454
  USPC ................................................ 700/231–244
  See application file for complete search history.

(56) References Cited

U.S. PATENT DOCUMENTS

| 4,288,006 | A  | * | 9/1981  | Clover, Jr. | ........... | B65D 47/265 206/534 |
| 8,152,020 | B2 | * | 4/2012  | Flowers     | ............ | G07F 17/0092 221/2 |
| 9,775,780 | B2 | * | 10/2017 | Afsarifard  | ............ | A61J 7/0418 |
| 2006/0071011 | A1 | * | 4/2006 | Varvarelis | ............ | A61J 7/0481 221/9 |
| 2015/0008152 | A1 | * | 1/2015 | Xu | .......................... | A61J 1/03 206/538 |
| 2018/0263854 | A1 | * | 9/2018 | Taylor | .................. | A61J 7/0436 |

* cited by examiner

*Primary Examiner* — Timothy R Waggoner
(74) *Attorney, Agent, or Firm* — CIONCA IP Law P.C.; Marin Cionca

(57) ABSTRACT

A medication management system, having a means for recording a medication regimen; and a medication dispenser having: a base having a sensor for detecting changes in the medication dispenser; a casing having: compartments; walls separating each compartment; and wires housed within the walls; a cap adapted to fit onto and rotate on the top end, the cap having: a door adapted to be in a closed state and in an open state; a first cap magnet; and a second cap magnet adapted to be aligned with and make a magnetic connection with the first cap magnet when the door is in the open state, creating a first electrical signal; wherein the first electrical signal is sent to the processor via the wires; such that a removal of the medication from the medication dispenser is detected by the sensor and generates a second electrical signal sent to the processor.

20 Claims, 49 Drawing Sheets

FIG. 12C

BENEFITS/USES

Atorvastatin is used along with a proper diet to help lower "bad" cholesterol and fats (such as LDL, triglycerides) and raise "good" cholesterol (HDL) in the blood. It belongs to a group of drugs known as "statins." It works by reducing the amount of cholesterol made by the liver. Lowering "bad" cholesterol and triglycerides and raising "good" cholesterol decreases the risk of heart disease and helps prevent strokes and heart attacks.

SIDE EFFECTS

- Muscle pain and damage
- Liver damage
- Increased blood sugar or type 2 diabetes
- Neurological side effects

RESOURCES

 Lipitor Info.pdf

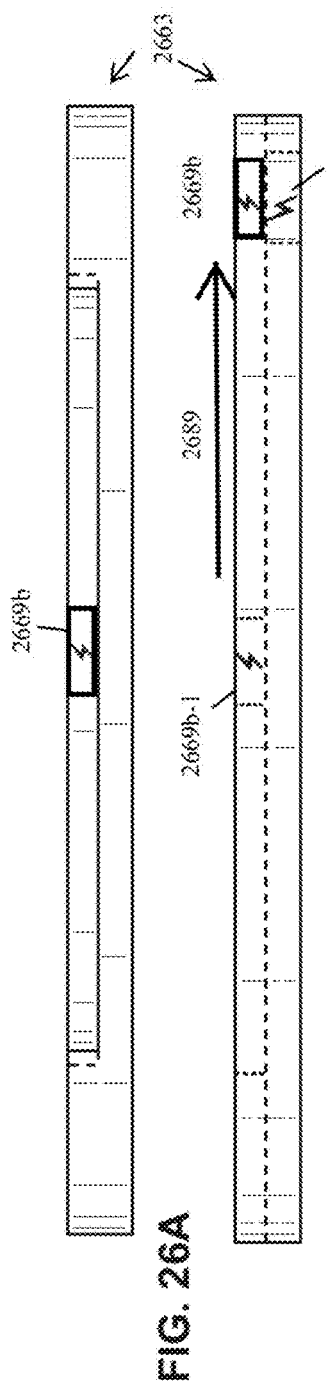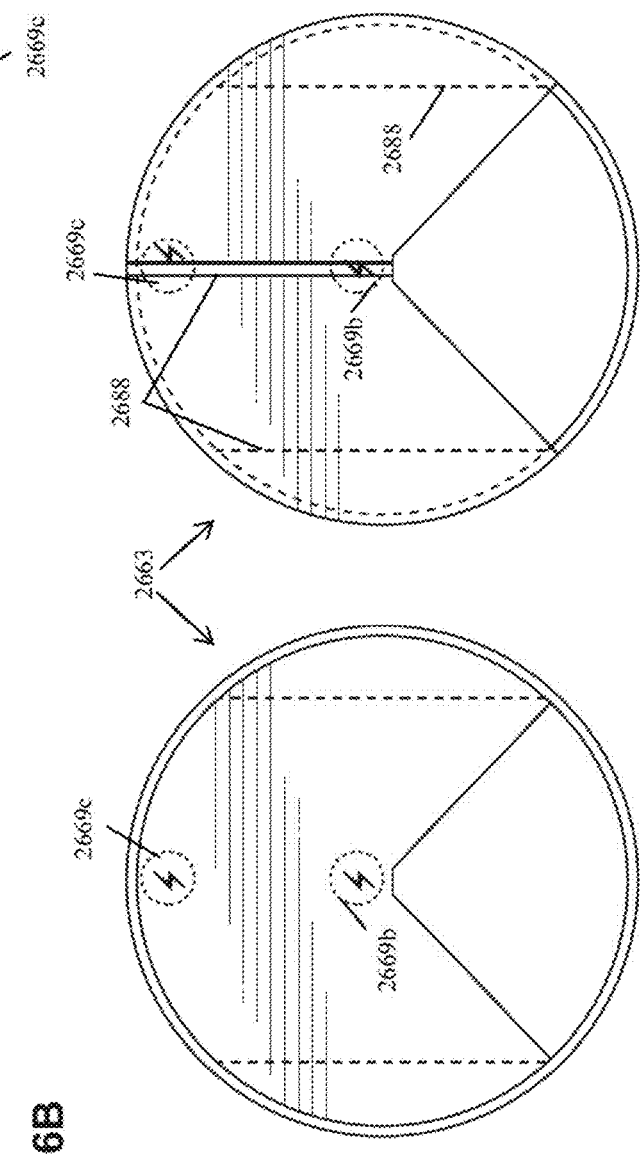
FIG. 26A
FIG. 26B
FIG. 26C
FIG. 26D

SYSTEMS AND METHODS FOR MEDICATION MANAGEMENT

CROSS-REFERENCE TO RELATED APPLICATIONS

This application is a continuation-in-part of and claims the benefit of U.S. Non-Provisional application Ser. No. 15/961,805, filed Apr. 24, 2018, which is hereby incorporated by reference, to the extent that it is not conflicting with the present application.

BACKGROUND OF INVENTION

1. Field of the Invention

The invention relates generally to medication and more specifically to medication dispensing and tracking.

2. Description of the Related Art

In recent years, chronic disease has been on the rise. Due to this, adults, particularly adults over 50, may have to take medication daily. As an example, many people need to take up to four medications on a daily basis. Thus, there is a potential for adverse drug reactions (or adverse drug effects), which can be caused by improper use of medication, allergic reactions, and under-doses and overdoses, to become more prevalent. Adverse drug reactions can be caused by a number of reasons, such as by many different medications having a similar appearance and causing confusion to a user. Another problem that is associated with prescription medication is that typically, manual entry of information is needed to capture medication, provider, patient, and pharmacy information when generating a prescription. This can be a multi-step process which can be time-consuming or inefficient. Another problem that may be associated with prescription medication is that doctors, when performing medication reconciliation, may be only able to rely on word of mouth from a patient, which may be unreliable or inaccurate.

Therefore, there is a need for a solution to these problems.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, a system and method are provided for medication management wherein a medication management platform is accessed through a mobile device application, and is in communication with a medication dispenser, wherein the medication dispenser is compact and transported by the user such that the user can access their medication at any time, wherein a plurality of different types of medications can be separately stored in and dispensed from the medication dispenser, and wherein the dispensing of medication from the dispenser is tracked and recorded by the medication management platform, and wherein the medication dispenser displays an alert to the user when medication consumption is needed according to a medication regimen associated with the user. Thus, an advantage is that medication regimens may be safer and more reliable, and more efficient for a user, and the user is not required to remember or memorize their prescription schedules or dosages, or any other similar information, particularly when a user must adhere to more than one prescription or medication regimen. Another advantage is that a user is alerted or prompted to take their medication, and may reduce the risk of missed dosages. Another advantage is that prescriptions may be created or changed more easily and efficiently by a doctor. Another advantage is that the platform may allow a user, doctor, pharmacist, or any other individual to easily, efficiently, and quickly scan and import data such as medication, provider, patient, and pharmacy information. Another advantage is that multiple types of medication may be carried, stored, and dispensed from a single medication dispenser, which may streamline the process of medication adherence for a user. Another advantage is that the taking of medication may be tracked by the medication dispenser via internet connectivity between the medication dispenser and the medication management platform. Another advantage may be that a user may customize their medication dispenser according to the number of different types of medications they need.

In another aspect, a medication management system is provided, comprising a means for recording a medication regimen; and a medication dispenser capable of separately holding and dispensing medication comprising a first medication and a second medication, the medication dispenser having: a dispenser bottom end; a dispenser top end; a base having: a processor; a control panel comprising buttons; a screen; a sensor adapted to detect changes in the medication dispenser; and a plurality of light sets; a casing having: an open top casing end; a bottom casing end adapted to be removably associated with the base; a plurality of compartments for storing the medication; a plurality of walls separating each compartment of the plurality of compartments, the plurality of walls extending between the open top casing end and the bottom casing end; and wires housed within the plurality of walls; wherein each compartment of the plurality of compartments has a shape and a set of dimensions at the open top casing end; wherein a first compartment of the plurality of compartments is adapted to hold and dispense the first medication; and wherein a second compartment of the plurality of compartments is adapted to hold and dispense the second medication; a cap adapted to be removably associated with the open top casing end, the cap having: a door adapted to slide between a closed state and an open state; a slider at the dispenser top end capable of sliding the door between the closed state and the open state; a first cap magnet; and a second cap magnet adapted to be aligned with and make a magnetic connection with the first cap magnet when the door is in the open state, the magnetic connection creating a first electrical signal; herein the cap is adapted to fit onto and rotate on the open top casing end; wherein the door has the shape and the set of dimensions such that the door is capable of being aligned with a compartment of the plurality of compartments via a rotation of the cap, such that the compartment of the plurality of compartments is accessible when the door is in the open state and the remaining compartments of the plurality of compartments is not accessible; wherein the first electrical signal generated within the cap is sent to the processor via the wires; wherein a first light set of the plurality of light sets corresponds to the first compartment of the plurality of compartments; wherein a second light set of the plurality of light sets correspond to the second compartment of the plurality of compartments; wherein the medication management system is adapted to send a first alert to the medication dispenser via the first light set when a user is scheduled within the medication regimen to take the first medication; wherein the medication management system is adapted to send a second alert to the medication dispenser via the second light set when the user is scheduled within the medication regimen to take the second medication; such that a removal of the first medication or the second medication from the medication dispenser is detected by the sensor and generates a second electrical signal; and wherein the second electrical signal is sent to the processor. Thus, again, an advantage is that medication regimens may be safer and more reliable, and more efficient for a user, and the user is not required to remember or memorize their prescription schedules or dosages, or any other similar information, particularly when a user must adhere to more than one prescription or medication regimen. Another advantage is that a user is alerted or prompted to take their medication, and may reduce the risk of missed dosages. Another advantage is that prescriptions may be created or changed more easily and efficiently by a doctor. Another advantage is that the OCR may allow a user, doctor, pharmacist, or any other individual to easily, efficiently, and quickly scan and import data such as medication, provider, patient, and pharmacy information. Another advantage is that multiple types of medication may be carried, stored, and dispensed from a single medication dispenser, which may streamline the process of medication adherence for a user. Another advantage is that the taking of medication may be tracked by the medication dispenser via internet connectivity between the medication dispenser and the medication management platform. Another advantage may be that a user may customize their medication dispenser according to the number of different types of medications they need.

In another aspect, a medication management system is provided, comprising a means for recording a medication regimen; and a medication dispenser capable of holding and dispensing medication, the medication dispenser having: a dispenser bottom end; a dispenser top end; a base having: a processor; a control panel; a screen; and a sensor adapted to detect changes in the medication dispenser; a casing having: an open top casing end; a bottom casing end adapted to be removably associated with the base; a plurality of compartments for storing the medication; a plurality of walls separating each compartment of the plurality of compartments, the plurality of walls extending between the open top casing end and the bottom casing end; and wires housed within the plurality of walls; wherein each compartment of the plurality of compartments has a shape and a set of dimensions at the open top casing end; a cap having: a door adapted to be in a closed state and in an open state; a first cap magnet; and a second cap magnet adapted to be aligned with and make a magnetic connection with the first cap magnet when the door is in the open state, the magnetic connection creating a first electrical signal; wherein the cap is adapted to fit onto and rotate on the open casing end; wherein the door has the shape and the set of dimensions such that the door is capable of being aligned with a compartment of the plurality of compartments via a rotation of the cap, such that the compartment of the plurality of compartments is accessible when the door is in the open state and the remaining compartments of the plurality of compartments is not accessible; wherein the first electrical signal generated within the cap is sent to the processor via the wires; such that a removal of the medication from the medication dispenser is detected by the sensor and generates a second electrical signal; and wherein the second electrical signal is sent to the processor. Thus, again, an advantage is that medication regimens may be safer and more reliable, and more efficient for a user, and the user is not required to remember or memorize their prescription schedules or dosages, or any other similar information, particularly when a user must adhere to more than one prescription or medication regimen. Another advantage is that a user is alerted or prompted to take their medication, and may reduce the risk of missed dosages. Another advantage is that prescriptions may be created or changed more easily and efficiently by a doctor. Another advantage is that the platform may allow a user, doctor, pharmacist, or any other individual to easily, efficiently, and quickly scan and import data such as medication, provider, patient, and pharmacy information. Another advantage is that multiple types of medication may be carried, stored, and dispensed from a single medication dispenser, which may streamline the process of medication adherence for a user. Another advantage is that the taking of medication may be tracked by the medication dispenser via internet connectivity between the medication dispenser and the medication management platform. Another advantage may be that a user may customize their medication dispenser according to the number of different types of medications they need.

In another aspect, a method of medication management using: a means for recording a medication regimen; a medication management platform accessible through an electronic device; and a medication dispenser capable of holding and dispensing medication is provided, the medication dispenser having: a dispenser bottom end; a dispenser top end; a base having: a processor; a control panel; a screen; and a sensor adapted to detect changes in the medication dispenser; a casing having: an open top casing end; a bottom casing end adapted to be removably associated with the base; a plurality of compartments for storing the medication; a plurality of walls separating each compartment of the plurality of compartments, the plurality of walls extending between the open top casing end and the bottom casing end; and wires housed within the plurality of walls; wherein each compartment of the plurality of compartments has a shape and a set of dimensions at the open top casing end; a cap having: a door adapted to be in a closed state and in an open state; a first cap magnet; and a second cap magnet adapted to be aligned with and make a magnetic connection with the first cap magnet when the door is in the open state, the magnetic connection creating a first electrical signal; wherein the cap is adapted to fit onto and rotate on the open casing end; wherein the door has the shape and the set of dimensions such that the door is capable of being aligned with a compartment of the plurality of compartments via a rotation of the cap, such that the compartment of the plurality of compartments is accessible when the door is in the open state and the remaining compartments of the plurality of compartments is not accessible; wherein the first electrical signal generated within the cap is sent to the processor via the wires; wherein the medication management system is adapted to send an alert to the medication dispenser when a user is scheduled within the medication regimen to take the medication; such that a removal of the medication from the medication dispenser is detected by the sensor and generates a second electrical signal; and wherein the second electrical signal is sent to the processor; the method comprising the steps of: receiving a set of instructions related to the medication regimen; accessing the medication management platform through the electronic device; importing the medication regimen into a user record stored within a medication management platform database, via the means for recording a medication regimen; sending the medication regimen to the medication dispenser; selection of a first compartment of the plurality of compartments; filling the first compartment of the plurality of compartments with the medication; notifying the user with the alert when the user is scheduled within the medication regimen to take the medication; and responding to the alert by dispensing the medication from the medication dispenser. Thus, again, an advantage is that medication regimens may be safer and more reliable, and more efficient for a user, and the user is not required to remember or memorize their prescription schedules or dosages, or any other similar information, particularly when a user must adhere to more than one prescription or medication regimen. Another advantage is that a user is alerted or prompted to take their medication, and may reduce the risk of missed dosages. Another advantage is that prescriptions may be created or changed more easily and efficiently by a doctor. Another advantage is that the OCR may allow a user, doctor, pharmacist, or any other individual to easily, efficiently, and quickly scan and import data such as medication, provider, patient, and pharmacy information. Another advantage is that multiple types of medication may be carried, stored, and dispensed from a single medication dispenser, which may streamline the process of medication adherence for a user. Another advantage is that the taking of medication may be tracked by the medication dispenser via internet connectivity between the medication dispenser and the medication management platform. Another advantage may be that a user may customize their medication dispenser according to the number of different types of medications they need.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which:

FIGS. 12A-12C show examples of user interfaces that may be accessed by a user when selecting a medication or prescription to view more information about the medication, according to an aspect.

FIG. 14 shows an example of a user interface of a physician's portal of the medication management platform displaying a list of patients under a user's care, according to an aspect.

FIGS. 15A-15B show examples of user interfaces of a physician's portal of the medication management platform showing a detailed view of an individual patient under the user's care, according to an aspect.

FIGS. 26A-26D illustrate the front elevation view, the right side elevation view, the bottom plan view, and the top plan view, respectively, of the sliding door cap 2663, shown without a slider for visual clarity, according to an aspect.

DETAILED DESCRIPTION

Figure 1A:
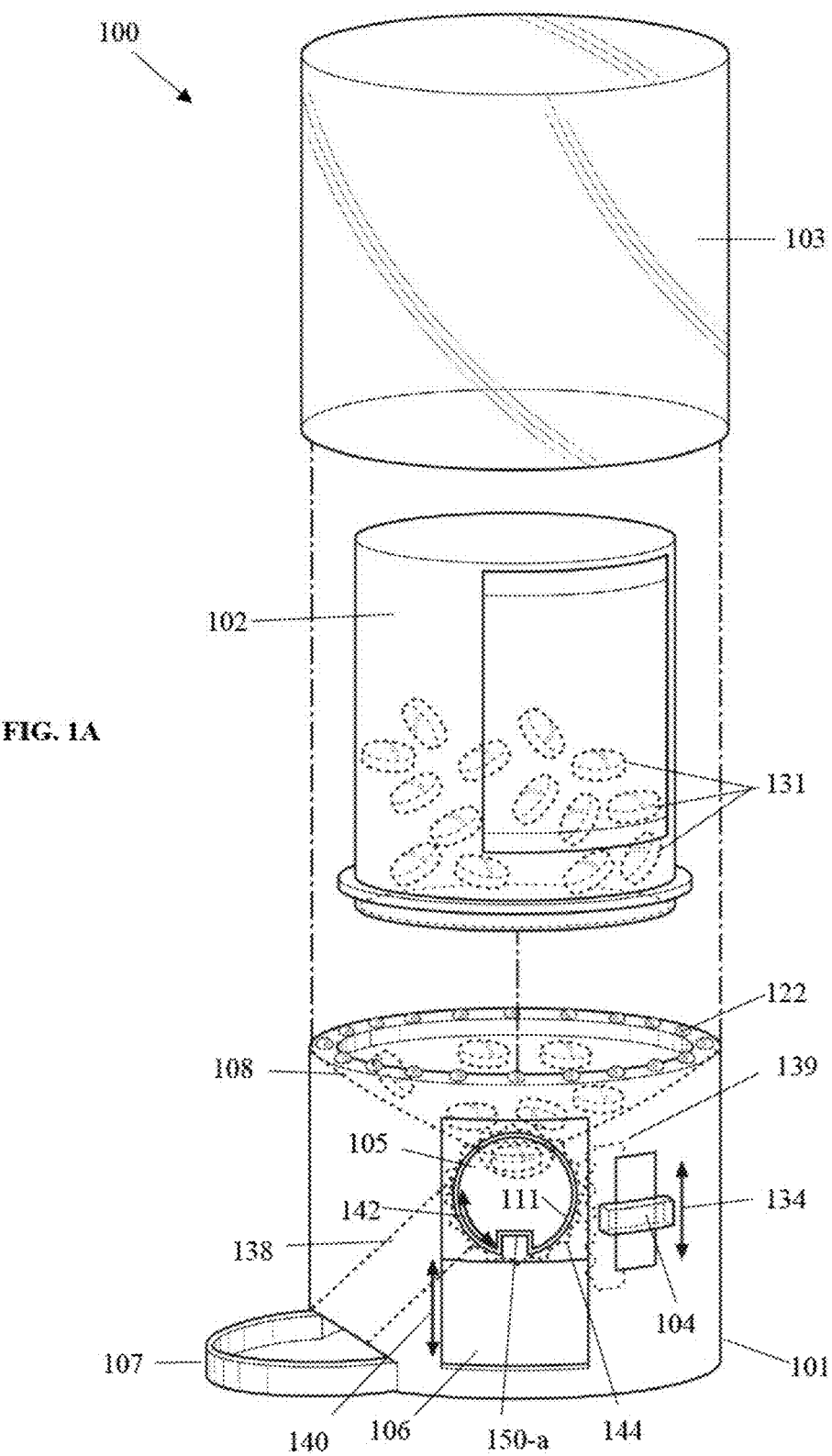
FIGS. 1A-1B illustrate the exploded right side view and the exploded left side view, respectively, of a compact medication dispensing apparatus, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

As used herein and throughout this disclosure, the term "mobile device" refers to any electronic device capable of communicating across a mobile network. A mobile device may have a processor, a memory, a transceiver, an input, and an output. Examples of such devices include cellular telephones, personal digital assistants (PDAs), portable computers, etc. The memory stores applications, software, or logic. Examples of processors are computer processors (processing units), microprocessors, digital signal processors, controllers and microcontrollers, etc. Examples of device memories that may comprise logic include RAM (random access memory), flash memories, ROMS (read-only memories), EPROMS (erasable programmable read-only memories), and EEPROMS (electrically erasable programmable read-only memories). A transceiver includes but is not limited to cellular, GPRS, Bluetooth, and Wi-Fi transceivers.

"Logic" as used herein and throughout this disclosure, refers to any information having the form of instruction signals and/or data that may be applied to direct the operation of a processor. Logic may be formed from signals stored in a device memory. Software is one example of such logic. Logic may also be comprised by digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network.

Mobile devices communicate with each other and with other elements via a network, for instance, a cellular network. A "network" can include broadband wide-area networks, local-area networks, and personal area networks. Communication across a network can be packet-based or use radio and frequency/amplitude modulations using appropriate analog-digital-analog converters and other elements. Examples of radio networks include GSM, CDMA, Wi-Fi and BLUETOOTH® networks, with communication being enabled by transceivers. A network typically includes a plurality of elements such as servers that host logic for performing tasks on the network. Servers may be placed at several logical points on the network. Servers may further be in communication with databases and can enable communication devices to access the contents of a database. For instance, an authentication server hosts or is in communication with a database having authentication information for users of a mobile network. A "user account" may include several attributes for a particular user, including a unique identifier of the mobile device(s) owned by the user, relationships with other users, call data records, bank account information, etc. A billing server may host a user account for the user to which value is added or removed based on the user's usage of services. One of these services includes mobile payment. In exemplary mobile payment systems, a user account hosted at a billing server is debited or credited based upon transactions performed by a user using their mobile device as a payment method.

For the following description, it can be assumed that most correspondingly labeled elements across the figures (e.g., 111 and 211, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

Figure 1B:
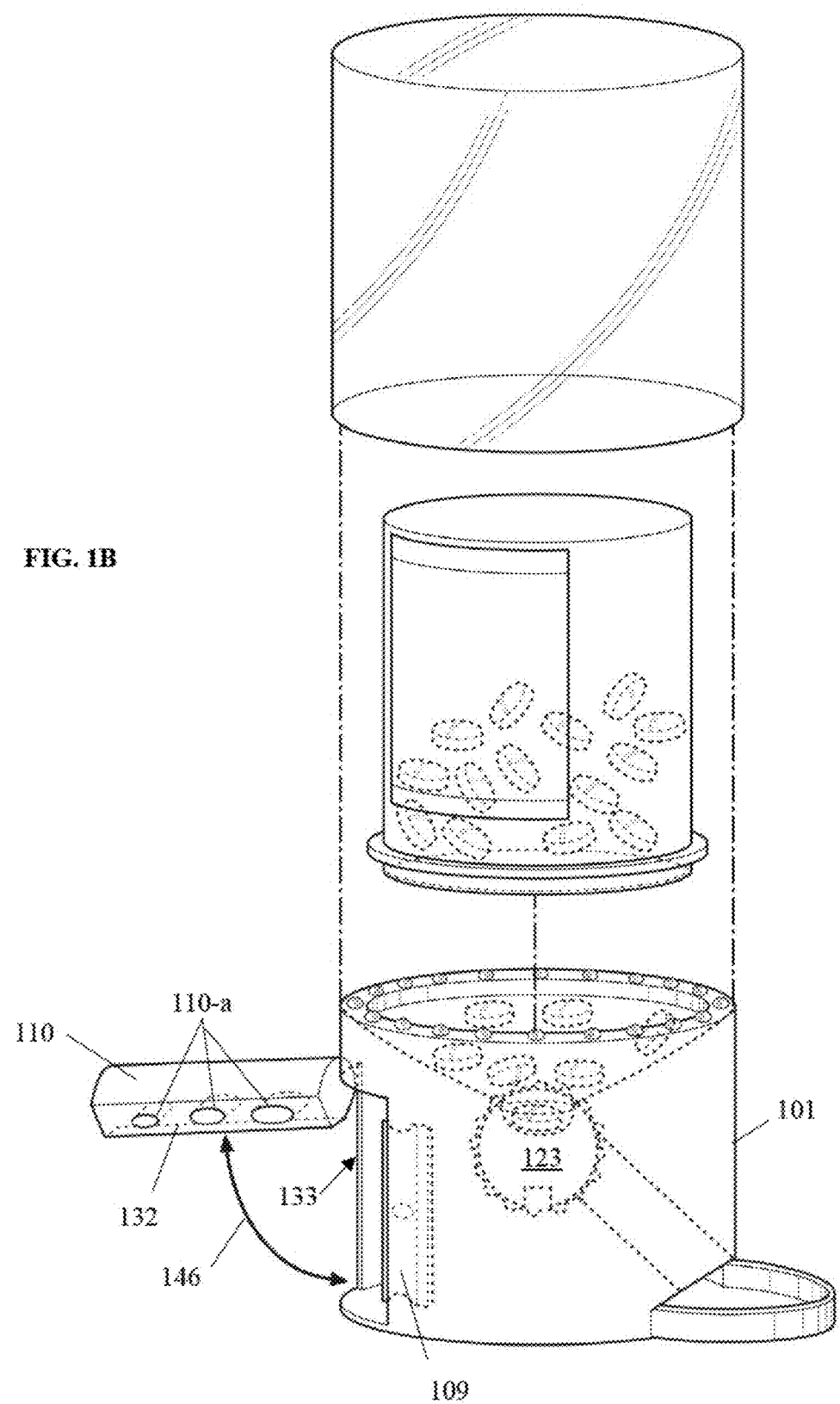

FIGS. 1A-1B illustrate the exploded right side view and the exploded left side view, respectively, of a compact medication dispensing apparatus ("medication dispensing apparatus," "compact dispenser," "compact medication dispenser" "medication delivery apparatus," "medication dispenser," "dispensing apparatus," or "apparatus") 100, according to an aspect. An exemplary medication bottle 102 is also shown in these views. As an example, a medication dispenser may be provided in a travel-sized, miniature, or compact configuration as shown in FIGS. 1A-1B, or may be provided in a tabletop configuration, as will be discussed further when referring to FIGS. 7A-7C. The compact dispenser 100 may be provided with a base 101, onto which the medication bottle ("medication bottle," "medicine bottle," or "bottle") 102 may be secured, and next covered by a glass casing 103. The glass casing 103 may, for example, be magnifying, and provide 3× magnification, and may provide 360 degrees of magnification around the bottle 102 such that the prescription labels can be easily read by the user.

Figure 2A:
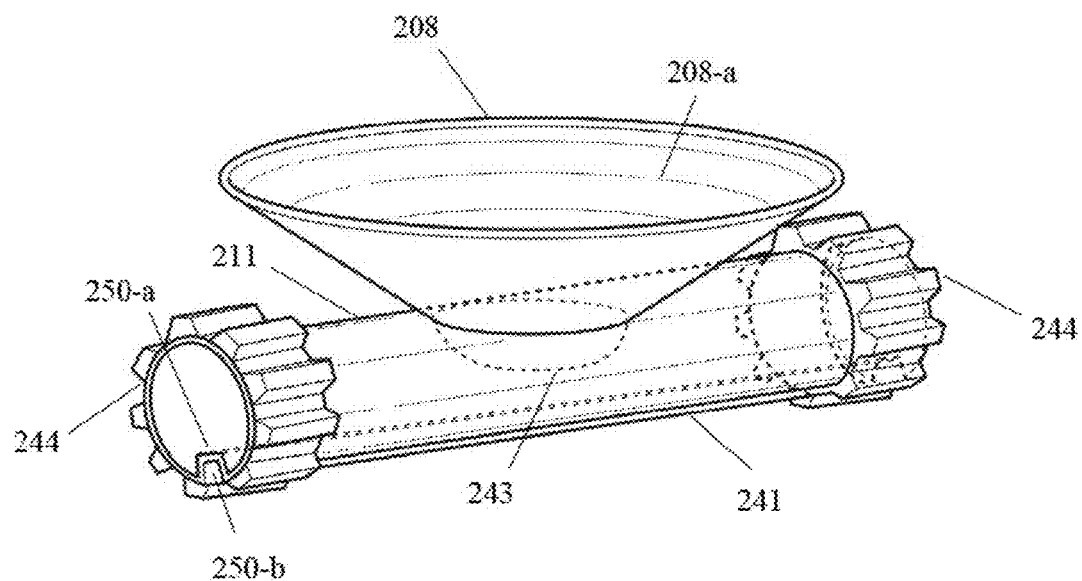
FIGS. 2A-2B illustrate the side perspective view and the top plan view of the funnel, the pill tube, and the pill tube of a medication dispensing apparatus, according to an aspect.
Figure 2B:
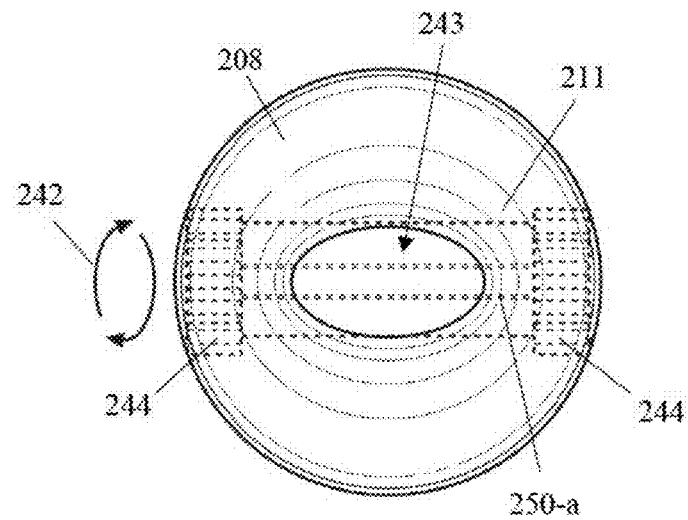

The compact dispenser 100 may be provided with a pill dispensing system ("pill dispensing system" or "medication dispensing system"), having a funnel 108, a pill tube and pill tube holder (as will be further discussed when referring to FIGS. 2A-2B), and a rack and pinion system wherein the rack is a gear arm 139, and the pinion is a gear (as shown by 244 in FIGS. 2A-2B). The pill dispensing system may also be provided with a gear actuator. The gear actuator may, for example, be a dispensing lever ("dispensing lever," or "lever") 104. The bottle 102 may be secured to the funnel 108 of the pill dispensing system within the compact dispenser 100. The bottle 102 may attach securely to the base 101 securely with childproofing means, such as, for example, with a mechanism requiring a push-down action for removing or securing the bottle 102. The removal of the bottle 102 may thus requiring pushing down and twisting simultaneously.

When a user receives medication and wishes to use the medication with the medication dispenser, first, the user may import the medication information into the medication management platform by any suitable means. For example, the user may manually enter the information, download the information, or scan the prescription label such that the label can be read by optical character recognition (OCR) technology. After the import is completed, the medication management system may, based upon the size and shape of the medication being used, recommend one pill tube ("pill tube" or "tube") 111 of a plurality of pill tubes provided with the pill dispensing system, to be secured to the pill dispensing system. Each pill tube 111 may include a pill tube hole sized to match a particular type of pill. The base 101 may be provided with a tube receiving slot ("receiving slot or "tube receiving slot") 105 on a first side of the surface of the base, and the receiving slot may be used for receiving the pill tube 111 into the base. The base 101 may be configured to securely hold the pill tube 111 by providing a sliding door 106 on the first side of the surface of the base, and by being closed on an opposite second side of the surface of the base. As an example, the base may also be provided with rubber grip feet (not shown).

The user may then begin use of the medication with the medication dispenser, such as the compact dispenser 100 as shown, and insert the selected pill tube 111 into the medication dispenser 100 by carrying out the following exemplary process. First, the user unscrews a cap provided with the medication bottle 102, and secures the bottle 102 onto the funnel 108 by turning the medication dispenser 100 upside-down onto the mouth of the bottle 102. Next, the sliding door 106 is opened by unlocking the door 106 through, for example a pushing action, which may unlatch the door, and sliding the door in a direction. The sliding door may be movable in the directions indicated by arrow 140, for example. The follow actions may be performed with the medication dispenser 100 upside-down such that the pills or medication 131 from the bottle 102 are not released out of the bottle. Next, the pill tube 111 is inserted into the receiving slot 105 by aligning the groove 150-a of the pill tube 111 with the fin of the tube holder (shown in FIG. 2A). Next, the pill tube is pushed as far back as possible by the user pushing on a first end of the tube, until the tube reaches the opposite side of the base 101, where a second end of the pill tube 111 is in contact with a release button 123. Next, the pill tube 111 is securely held within the housing by closing the sliding door 106 on the first end of the tube 111 by moving the sliding door 106 upwards, while the second end is resting against the release button 123 on the side of the base 101 opposite of the sliding door 106. The sliding door 106 may be held in place by, for example, a latch or any other suitable means of holding the door in place. The sliding door 106 may closed off the opening of the receiving slot 105, and the pill tube 111 may be held against the wall of the base 101 having the release button 123 on the opposite side, thus preventing the pill tube 111 from being released or falling out of the medication dispenser 100. The medication dispenser 100 may then be turned right-side-up for use, and a pill 131 may release from the bottle 102 through the funnel 108 and into the pill tube 108.

Next, when the medication 131 is needed by the user, the user operates the dispenser 100 by actuating a lever 104 in a direction indicated by arrow 134. The movement of the lever 104 may cause a movement of a rack or gear arm 139, which may actuate the rotational movement of a pinion or gear 144. The rotational movement of the gear 144 may then next cause the pill tube, which may be associated with the gear 144, to also rotate, such as in the directions indicated by arrows 142. Next, the rotational movement of the pill tube 111 may cause a hole in the pill tube (as will be further discussed when referring to FIGS. 2A-2B) to face downwards and release the pill within the tube into an exit tube 138 and cause the pill to fall into a pill catcher 107 such that the pill 131 is accessible by the user.

The lever 104 or any other suitable means for actuating the pill dispensing system may be provided with safety features such as a locking mechanism, for example, to provide a means of child-proofing or locking the medication 131 within the dispensing apparatus 100. As an example, the lever 104 may be provided with a lock requiring a user to push the lever in a particular direction in order to unlocked and moved. It should be understood that any suitable means may be used to provide a child-proofing or safety feature to the pill dispensing system of the dispenser 100 that also allows a user convenient and easy access to their medication.

When a bottle 102 is to be changed for a new bottle or a refill, or the pill tube 111 needs to be changed for any other purpose, the pill tube 111 may be removed from the base 101 by carrying out the following exemplary process. The sliding door 106 may be moved to expose the pill tube 111. Next, the user pushes the release button 123 which causes the pill tube 111 to protrude out of the receiving slot 105. Next, the pill tube 111 is removed completely out of the base 101.

Again, the compact dispenser 100 may, for example, be operated for dispensing pills by moving the lever 104, which the user may slide up or down in the directions indicated by arrow 134 as shown as an example. As an example, the lever 104 may be associated with a rack and pinion actuator or any other suitable means causing a rotation of the pill tube to catch a pill from the funnel 108. The dispensed pill may then be released from the compact dispenser 100 through the exit tube 138, and next fall into the pill catcher 107.

Lights 122, which may be RGB LED lights, for example, may be used as indicators or notifications to the user, such as when it is time to dispense a pill, such as by the exemplary process described above. Exemplary alerts or notifications that the lights 122 may be used for may include drug interactions, drug allergies, a scheduled pill consumption, the need for a drug refill, and other such similar notifications or warnings. The dispenser may be provided with a built-in battery or similar power source having a circuit board to power the LED lights and communicate with, for example, a mobile device.

As shown in FIG. 1B, the compact dispenser 100 may be provided with a pill cutting carrier ("pill carrier," "pill cutting carrier," "cutting carrier," or "carrier") 110, which may be used for cutting pills. The pill carrier 110 may be provided with a cutting hole or a plurality of cutting holes 110-a, which may be different sizes to accommodate different types or sizes of pills or other medication. The carrier may be associated with the base 101 of the compact dispenser 100, and may be associated with the base 101 by a hinge, for example. The carrier 110 may thus swing outwards from the base 101 and back inwards, such as in the directions indicated by arrows 146, and provide access to the cutting holes 110-a when out of the base 101. The carrier 110 may be housed in the base 101 when the carrier 110 is pushed back into a carrier slot 133 within the base 101. As an example, the carrier 110 may be released from the base 101 or locked back into the base 101 by a pushing action and may be locked in by a latch, for example. The base 101 may also house a cutting blade or razor 109, which may fit into a razor slot 132 of the carrier 110 when the carrier 110 is inserted into the carrier slot 133, thus causing the razor 109 to pass through the pills within the pill receiving holes 110-a and cutting the pills into halves. The user may then release the carrier 110 from the carrier slot 133, and remove the cut pills from the cutting holes 110-a.

Figure 7A:
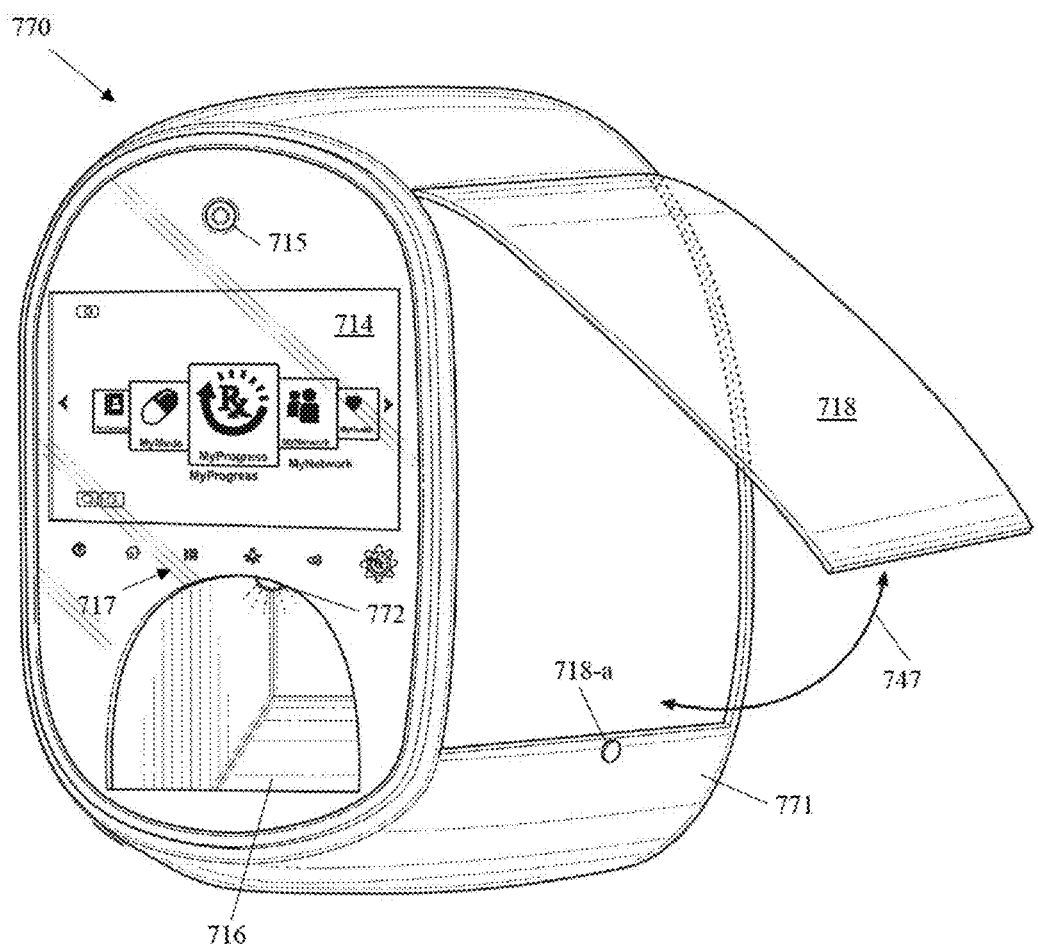
FIGS. 7A-7C illustrate the front perspective view, the front view, and the sectional top view, respectively, of another example of the medication dispensing apparatus, according to an aspect.
Figure 7B:
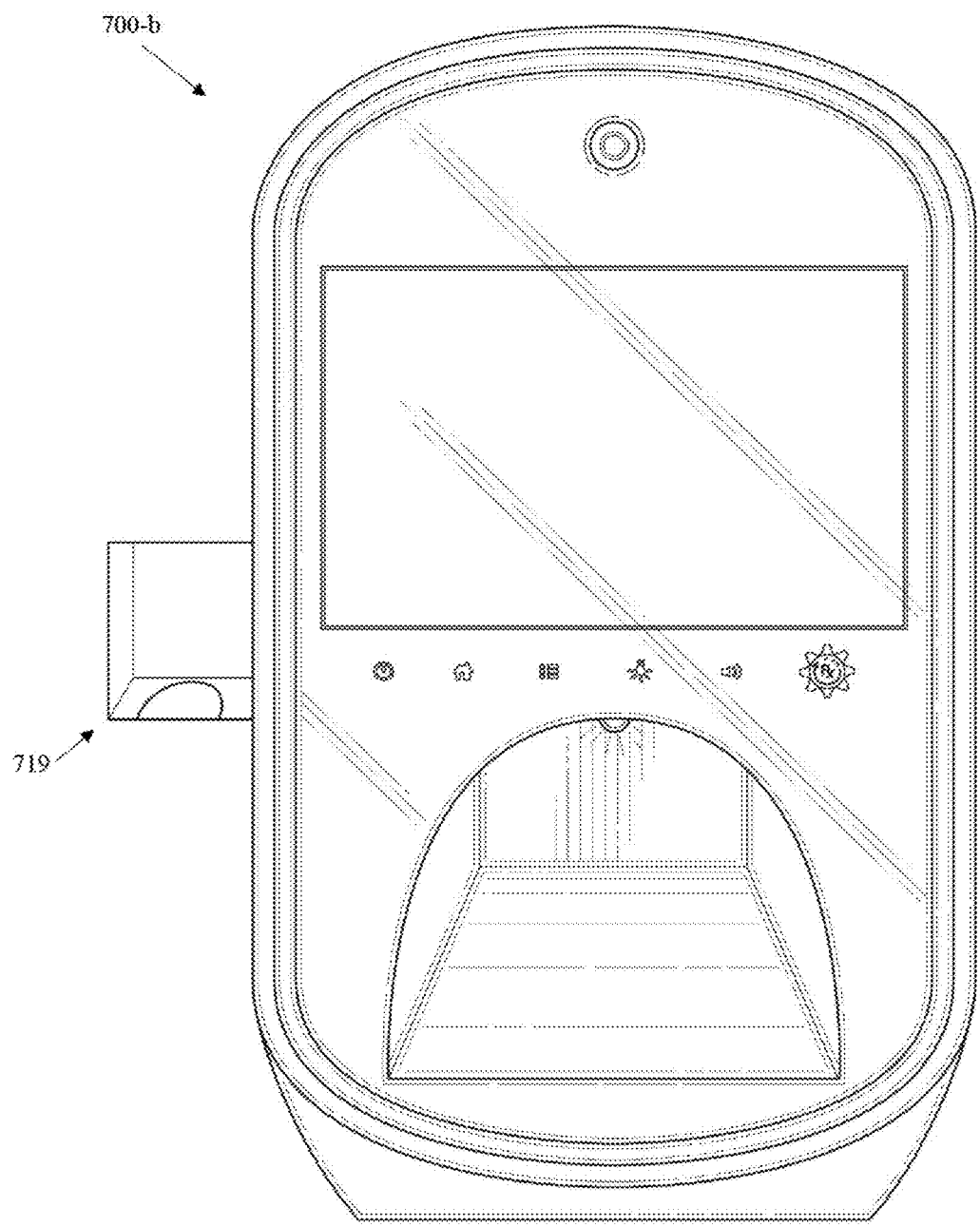
Figure 7C:
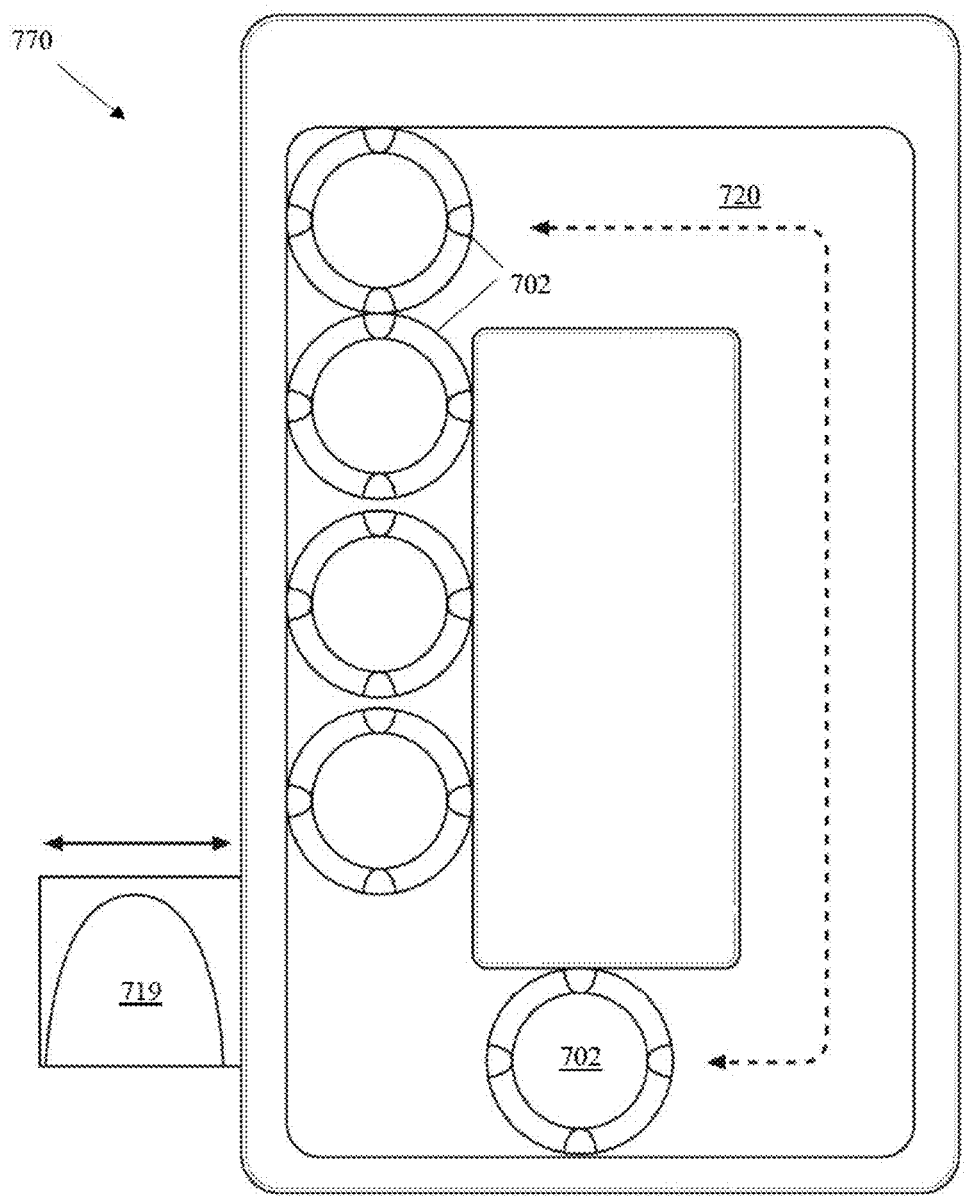

FIGS. 2A-2B illustrate the side perspective view and the top plan view of the funnel 208, the pill tube 211, and the pill tube holder ("pill tube holder" or "tube holder") 241 of a medication dispensing apparatus, according to an aspect. As an example, a pill dispensing system using a funnel 208, a pill tube 211, and a pill tube holder 241 may be used with a compact or travel-size medication dispenser as shown in FIGS. 1A-1B, or may be used with a tabletop medication dispenser, as shown in FIGS. 7A-7C, or any other suitable medication dispensing apparatus.

The funnel 208 may be provided with threads 208-a such that a medicine bottle (as shown by 102 in FIG. 1A) may be screwed onto the funnel, or the funnel 208 may as another example be provided with channels for the bottle to rest in. The pill tube 211 may be cylindrical and hollow to hold a pill released from the funnel 208. The tube 211 may have a pill tube hole 243 at a center portion of the tube such that when the pill tube hole 243 is facing upwards, the pill tube hole 243 is substantially aligned with the bottom of the funnel 208. Thus, the pill tube 211 may hold within it a pill (not shown) caught from the funnel until the pill is released out of the medication dispenser. When the system is actuated to release a pill, the pill tube 211 and the pill tube holder 241 may rotate, as indicated by arrows 242, such that the pill tube hole 243 faces downwards and releases the pill from within the hollow pill tube 211 into, for example, an exit tube (as shown in FIG. 1A). The pill dispensing system may accommodate various types of medications by providing a plurality of pill tubes 211 having different sizes and shapes of pill tube holes 243. Again as an example, a user may scan a prescription bottle or paper prescription (as will be described further when referring to FIGS. 7A-7B), and the medication management platform may inform the user which pill tube 211 should be used for the type of medication that was prescribed, such that the size and shape of the pill tube hole 243 matches the size and shape of the medication or pill. The appropriate pill tube 211 may then be selected, from a variety of provided pill tubes, and inserted into the pill dispensing system.

The pill tube holder 241 may be provided with a first end and a second end. The tube holder 241 may be provided with a gear 244 at the first end and at the second end. The gears 244 may rotate and cause a rotation of the inner pill tube 211-b, for example. The pill tube holder 241 may be shaped similar to a half-cylinder, or may have any curved or similarly suitable shape for receiving and holding the pill tube 211, such that the pill tube 211 rests on the holder 241 and such that the pill tube 211 and the pill tube holder 241 rotate together when the pill dispensing system is actuated and turned. The pill tube 211 may be provided with a groove 250-a along the length of the tube, and the pill tube holder 241 may be provided with a fin 250-b along the length of the pill tube holder. The pill tube holder 241 may be associated and locked together by aligning the groove 250-a with the fin 250-b such that the fin 250-b is captured within the groove. Thus, a movement of the tube holder 241 caused by a rotation of the gears 244 may also cause a movement of the tube 211.

Figure 3:
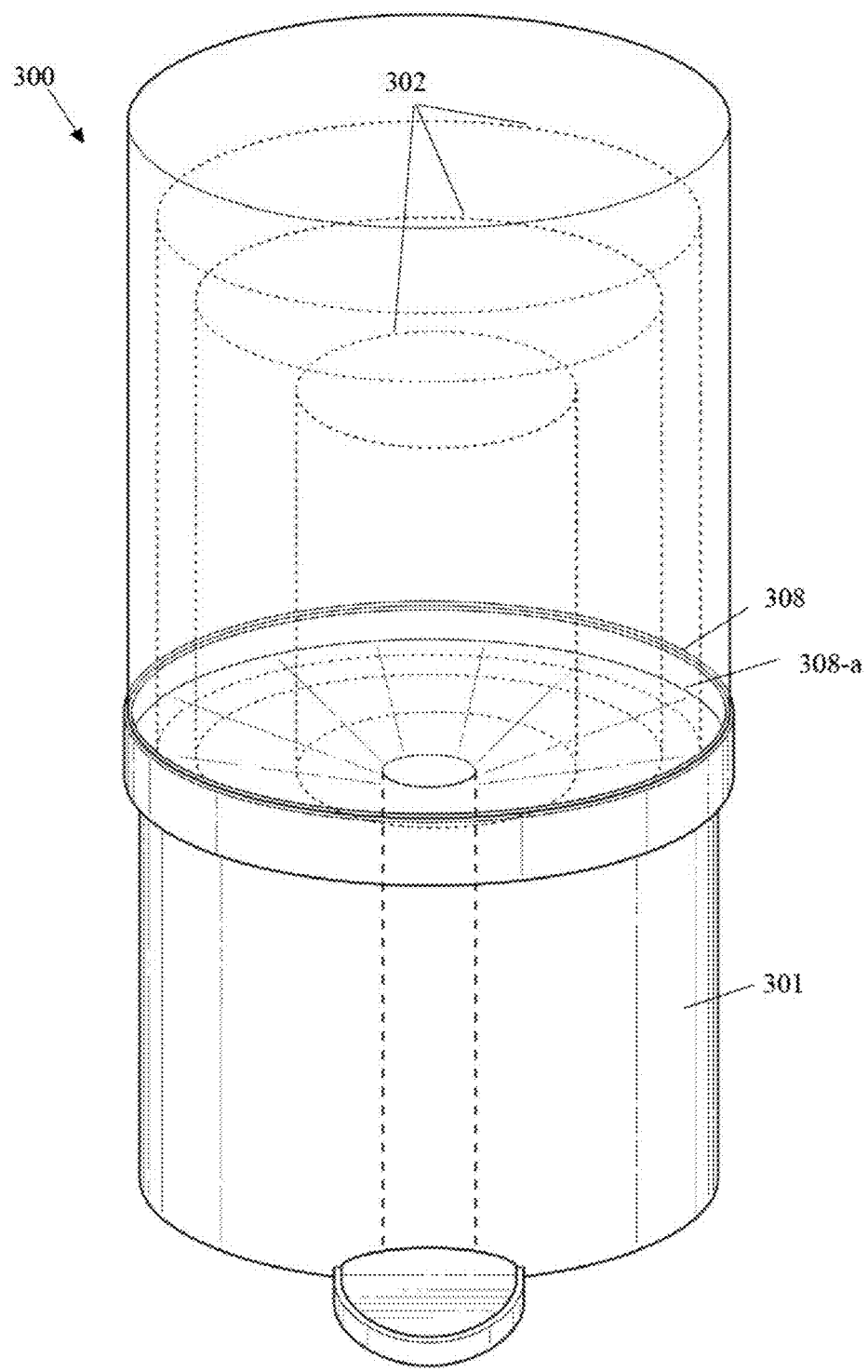
FIG. 3 illustrates front perspective view of another example of the compact dispenser apparatus in an assembled state, according to an aspect.

FIG. 3 illustrates front perspective view of another example of the compact dispenser apparatus 300 in an assembled state, according to an aspect. The compact dispenser 300 may accommodate various sizes of medicine bottles, as shown by the examples indicated by broken lines 302, wherein a bottle as indicated by 302 may screw into the base 301 via the funnel 308. Again, the funnel 308 may be provided with threads 308-a such that a bottle can be screwed in, or may be provided with channels for the bottle to slip into, or may be free of any threads. As another example, the funnel 308 may also be provided with channels such that the rim of a bottle 302 may sit within the channels and thus be secured into the funnel 308.

Figure 4:
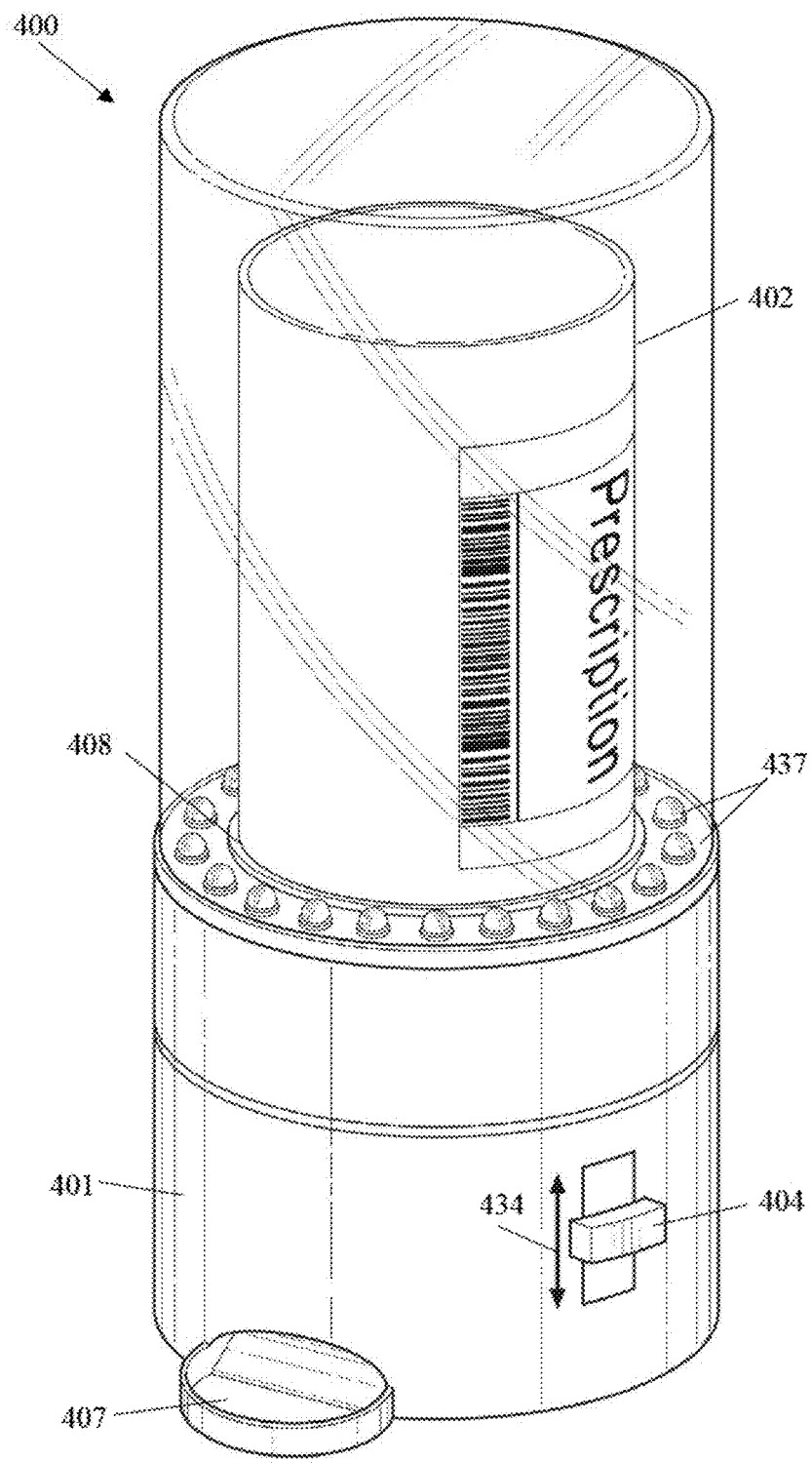
FIG. 4 illustrates the front perspective view of the compact dispenser apparatus in an assembled state, according to an aspect.

FIG. 4 illustrates the front perspective view of the compact dispenser apparatus 400 in an assembled state, according to an aspect. A bottle 402 is also shown attached to the funnel 408 within the base 401. Again, the base 401 may be provided with a lever 404, a pill catcher 407, and may also be provided with lights 437, which may be LED lights, for example. The lever 404 may, again, move in the directions indicated by arrows 434, which may actuate a rack and pinion system.

Figure 5A:
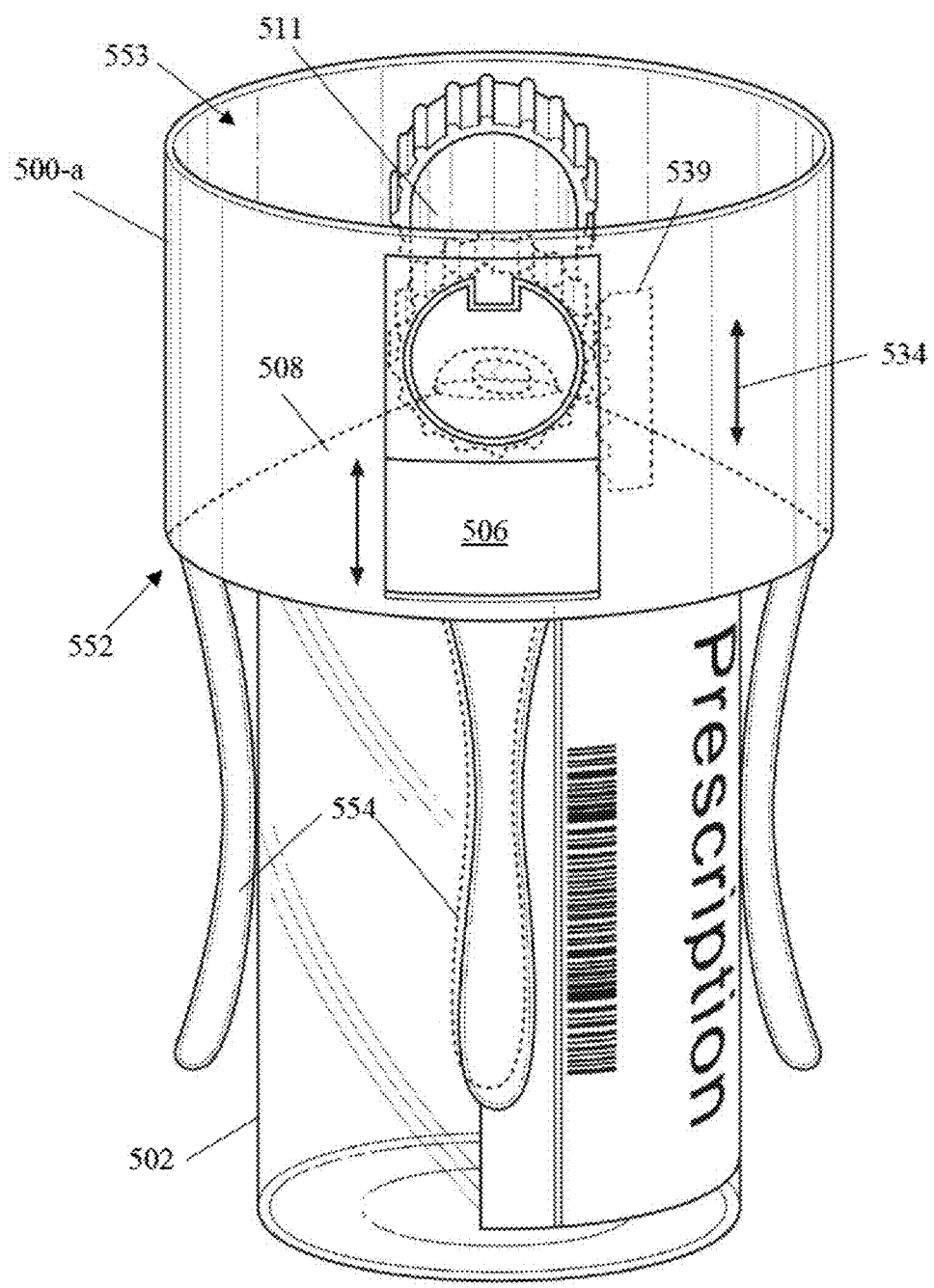
FIGS. 5A-5B illustrate the upside down right perspective view and the right side up left perspective view, respectively, of an open-ended locking pill bottle cap, according to an aspect.
Figure 5B:
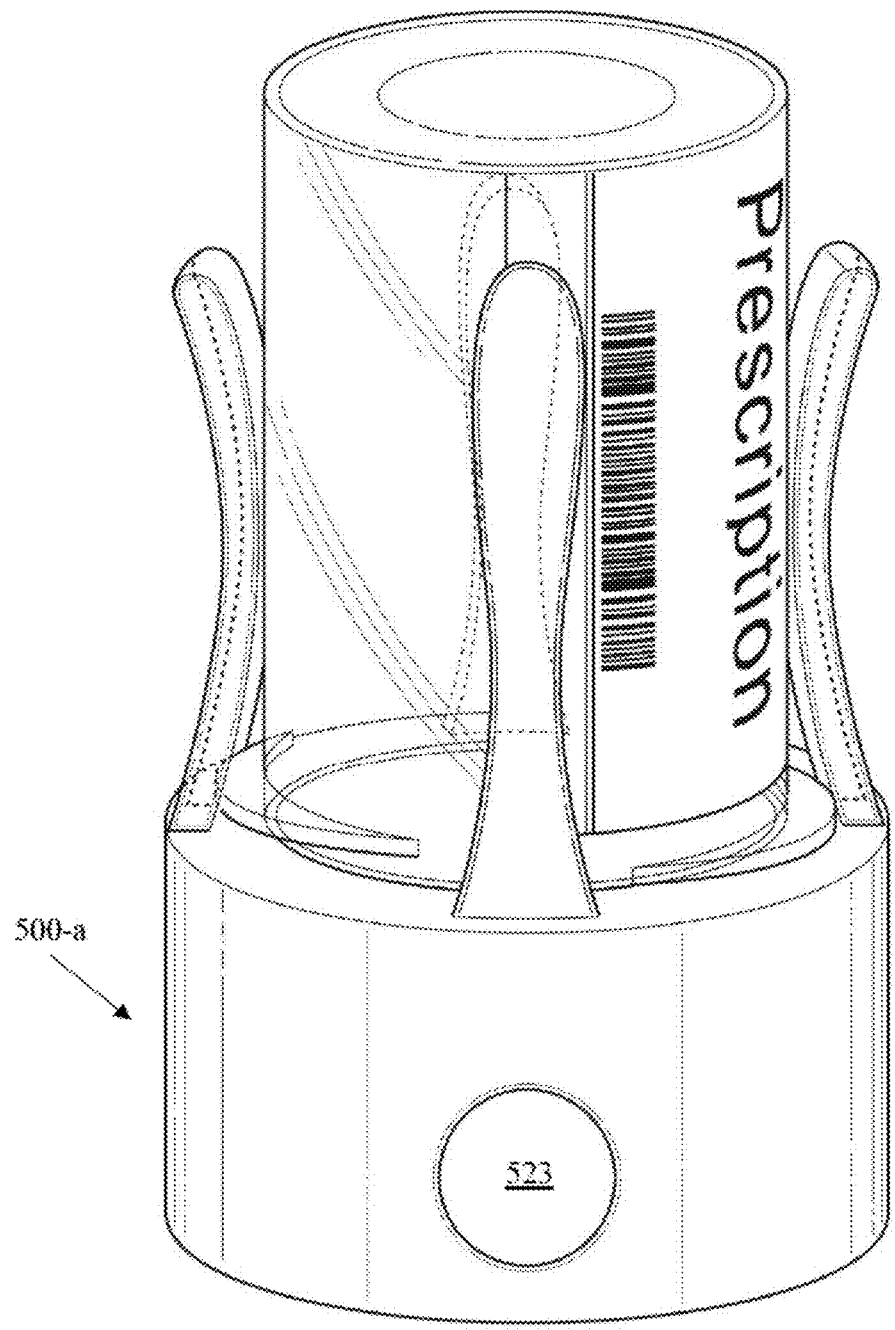

FIGS. 5A-5B illustrate the upside down right perspective view and the right side up left perspective view, respectively, of an open-ended locking pill bottle cap ("open-ended cap," "locking pill bottle cap," "pill bottle cap," "locking cap," or "cap") 500-a, according to an aspect. As an example, a pill dispensing system as described when referring to FIGS. 2A-2B may be provided within a cap 500-a having a first end 552 for receiving a bottle 502, and an opposite second end 553.

As an example, the cap 500-a may house a pill tube holder (not shown), a pill tube 511, which may be selected according to the size and shape of the medication being used, a funnel 508, gears 544, a gear arm 539, a sliding door 506 on a first side as shown in FIG. 5A, and a release button 523 on a second side opposite to the first side as shown in FIG. 5B.

The second end 553 may be open and may thus provide access to the pill dispensing system, such that an external device or apparatus may access the gear arm 539 in order to provide an actuation of the pill dispensing system. A device, such as a tabletop medication dispenser (as will be further discussed when referring to FIGS. 7A-7C), may provide a means of actuating the gear arm, for example, and may move the gear arm such as in the directions indicated by arrow 534.

The cap 500-a may be provided with a means for securing the cap 500-a to the bottle 502, such as the vertical arms 554 in the example shown in FIGS. 5A-5B. The vertical arms 554 may be spring-loaded, or may be biased towards each other by any suitable means such that when fitted onto a bottle 502, the arms 554 are able to grip the bottle 502.

Figure 6A:
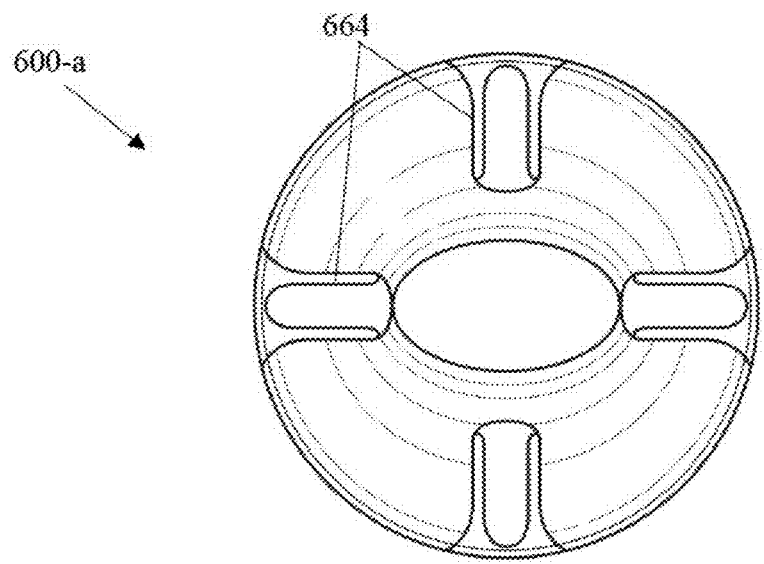
FIGS. 6A-6D illustrate the top plan views of various examples of a locking pill bottle cap, according to an aspect.
Figure 6B:
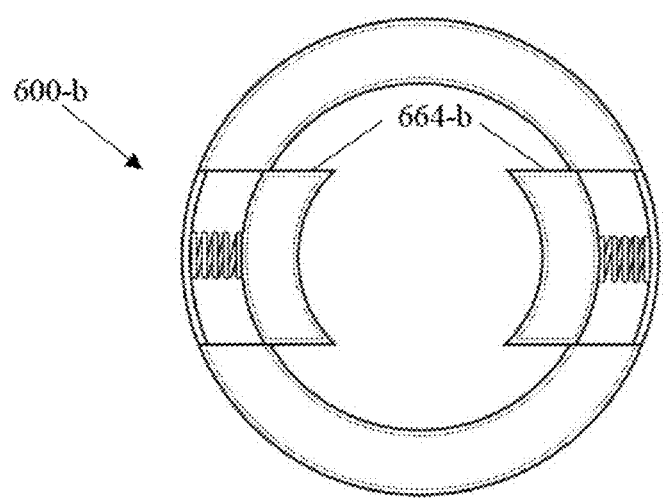
Figure 6C:
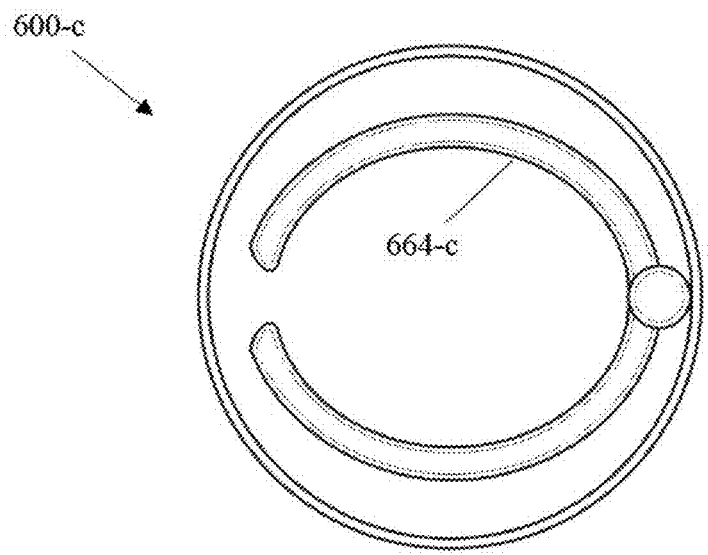
Figure 6D:
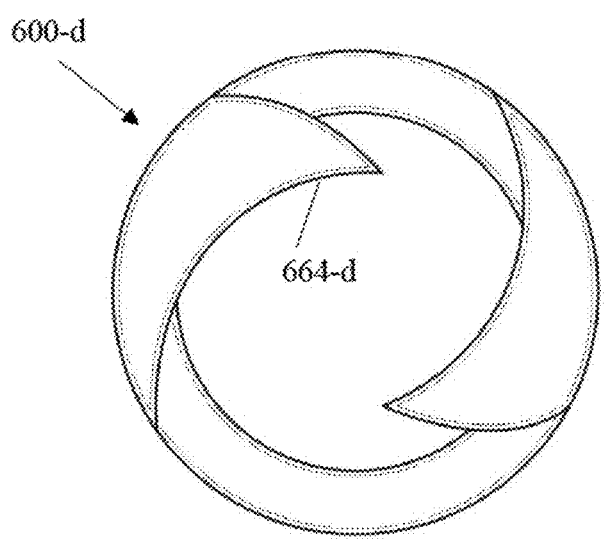

FIGS. 6A-6D illustrate the top plan views of various examples of a locking pill bottle cap 600-a through 600-d, according to an aspect. The cap 600-a of FIG. 6A shows a cap with vertical arms 664, as shown in FIGS. 5A-5B, wherein the vertical arms 664 may grip onto the sides of a bottle. The cap 600-b of FIG. 6B shows a cap with spring-loaded grips 664-b, which may be biased together. The spring-loaded grips 664-b may be pushed apart to be fitted onto a bottle, and when released may bias together to grip onto the bottle. The cap 600-c of FIG. 6C shows a clasp 664-c which may be biased together, and pushed apart to be fitted onto a bottle. The clasp 664-c may be biased together to grip onto the bottle when released. The cap 600-d of FIG. 6D shows an aperture closure which may be twisted open or closed in order to release or grip a bottle.

It should be understood that a locking cap may also be secured to a medicine bottle by any suitable means, such as by providing threads, magnetic closure, or any other locking or clasping mechanism, for example.

FIGS. 7A-7C illustrate the front perspective view, the front view, and the sectional top view, respectively, of another example of the medication dispensing apparatus ("tabletop medication dispensing apparatus," or "tabletop apparatus") 770, according to an aspect. The tabletop dispenser 770 may, for example, be placed on a table, counter, or any other suitable surface. The tabletop dispenser 770 may be provided with a housing 771, cameras 715 and 772, a screen 714, a control panel 717, a maintenance door 718, a pill loader 719, a dispensing area 716 and a conveyer belt 720. The screen 714 may, for example, be a touchscreen interface. The maintenance door 718 may allow a user access to the inside of the apparatus for maintenance, changing parts, or any other purpose that requires access to the interior of the apparatus. The maintenance door 718 may be opened with, for example, a release button 718-a, and may swing outwards such as in a direction indicated by arrow 747. As an example, a camera 715 may be used for making video calls or for recording videos, and a camera 772 may be used for sensing, scanning, or reading prescriptions.

Exemplary additional features that the tabletop dispenser 770 may be provided with may include a speaker, Bluetooth and Wi-Fi connectivity capabilities, a power source or cord for connecting to a power source, BIOS, a maintenance door release button 718-a, and a light (not pictured).

As an example, the tabletop dispenser may be used in place of or in conjunction with a mobile application for medication management, and may provide the user with the functions provided by the mobile application. As an example, the camera 772 may scan prescriptions in order to import data, or a smartphone with a camera and the mobile application for medication management may be used to scan prescriptions and import data.

To begin use of the tabletop dispenser 770, a user may carry out the following exemplary process. First, the user touches a button of the control panel 717 or on the touchscreen interface 714 to begin scanning. The command from the control panel or touchscreen activates the built-in device camera 715. Next, the user lines up the camera view with the prescription label. The tabletop dispenser 770 may be provided with OCR or similar technology to read the information on the prescription label and converts the image to text that becomes imported into the database for medication management. The medication management platform can then store the data such as information related to the pharmacy, patient, doctor or other care provider, and medication into the user's profile. Next, the medication management platform instructs the user on the type of cap or pill tube that should be used with the type of medication that was scanned in. Next, the user removes the medication bottle's provided cap, and replaces the cap with the specified cap such that the hole of the pill tube is sized and shaped for the medication being used with the tabletop dispenser. Next, the user inserts the medication bottle fitted with the specified cap into the tabletop dispenser by opening the pill loader 719 and placing the bottle inside. Next, the medication management platform may provide the user with alerts through the tabletop dispenser, a smartphone application, or both, such that the user is notified when medication needs to be consumed, and the user may press a button on the dispenser to release a pill. Next, the medication management platform connected with the dispenser may turn off the alert, and record the medication consumption event.

The medication management platform may track pill dispensing, and alert the user whenever a pill is dispensed. An advantage may be that the user may not need to track or record medication consumption themselves, and any unauthorized dispensing of pills may also be alerted to the user. Another advantage may be that the user may have access to medical history, medical benefits, side effects, and other information about a medication such as active ingredients and interactions with other medication. Doctors may also have the ability to set up a medication reconciliation profile for a user, and may make or track changes to the user's profile. The user may also have the option of setting up family alerts, social support, and face-to-face calls with doctors, the doctor's office, and family members, for example. As an example, a plurality of cameras may be provided, such as a camera 772 for scanning a prescription, and a camera 715 for making video calls or making videos when dispensing medication.

The user may also have access to lists of medication, medication schedule or timetables, alerts, doctors, education about medicine, warnings, and social support through the medication management platform accessed through the tabletop dispenser 770 or through a mobile application.

As shown in FIG. 7C, the interior of the tabletop dispenser 770 may be provided with a conveyer belt 720, such that multiple medicine bottles 702 may be stored in the dispenser 770 and dispensed according to a user's needs or prescription. Each medicine bottle 702 inserted into the tabletop dispenser 770 may be fitted with an appropriate open-ended cap such as the caps shown in FIGS. 5A-6D, where an actuator from the tabletop dispenser 770 may reach into the pill dispensing system of the cap and actuate the pill dispensing. The tabletop dispenser 770 may, for example, dispense pills using a system similar to the pill dispensing system as shown and described in FIGS. 1A-1B. The pills may then dispense into the dispensing area 716, which may be provided with a light (not pictured) for the user to easily see and access the medication.

Again, the medication management platform may be used with a tabletop dispenser 770, which may display information to the user on the screen 714, and the platform may also be used with a mobile application, which may utilize a smartphone or similar device to display information to the user. The user may also use both the tabletop dispenser 770 and a mobile application to track and manage their medication with the medication management platform, and the platform may provide syncing capabilities such that both the dispenser 770 and the mobile device are in communication and updated, for example.

Figure 8A:
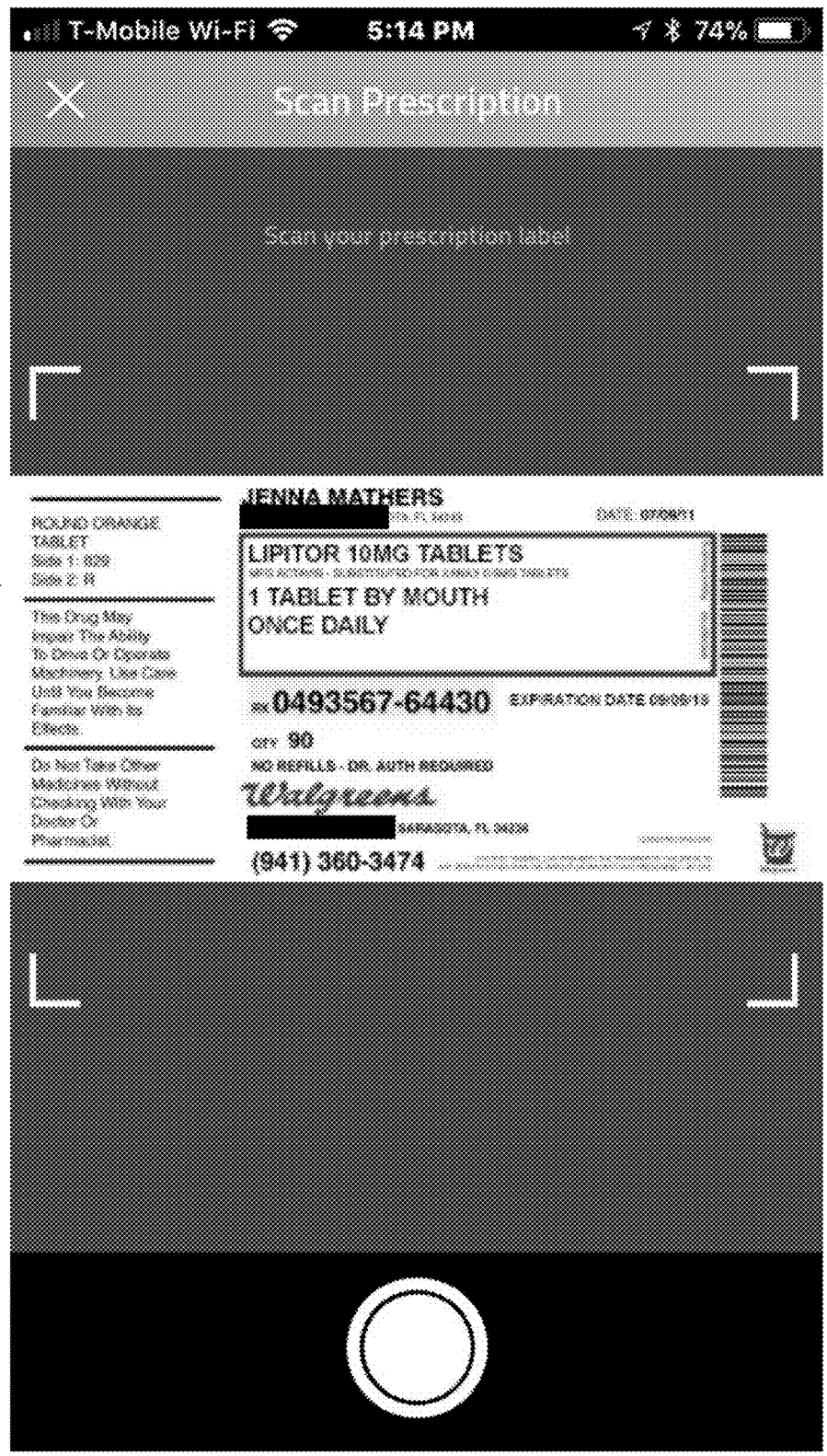
FIGS. 8A-8C illustrates examples of a user interface that may be accessed by a user to scan a prescription and import the information contained within it into the medication management platform, according to an aspect.
Figure 8B:
Figure 8C:
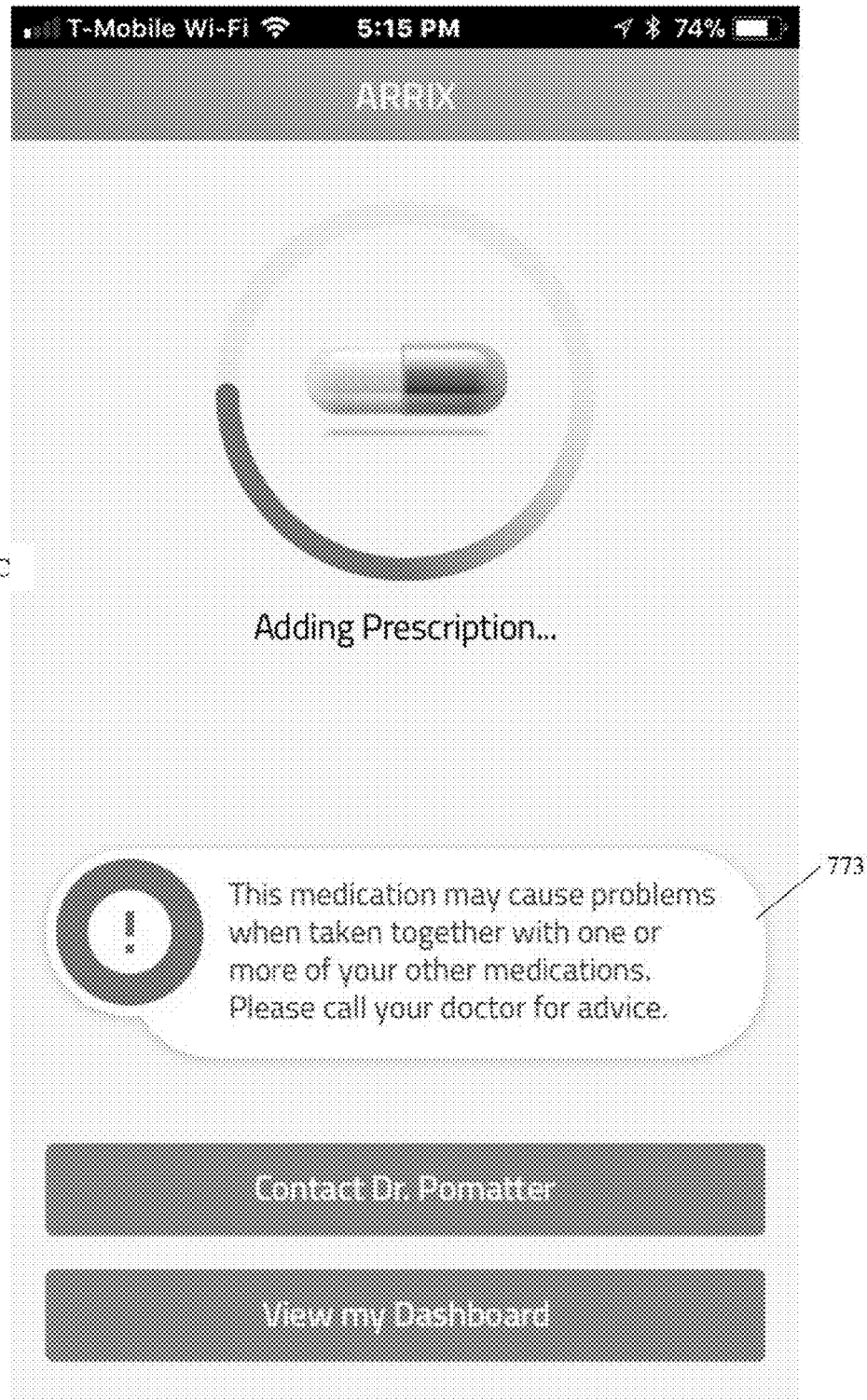

FIGS. 8A-8C illustrates examples of a user interface that may be accessed by a user to scan a prescription and import the information contained within it into the medication management platform, according to an aspect. It should be understood that while the focus of FIGS. 8A-12C is on accessing the medication management platform through a mobile application, similar interfaces may be accessed and provided to the user if accessing the medication management platform through the tabletop dispenser as shown in FIGS. 7A-7C, or through a web browser such as on a computer or other electronic device.

An exemplary process for using the medication management platform is as follows. First, the user downloads and installs the medication management platform as a mobile application onto their electronic device, or accesses the platform through a computer, or may access the medication management platform provided with a tabletop apparatus (as shown by 770 in FIGS. 7A-7C). Next, the user picks up medication from a pharmacy and makes note of whether or not a paper prescription is included with the medication. Next, the user launches the application on their electronic device or tabletop dispenser. Next, the user launches the camera of the mobile device or tabletop dispenser through the application, such as by pressing an animated scan button. As an example, scanning may also be prompted by inserted a prescription into area 716, when the camera senses a readable prescription. Next, the user lines up the camera to capture an image of the prescription medication label. Next, the OCR technology of the medication management platform converts the image into text, and imports the data into the user's profile and the platform database. The medication management platform may then display relevant information to the user such as instructions, and provide the user with timed notifications and alerts related to the medication and the prescription schedule.

As shown in FIGS. 8B-8C, various confirmation screens may be shown to a user when adding a prescription, as an example. After scanning a prescription, information about the medication and the doctor's information may be displayed to the user, as shown in FIG. 8B. The information may also be accessed through the application by the user later on when accessing the platform. The user may also easily access the ability to contact their doctor through the platform. Warnings or other similar relevant notifications 773 may be displayed to the user when the medication or prescription is added to the database or user's profile.

Figure 9A:
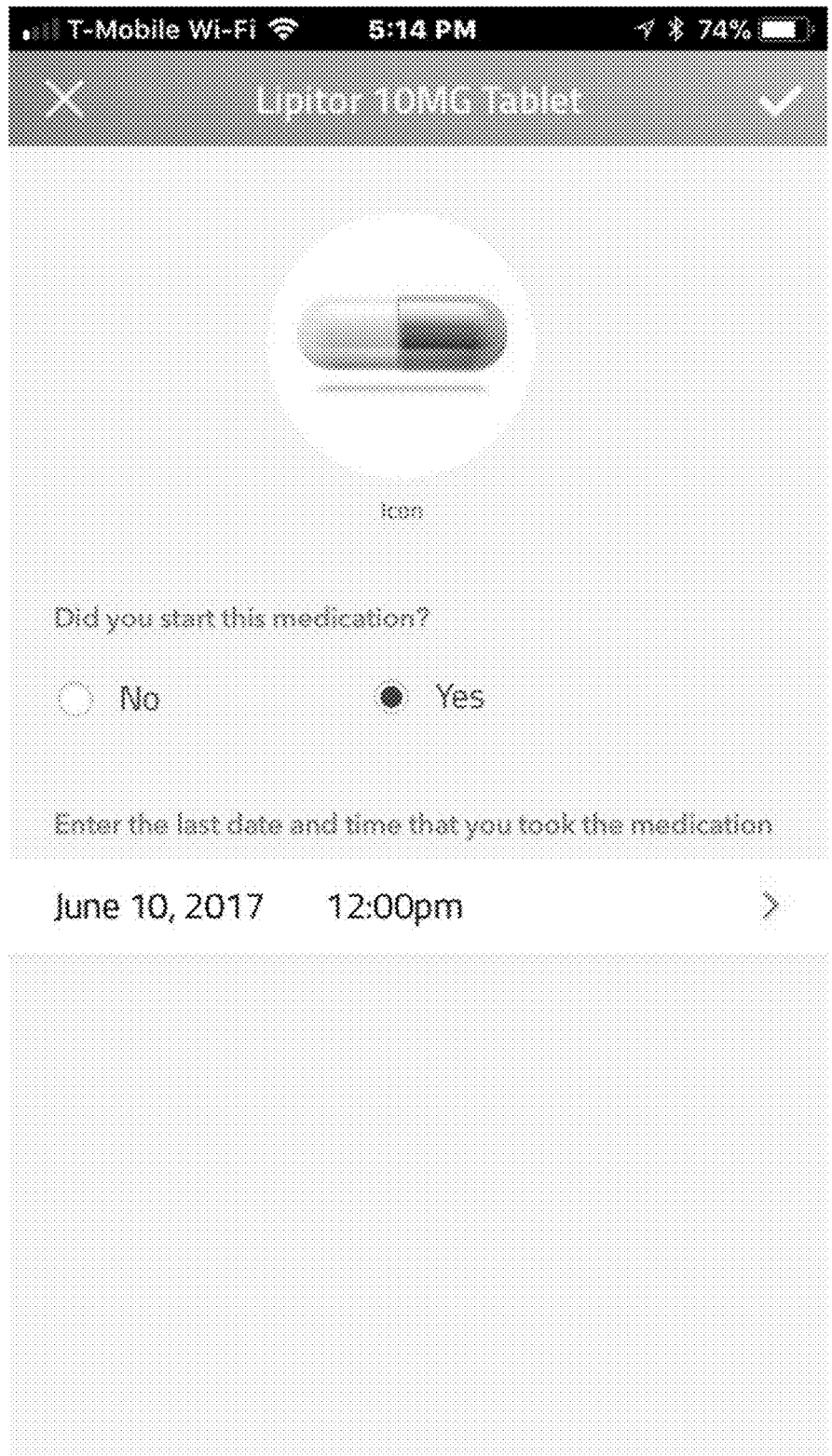
FIGS. 9A-9D show examples of user interfaces that may be accessed by a user to begin a prescription schedule or begin tracking their medication intake using the medication management platform, according to an aspect.
Figure 9B:
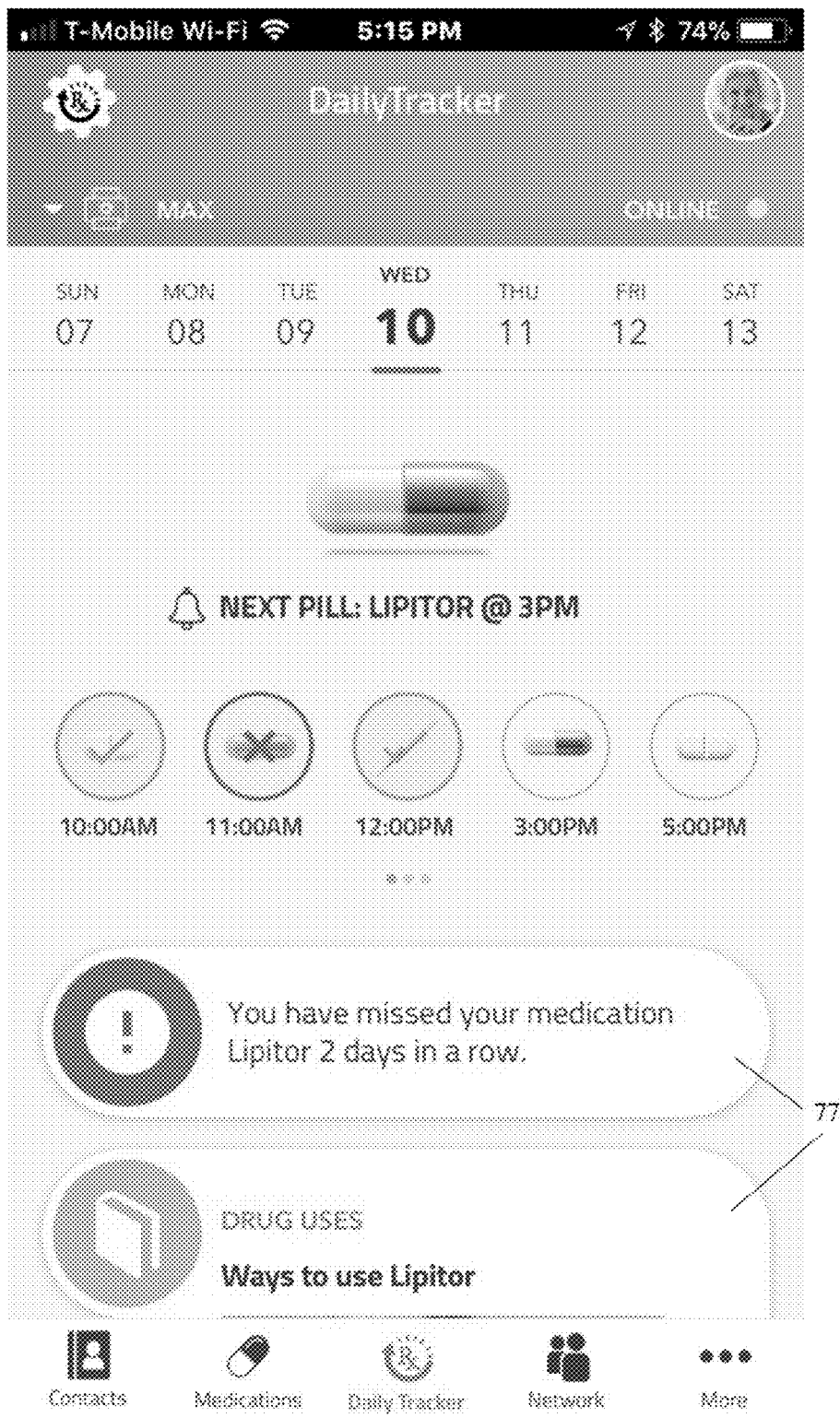
Figure 9C:
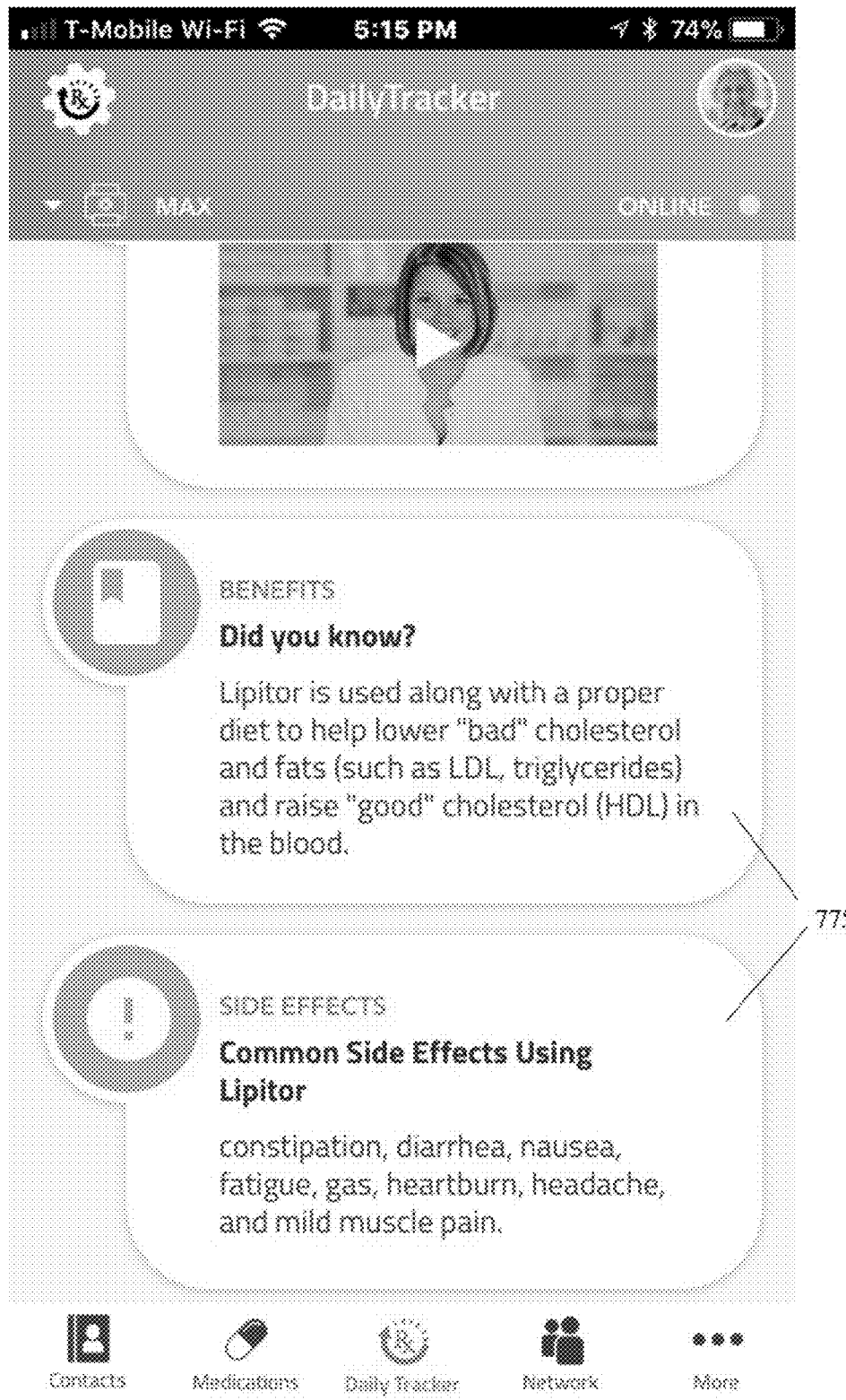
Figure 9D:
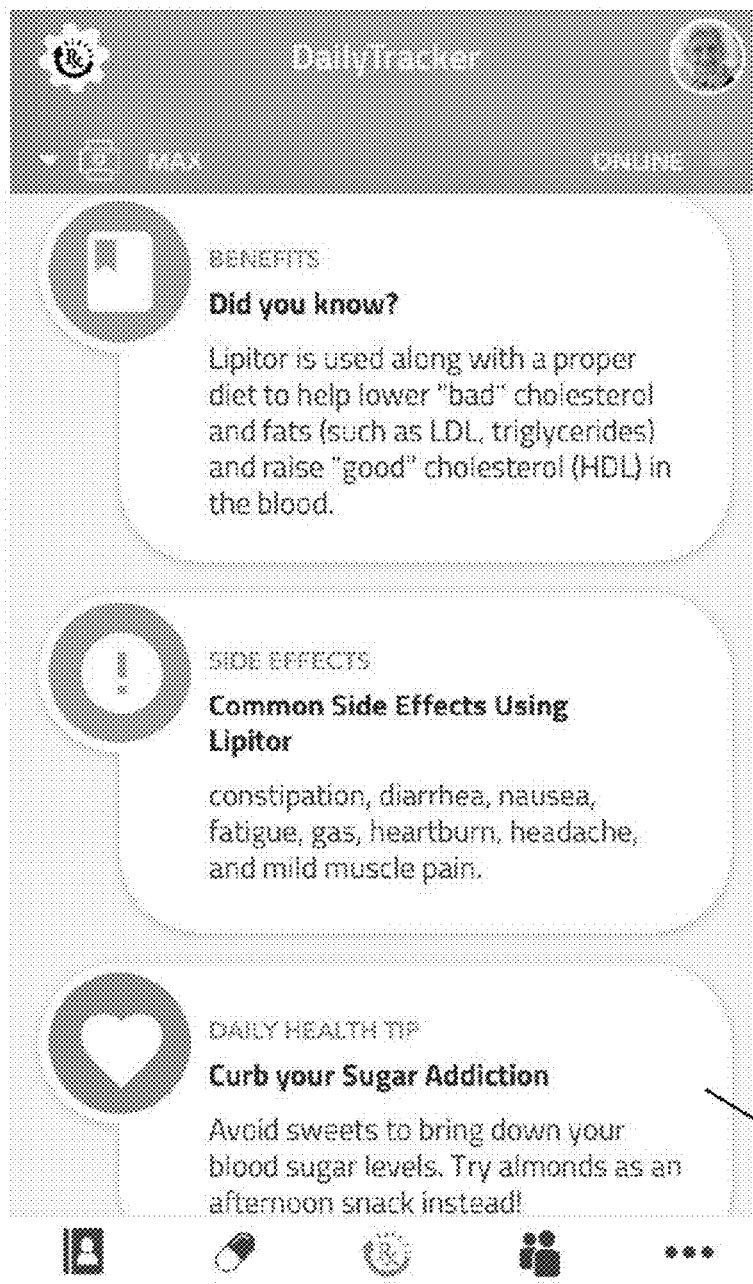

FIGS. 9A-9D show examples of user interfaces that may be accessed by a user to begin a prescription schedule or begin tracking their medication intake using the medication management platform, according to an aspect. Various prompts or questions may be provided to the user such that medication tracking may take place and be recorded by the medication management platform. A calendar may also be provided to the user to view a schedule of medication intake, and information such as the next scheduled doses may be shown to the user, as shown in FIG. 9B. Health tips may also be shown, such as the example 774a in FIG. 9D. Warnings or notices about a user's prescription medication may be shown, such as the examples 774, as well as additional information such as the examples shown as 775 regarding the medication.

Figure 10A:
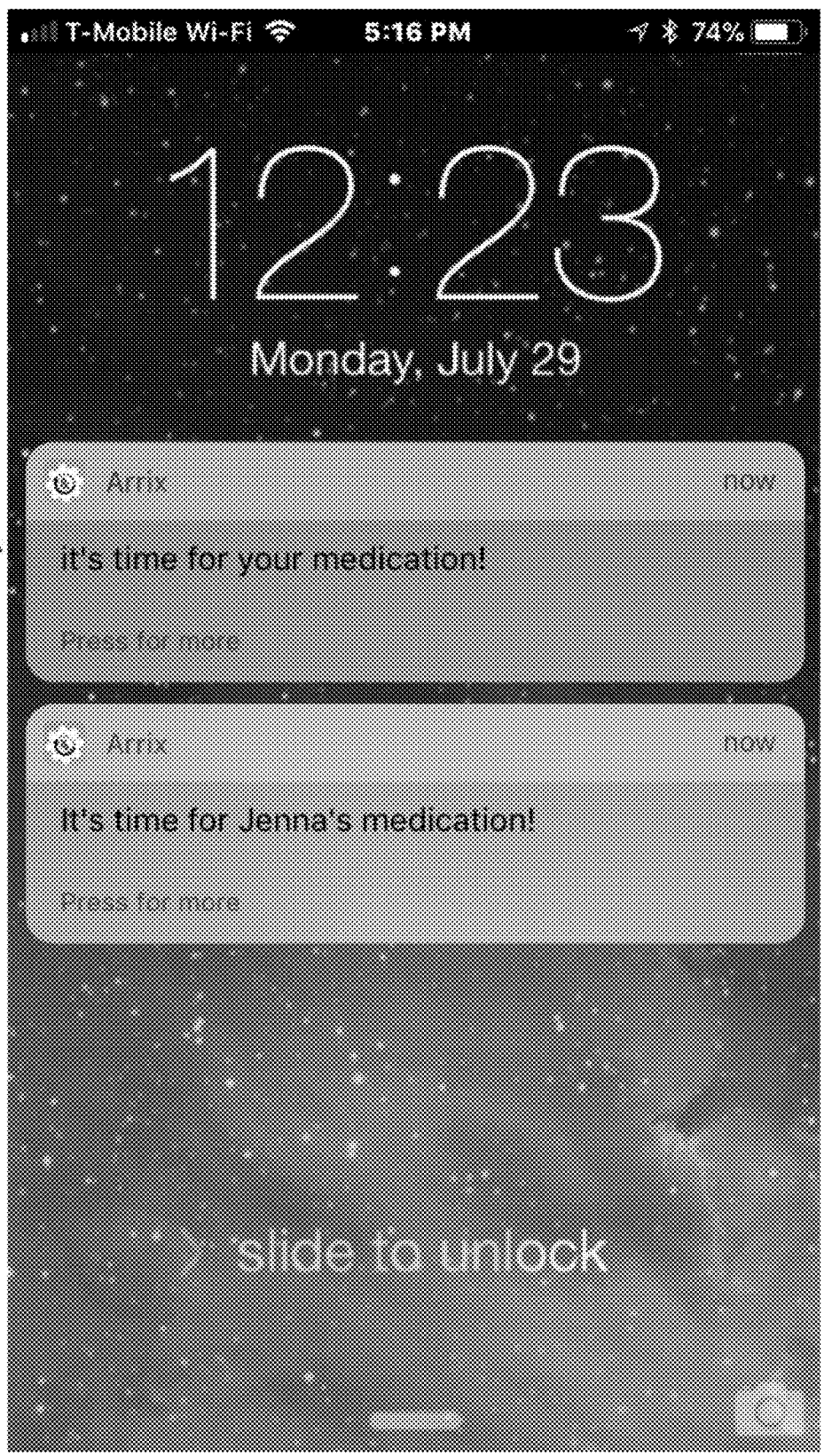
FIGS. 10A-10B show examples of user interface that may be shown to a user related to receiving alerts or notifications about a prescription, according to an aspect.
Figure 10B:
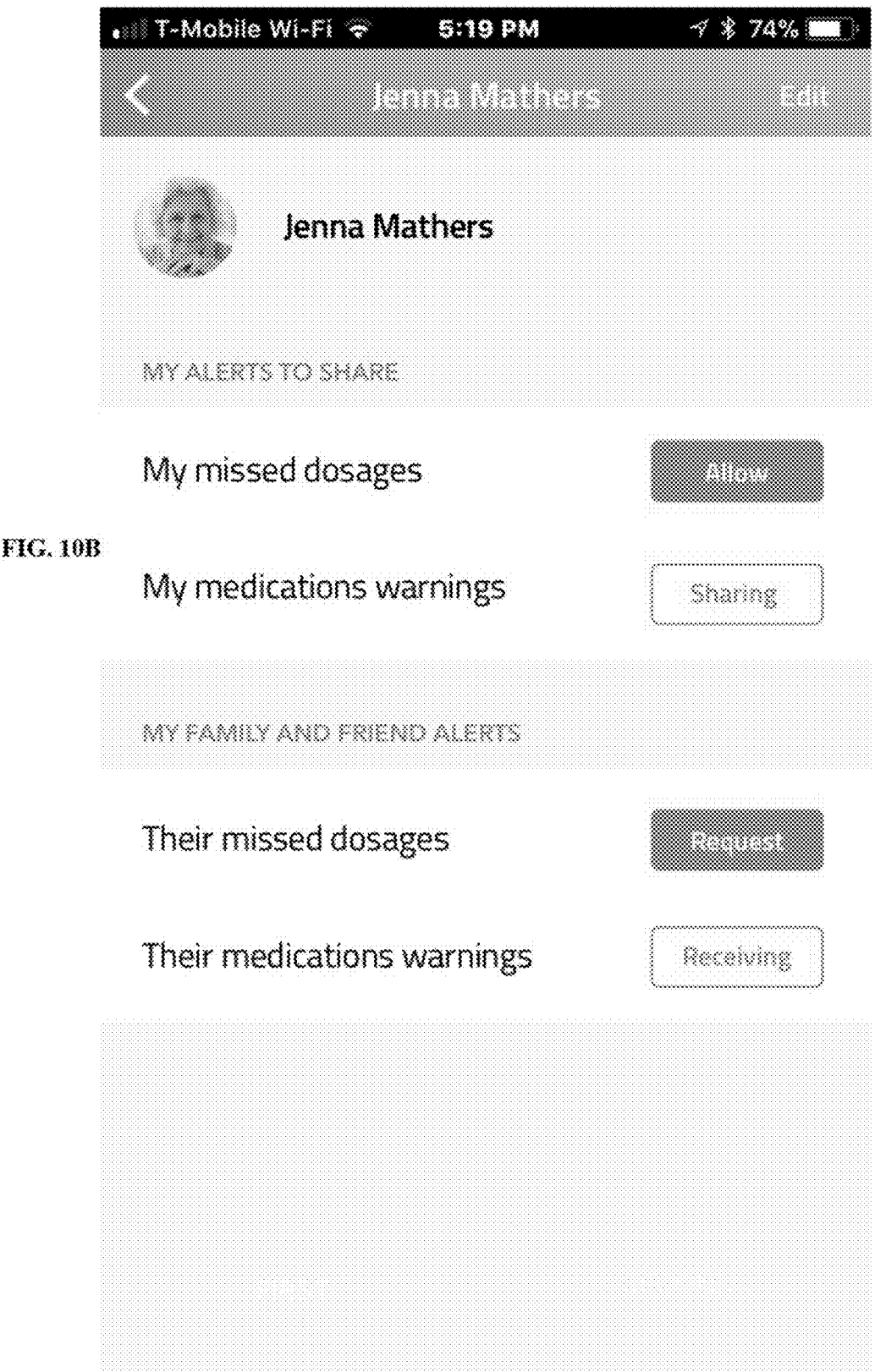

FIGS. 10A-10B show examples of user interfaces that may be shown to a user related to receiving alerts or notifications about a prescription, according to an aspect. When a user has begun tracking medication intake for a particular prescription, the medication management platform may send notifications such as push notifications on a user's electronic device. A user may also receive alerts for another user's medication schedule, for example, when users wish to support or track another person's prescription schedules. As shown in FIG. 10B, a user may select the types of alerts they wish to receive, such as an alert for missing a dosage or a warning about medications that are stored in their user profile. A user may also opt to receive alerts and notifications related to another user's medication management, for example, as shown in FIG. 10B. Similar notifications may also be sent via colored lights of a compact dispenser as shown in FIGS. 1A-1B, for example, or through the touchscreen interface of a tabletop dispenser as shown in FIGS. 7A-7B.

Figure 10C:
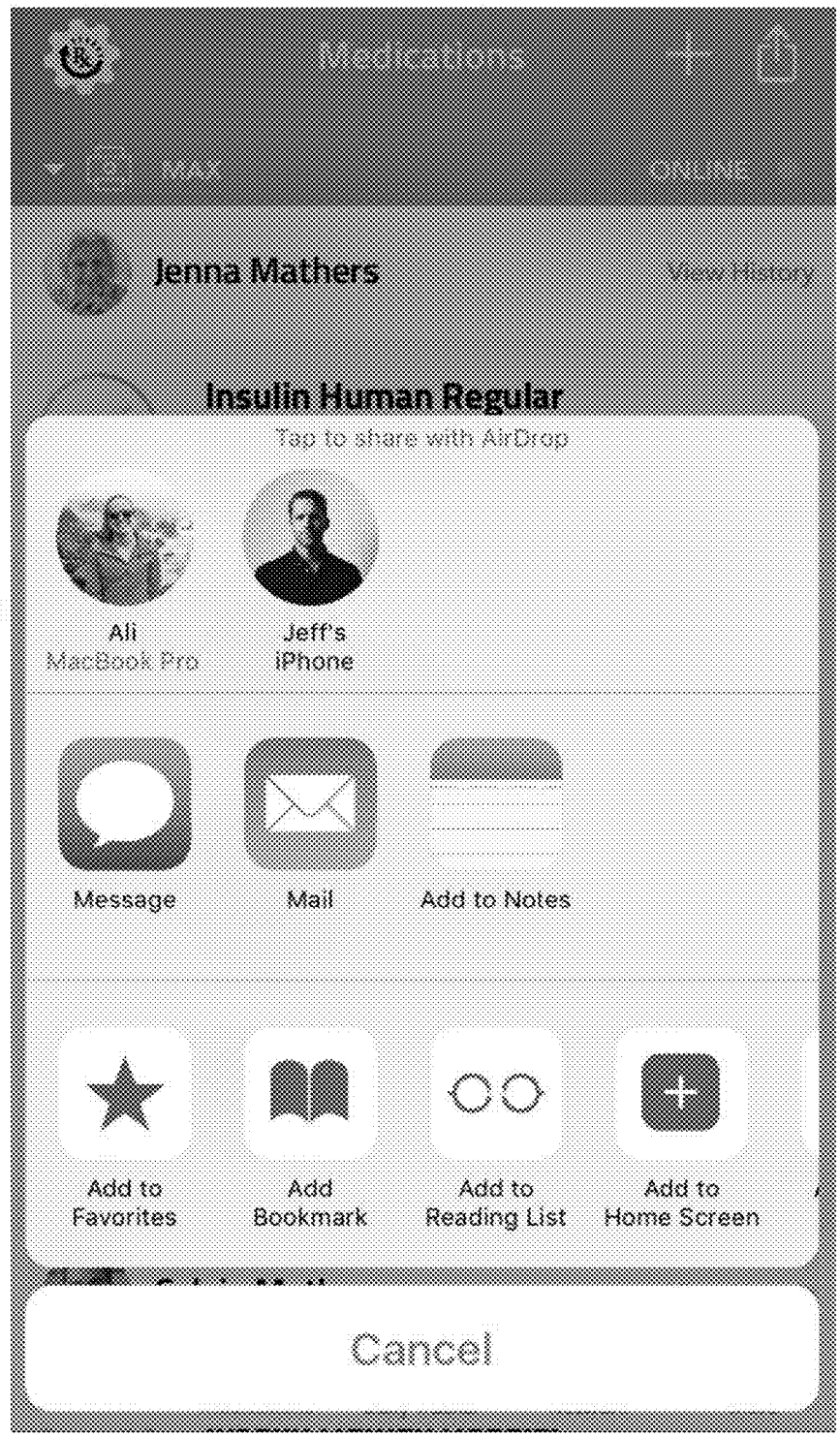
FIGS. 10C-10D show examples of user interfaces that may be shown to a user related to creating and using a network, according to an aspect.
Figure 10D:
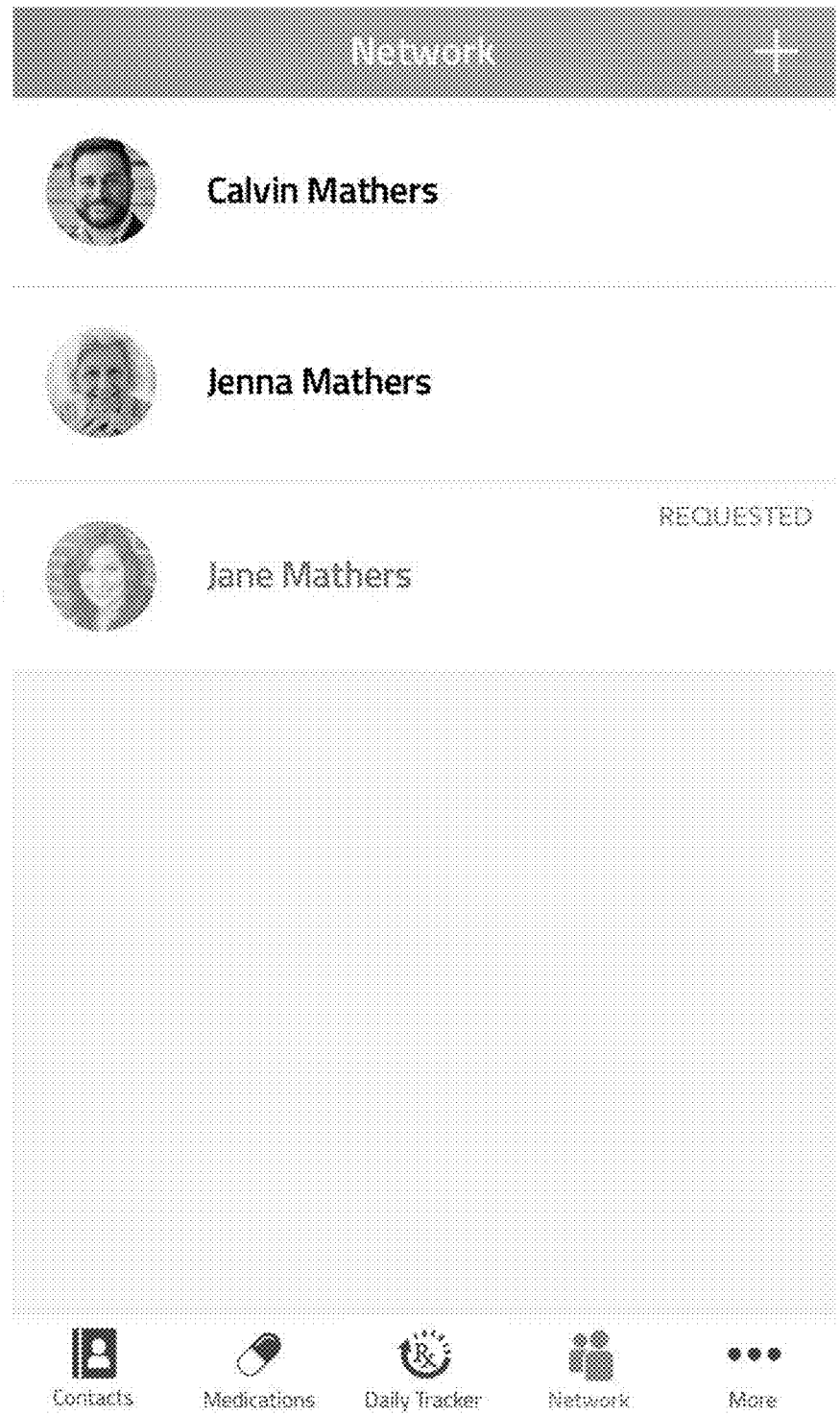

FIGS. 10C-10D show examples of user interfaces that may be shown to a user related to creating and using a network, according to an aspect. As discussed when referring to FIGS. 10A-10B, a user may add other users to their network and may share items of interest within the platform with other users (as shown in FIG. 10C). Additional users within a user's network may be shown in a list (or a grid or any other suitable manner) such as the example shown in FIG. 10D.

Figure 11A:
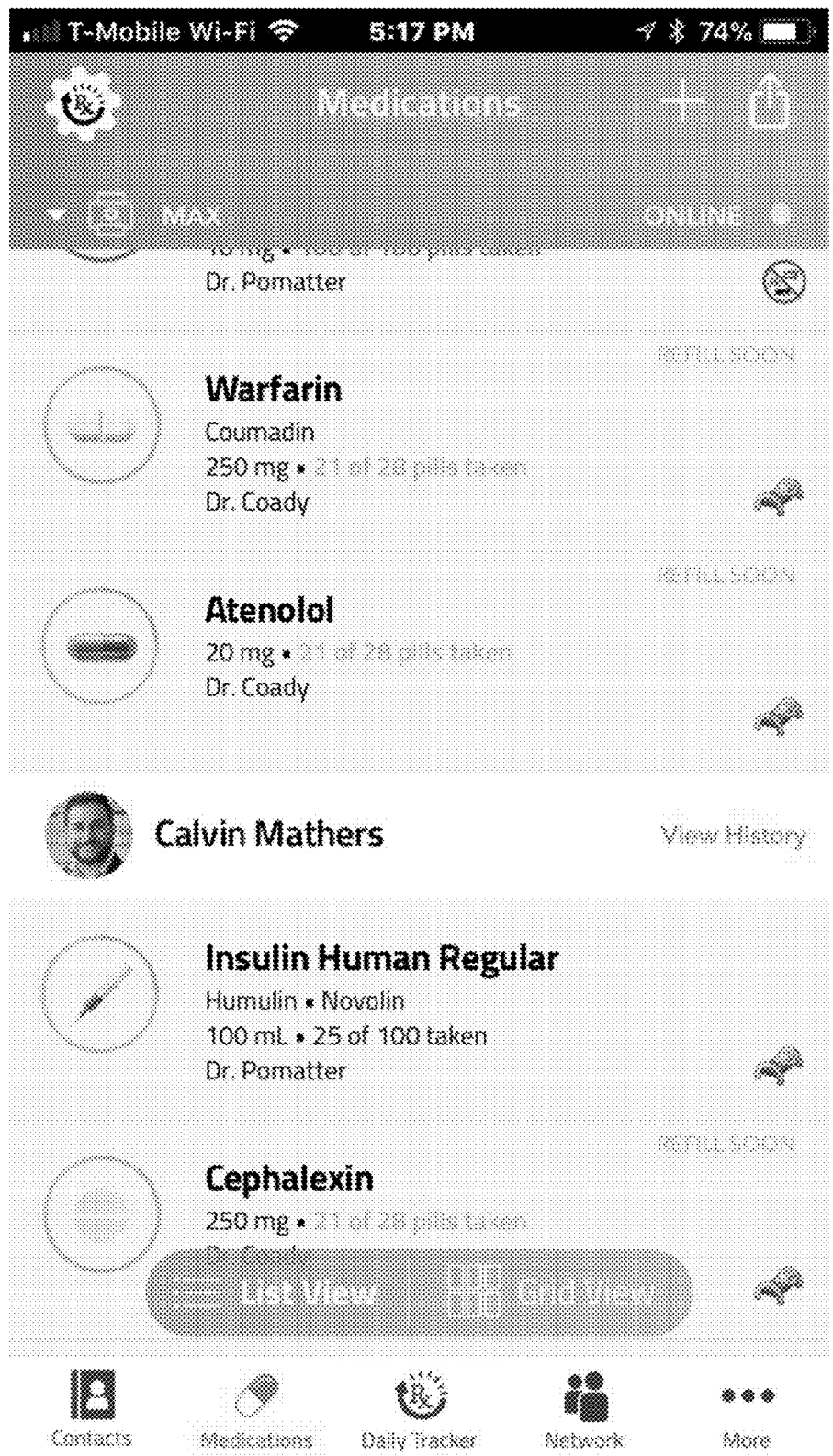
FIGS. 11A-11C show examples of user interfaces having a list view, a grid view, and another example of a grid view, respectively, that may be accessed by a user to view the various prescriptions or medication schedules stored into their profile or another user's profile, according to an aspect.
Figure 11B:
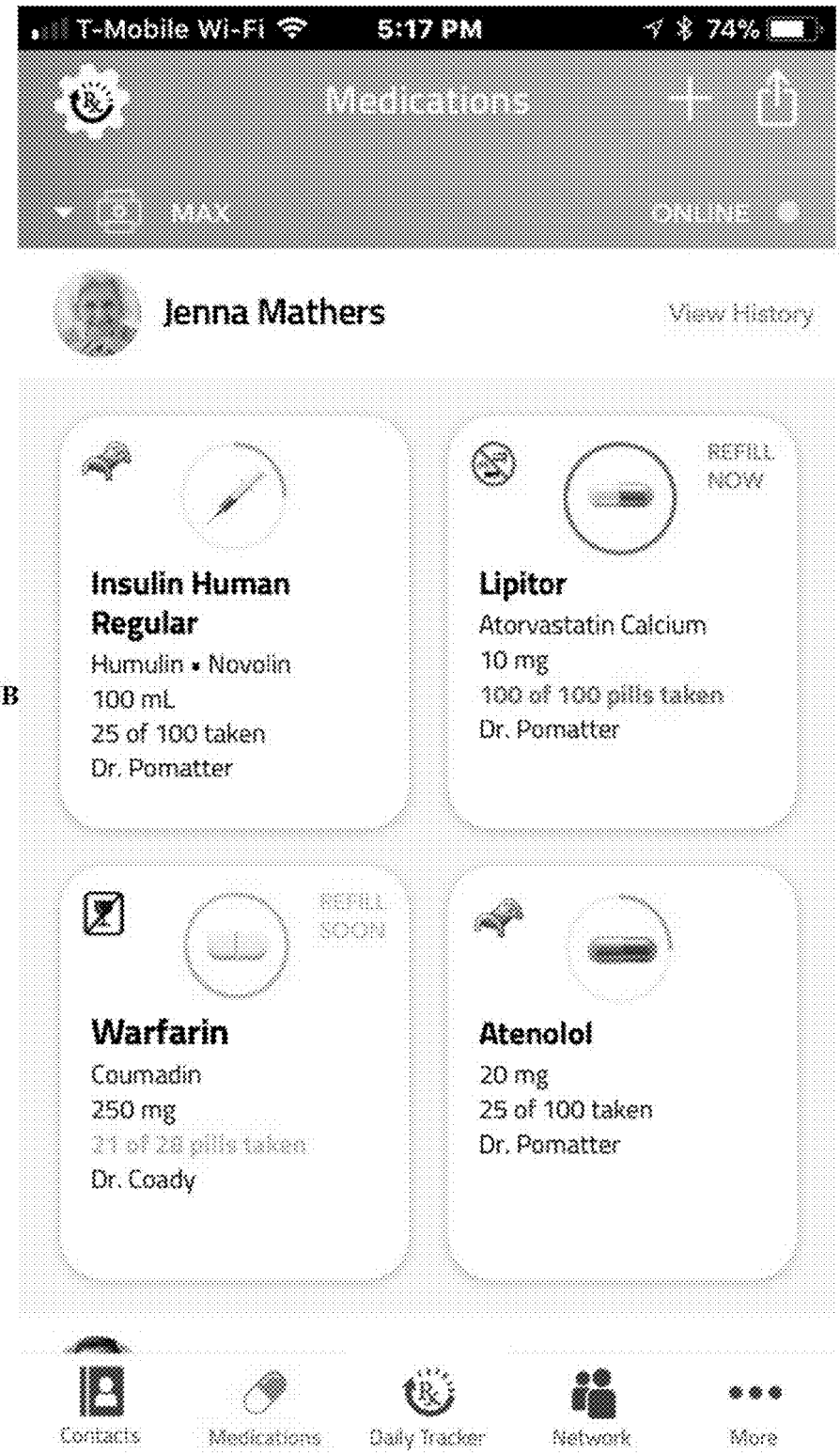
Figure 11C:
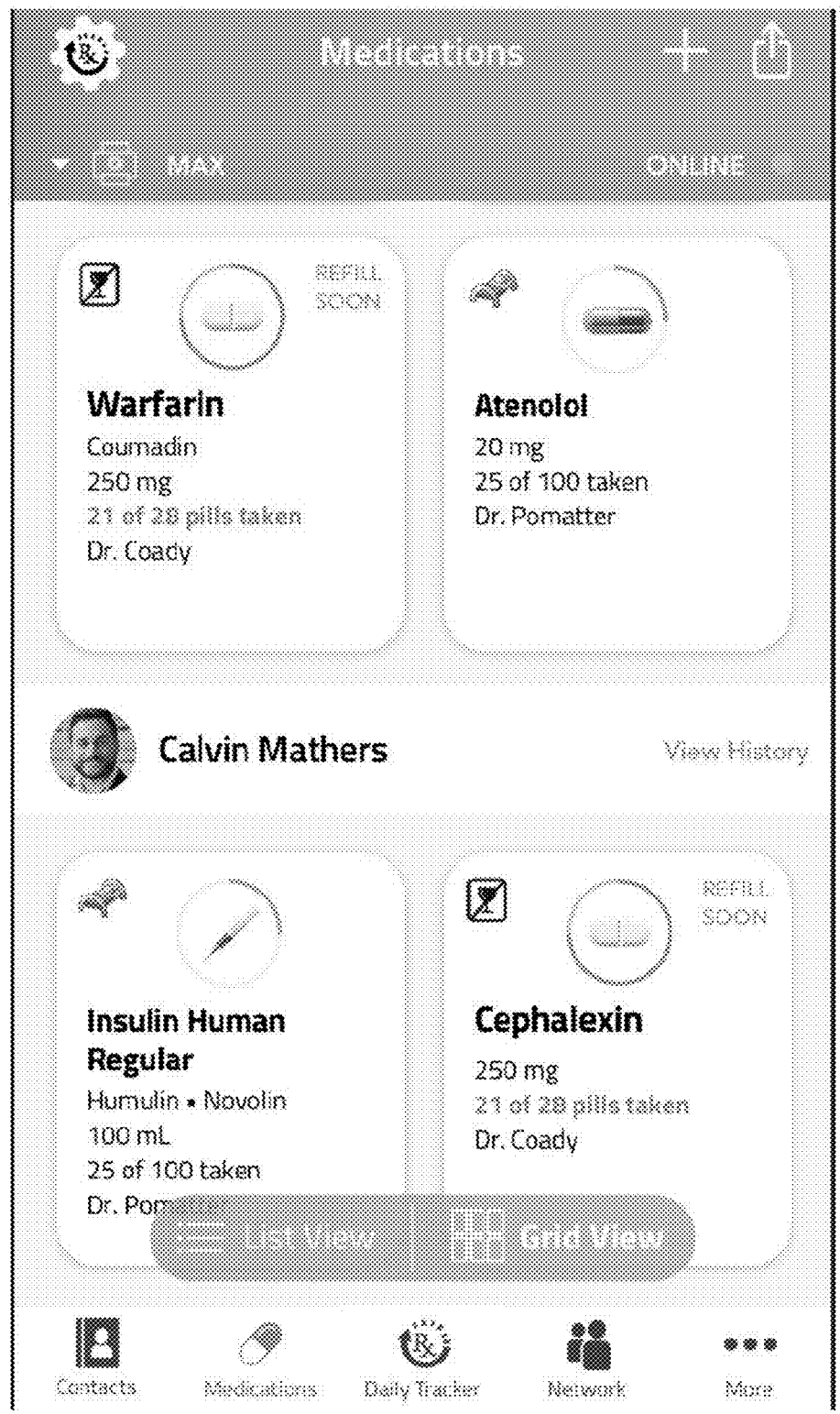

FIGS. 11A-11C show examples of user interfaces having a list view, a grid view, and another example of a grid view, respectively, that may be accessed by a user to view the various prescriptions or medication schedules stored into their profile (as shown in FIG. 11B) or another user's profile (as shown in FIG. 11C), according to an aspect. From the list or grid view, a user may select a particular medication or prescription schedule to view further information, as will be discussed when referring to FIGS. 12A-12C.

Figure 12A:
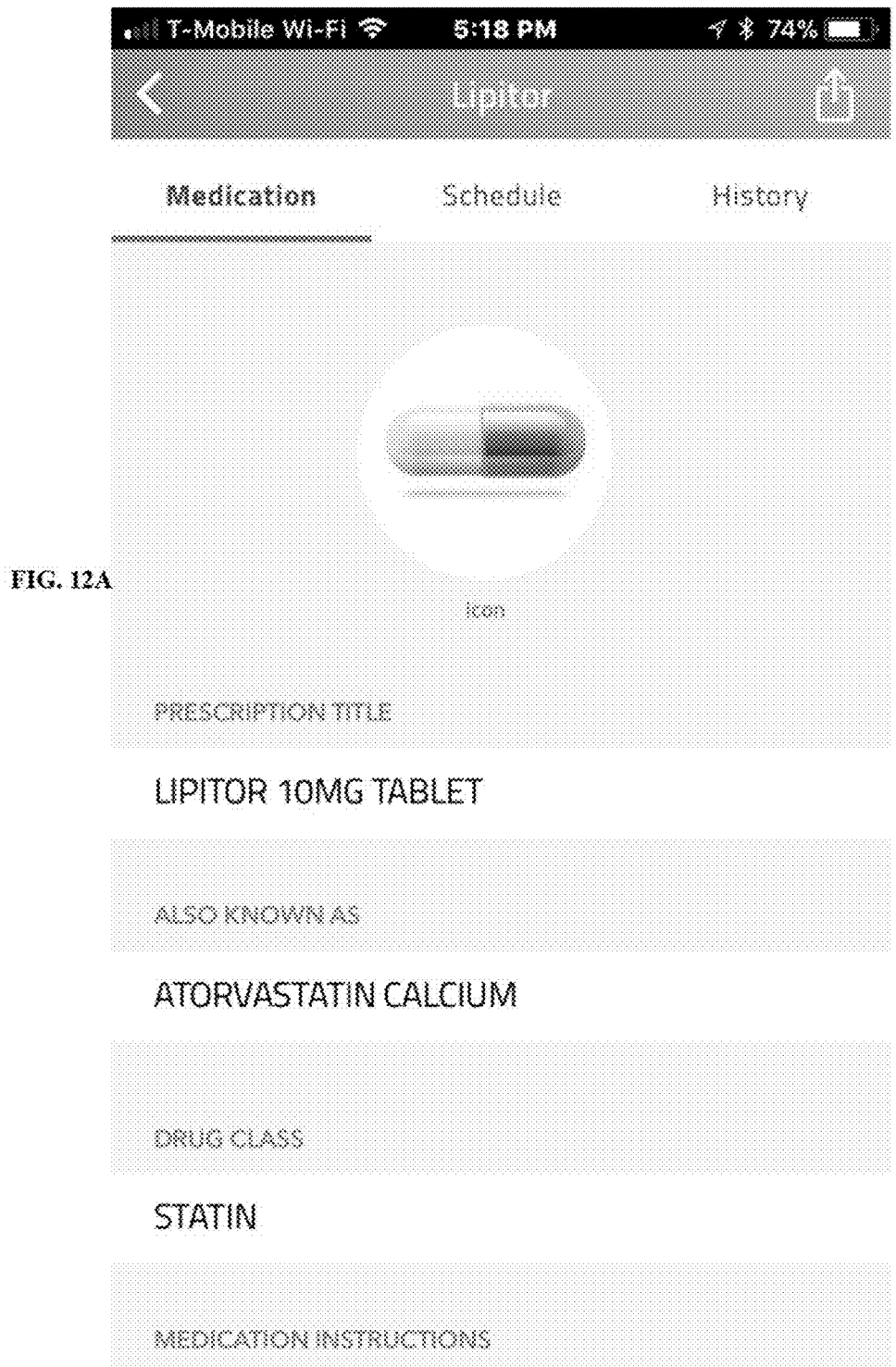
Figure 12B:
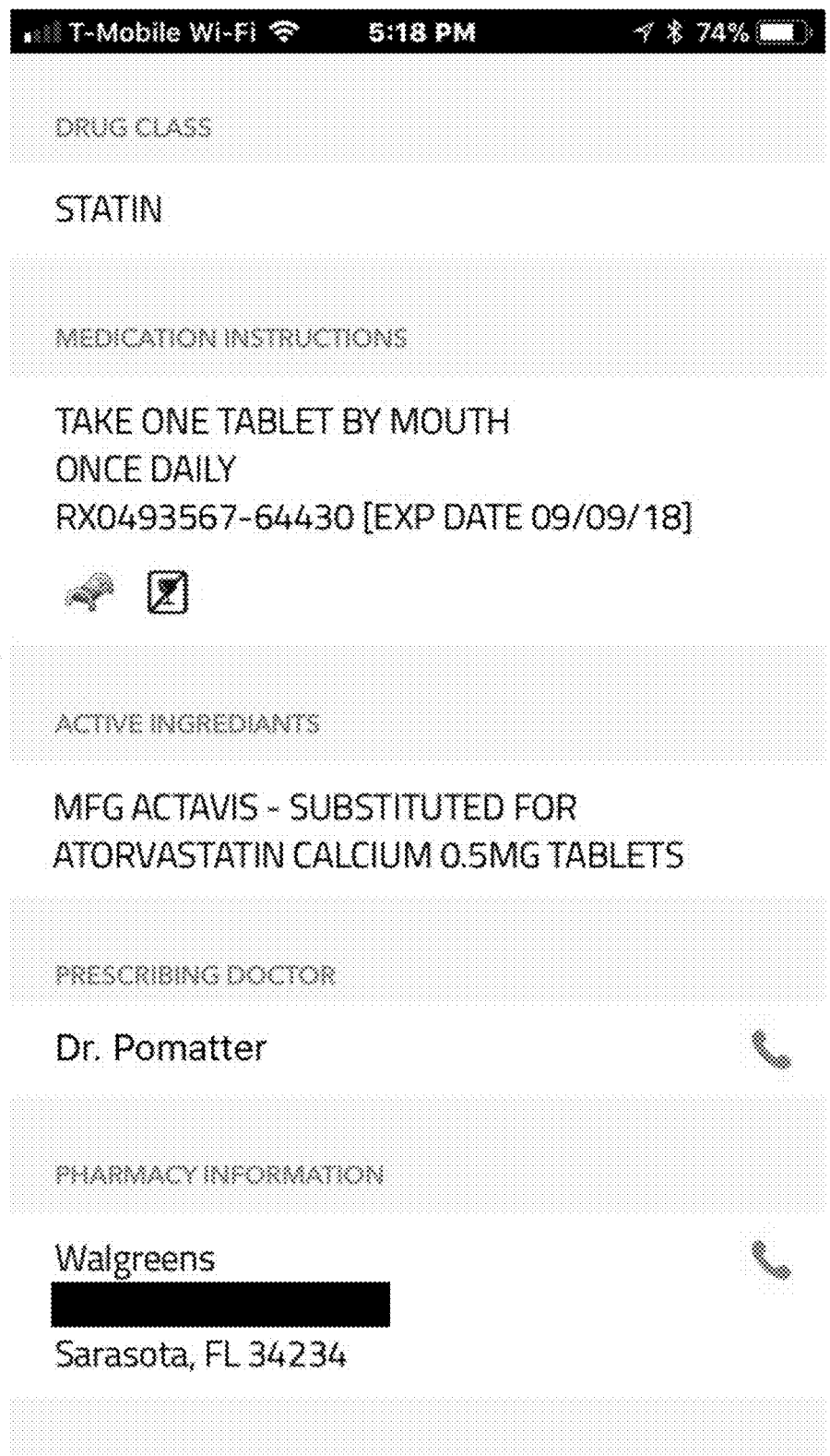

FIGS. 12A-12C show examples of user interfaces that may be accessed by a user when selecting a medication or prescription to view more information about the medication, according to an aspect. Exemplary information that may be provided to a user may include the type of medication, drug class, medication instructions, active ingredients, the prescribing doctor, pharmacy information, benefits and uses of the medication, side effects, and links to further reading.

Figure 13:
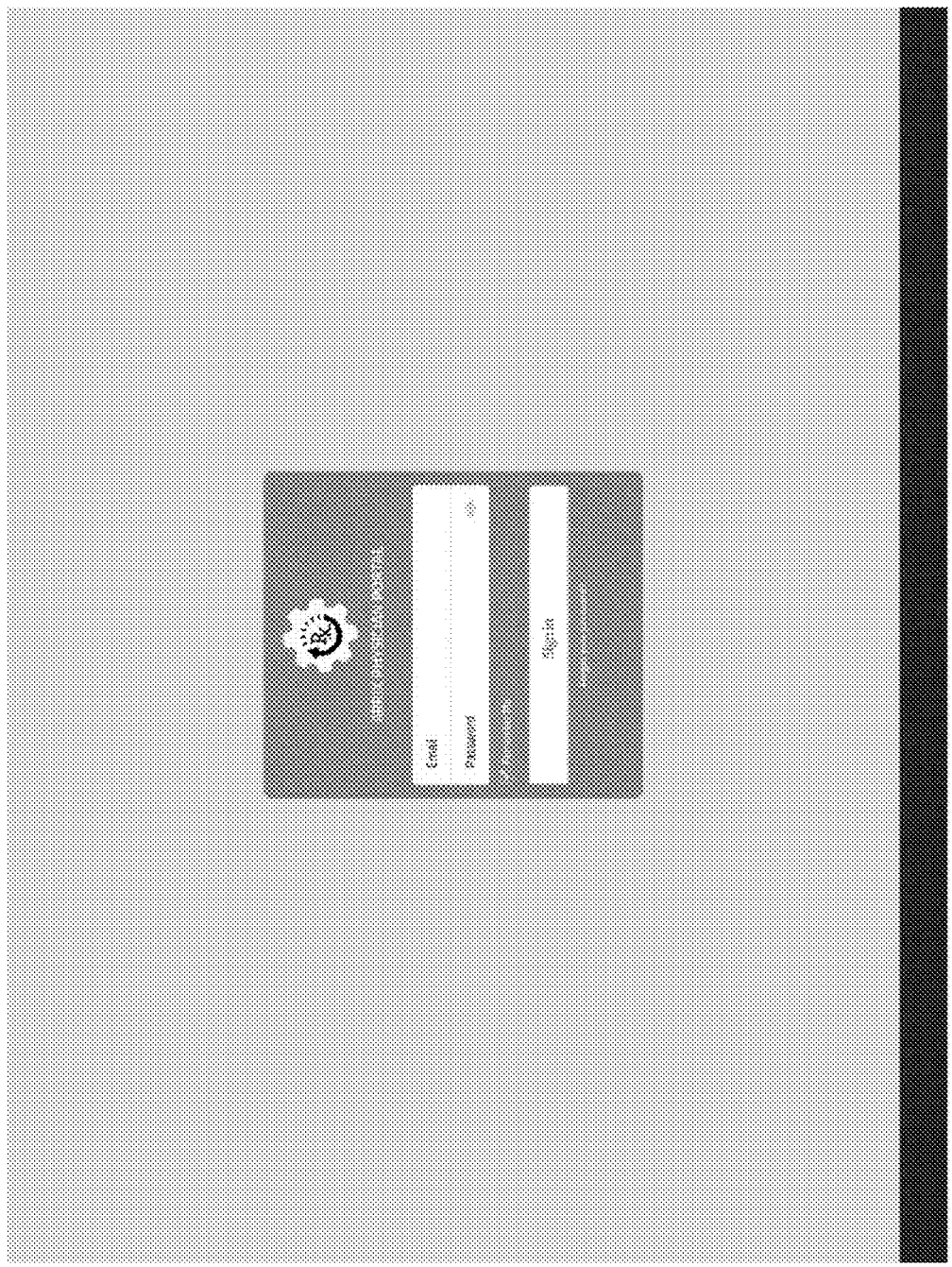
FIG. 13 shows an example of a user interface that may be accessed by a user to utilize a physician's portal of the medication management platform, according to an aspect.
Figure 14:
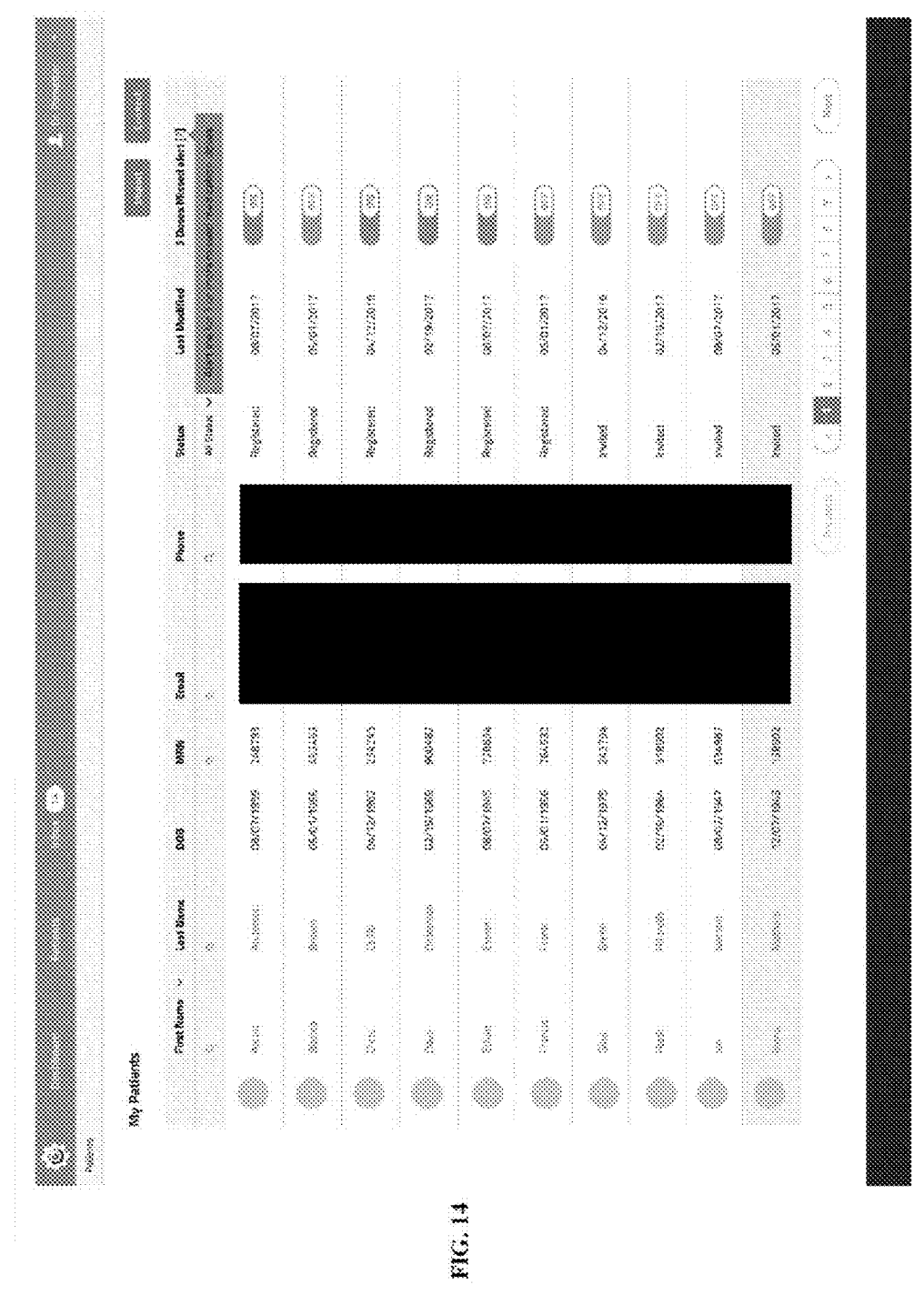

FIG. 13 shows an example of a user interface that may be accessed by a user to utilize a physician's portal of the medication management platform, according to an aspect. A doctor or physician may use the medication management platform to manage the prescriptions prescribed to their patients, for example. It should be understood that while the focus of FIGS. 13-18 is on accessing a physician's portal of the medication management platform through a web browser of a computer or similar electronic device, similar interfaces may be accessed and provided to the user if accessing the medication management platform through the tabletop dispenser as shown in FIGS. 7A-7C, or through a mobile application FIG. 14 shows an example of a user interface of a physician's portal of the medication management platform displaying a list of patients under a user's care, according to an aspect.

Figure 15A:
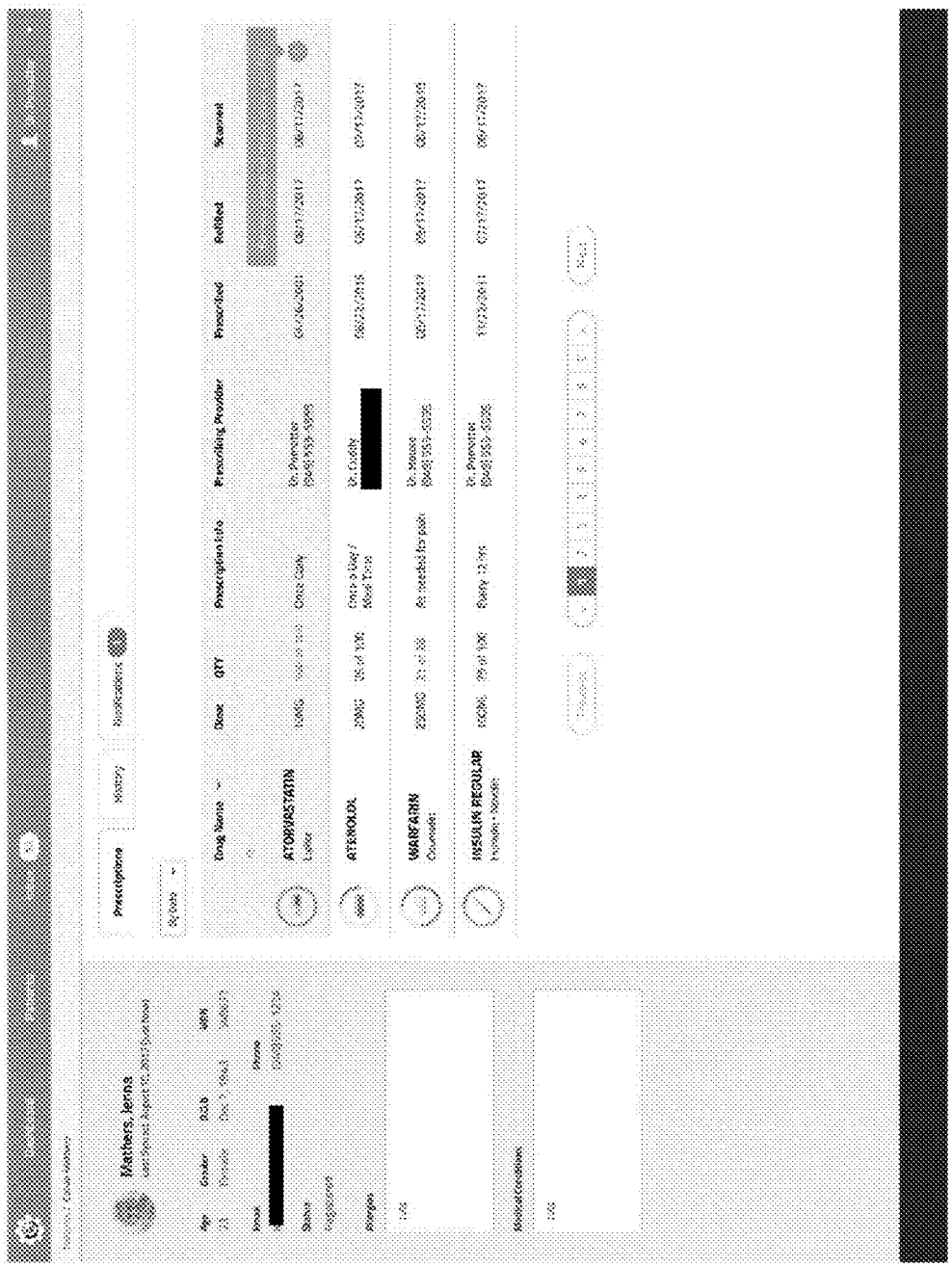
Figure 15B:
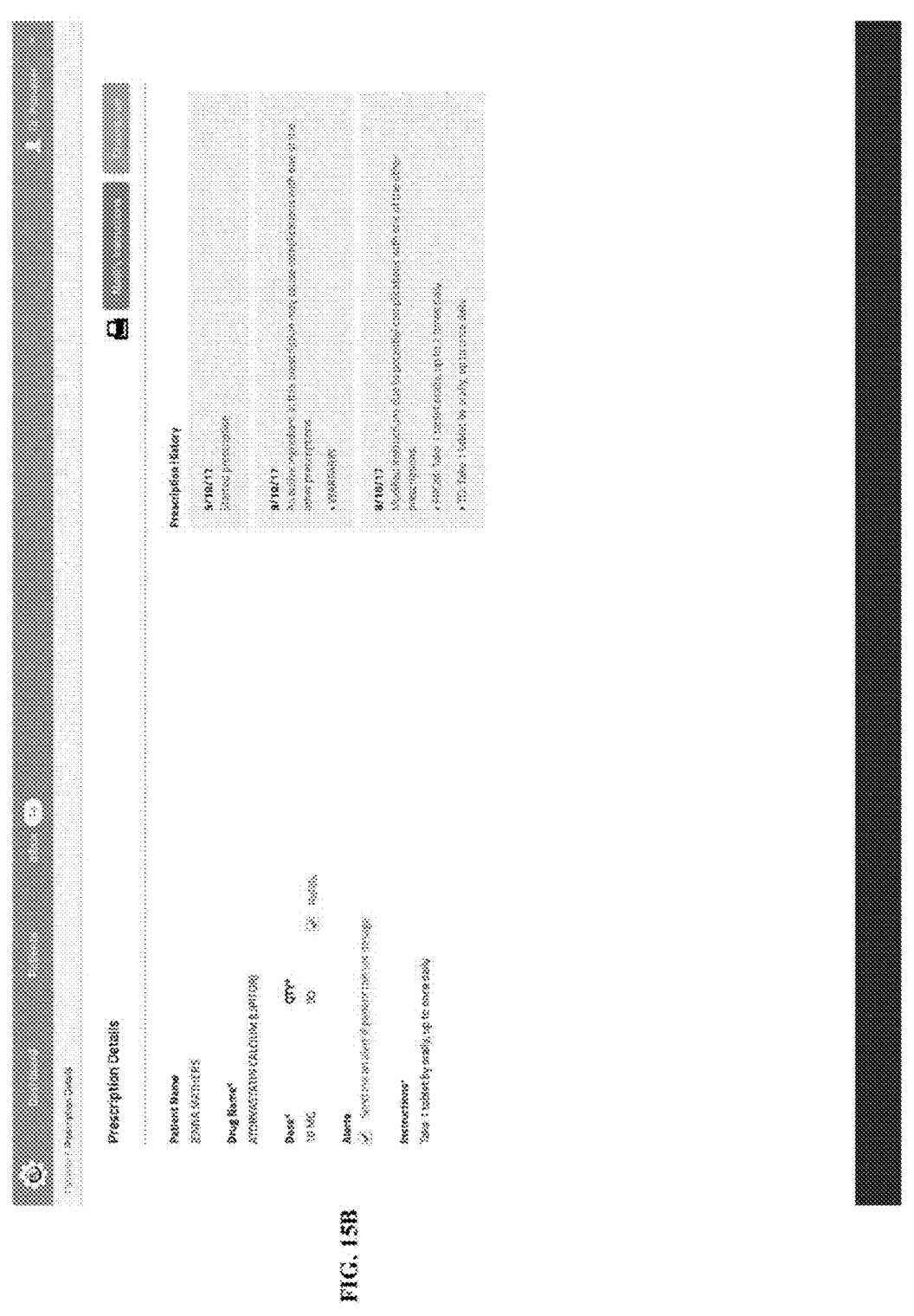

FIGS. 15A-15B show examples of user interfaces of a physician's portal of the medication management platform showing a detailed view of an individual patient under the user's care, according to an aspect.

Figure 16A:
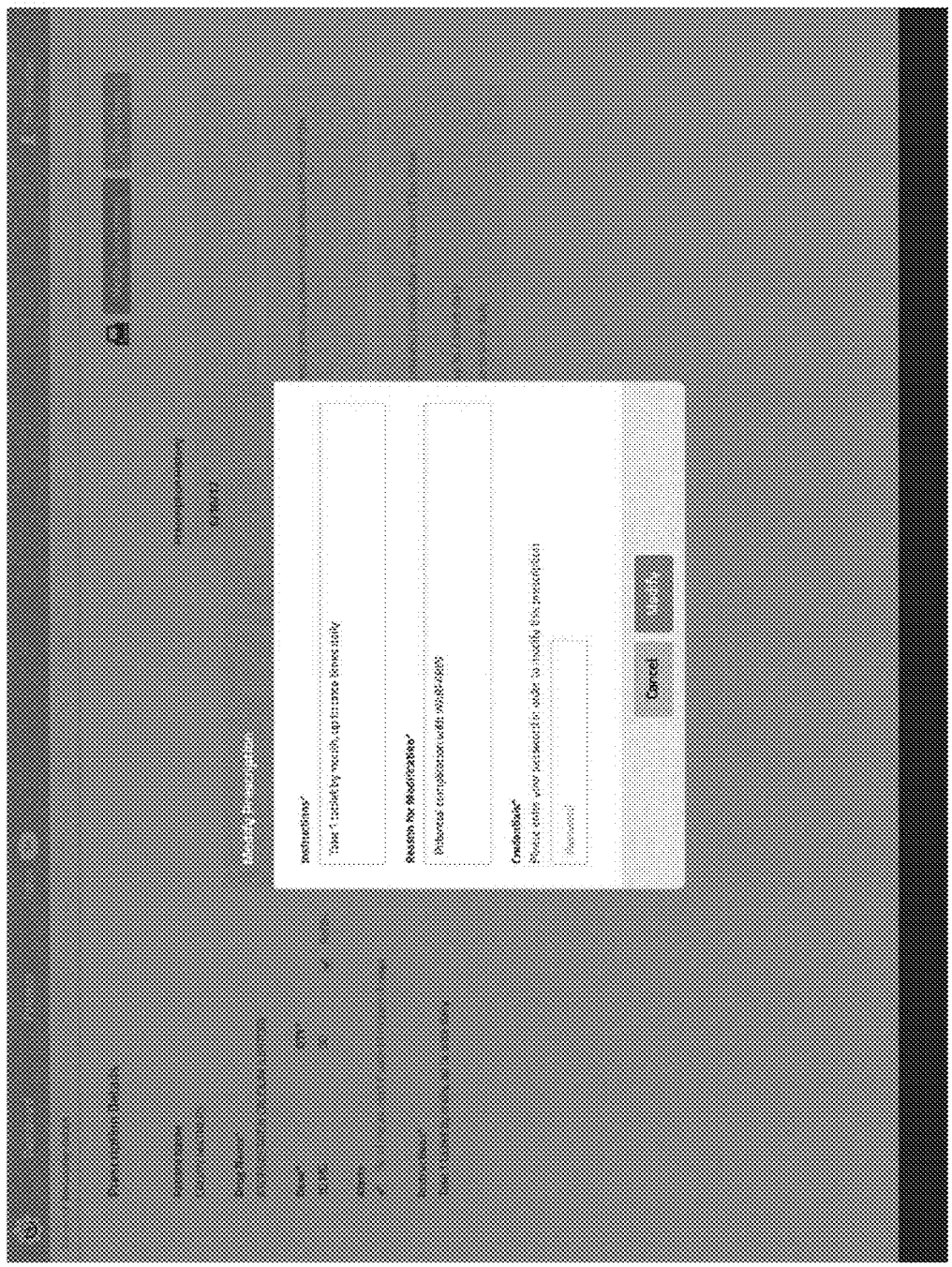
FIGS. 16A-16B show examples of user interfaces of a physician's portal of the medication management platform showing modifications that the user may make to a patient's prescription, according to an aspect.
Figure 16B:
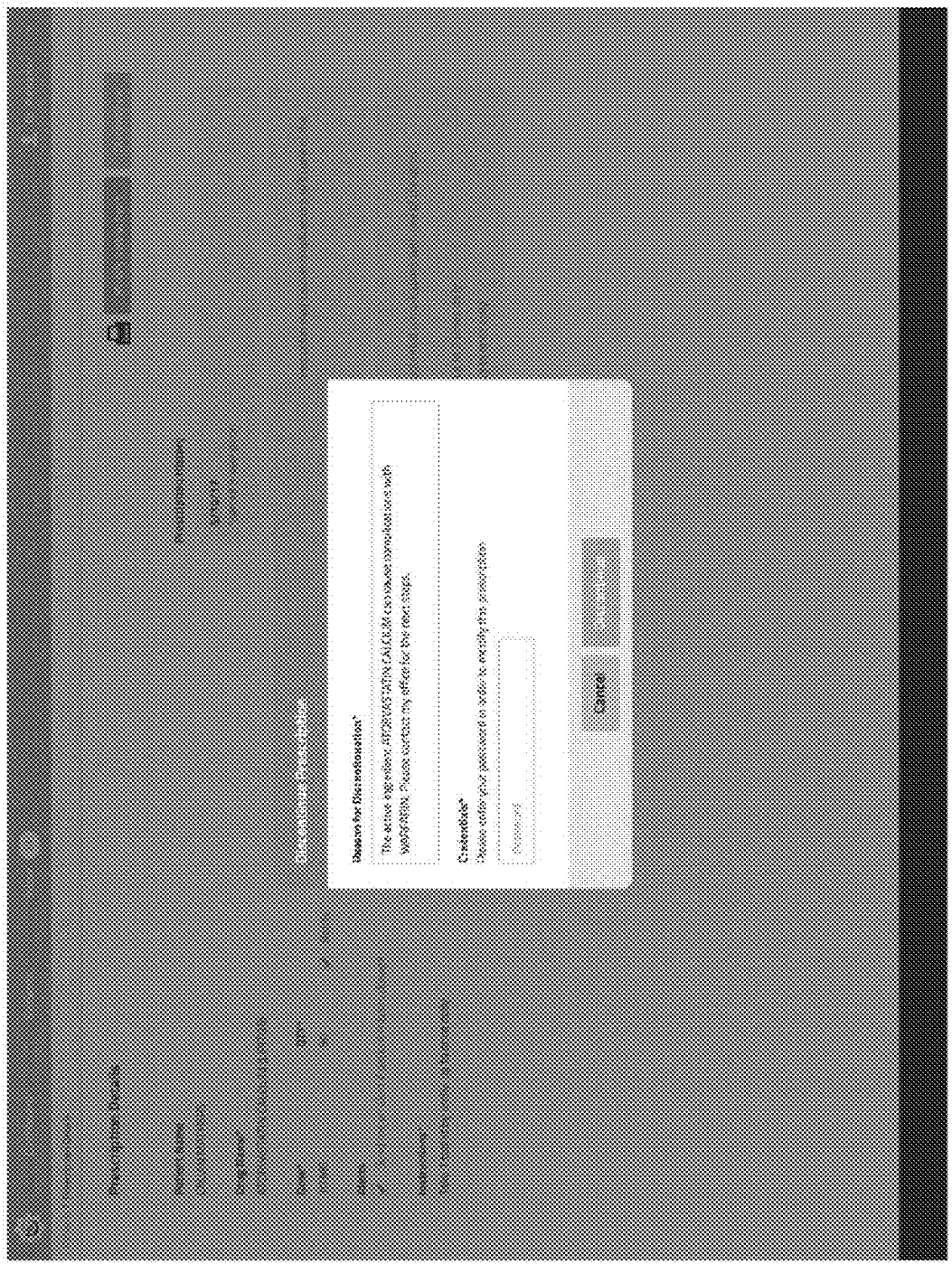

FIGS. 16A-16B show examples of user interfaces of a physician's portal of the medication management platform showing modifications that the user may make to a patient's prescription, according to an aspect. As an example, a doctor using the medication management platform may make changes to a prescription, or may discontinue a prescription. As an example, after discontinuation of a prescription, the tabletop and/or mobile devices may stop alerting or dispensing altogether of the medication, and may also prompt the user to discard the discontinued medication. The user may also include information related to the changes and may be required to provide credentials or authentication in order to make such changes. As another example, the medication management platform may be configured such that a physician cannot see a prescription unless a prescribed user has scanned the prescription into the system.

Figure 17A:
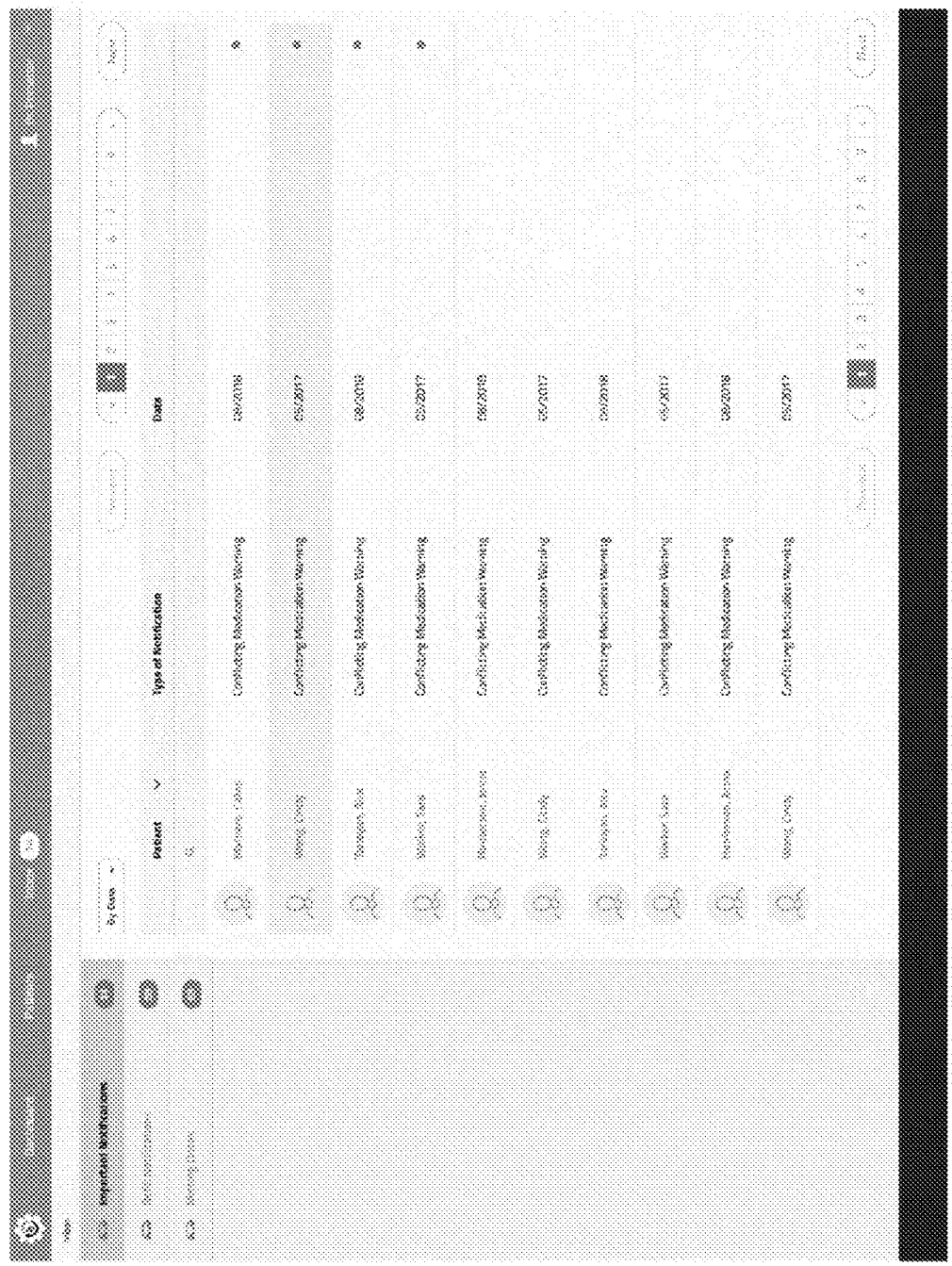
FIGS. 17A-17B show examples of user interfaces of a physician's portal of the medication management platform wherein a medication reconciliation view shows conflicting medication warnings and prescription details to the user, according to an aspect.
Figure 17B:
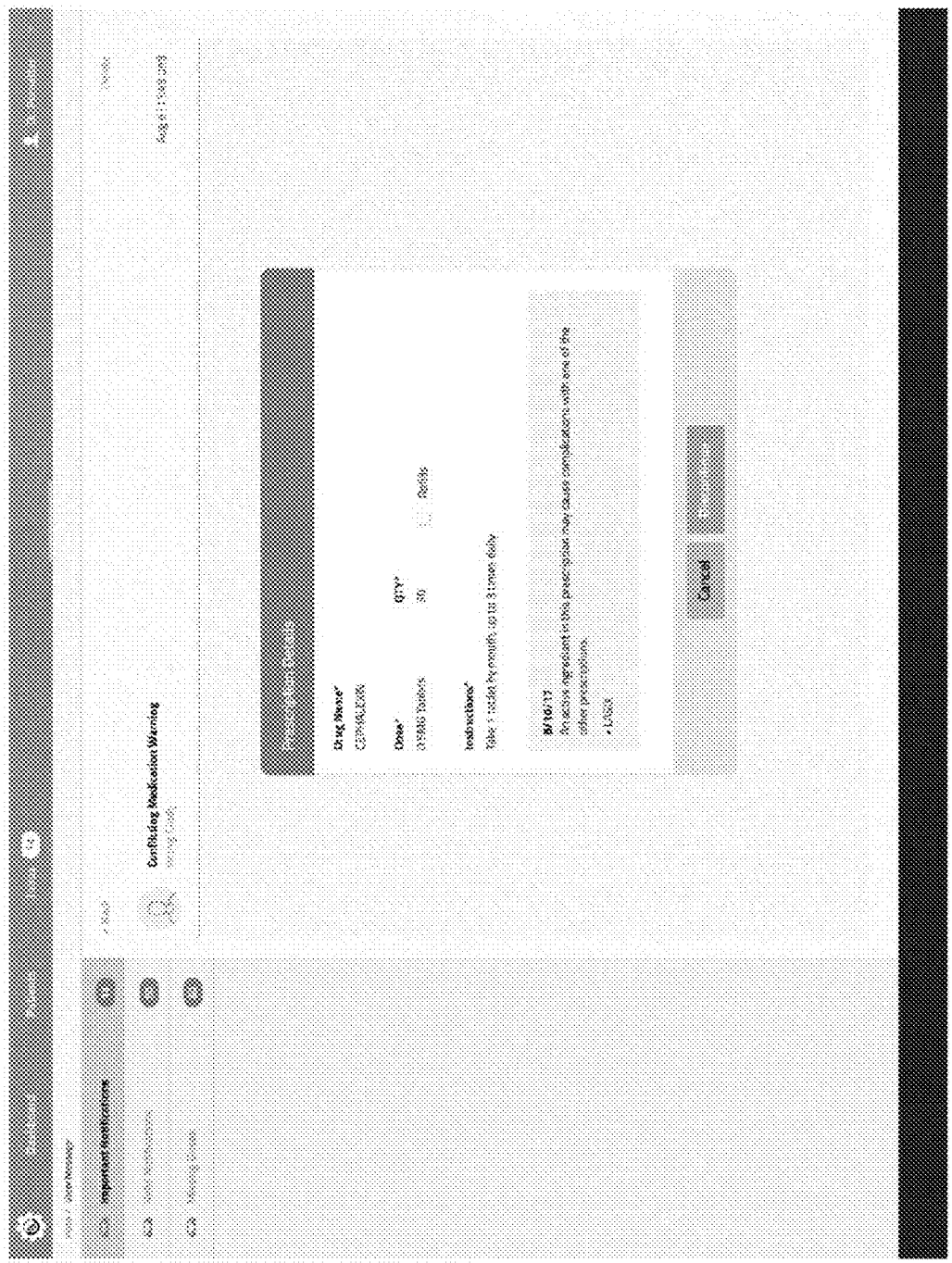

FIGS. 17A-17B show examples of user interfaces of a physician's portal of the medication management platform wherein a medication reconciliation view shows conflicting medication warnings and prescription details to the user, according to an aspect. The medication management platform may allow a user to easily view any conflicting medications before finalizing a prescription, for example. An advantage may be that the information about medication conflicts is easily accessible to the doctor prescribing the medication, and may make necessary changes quickly and efficiently. Another advantage may be that the physician may, as a user, track whether or not the patient is adhering to the physician's instructions.

Figure 18:
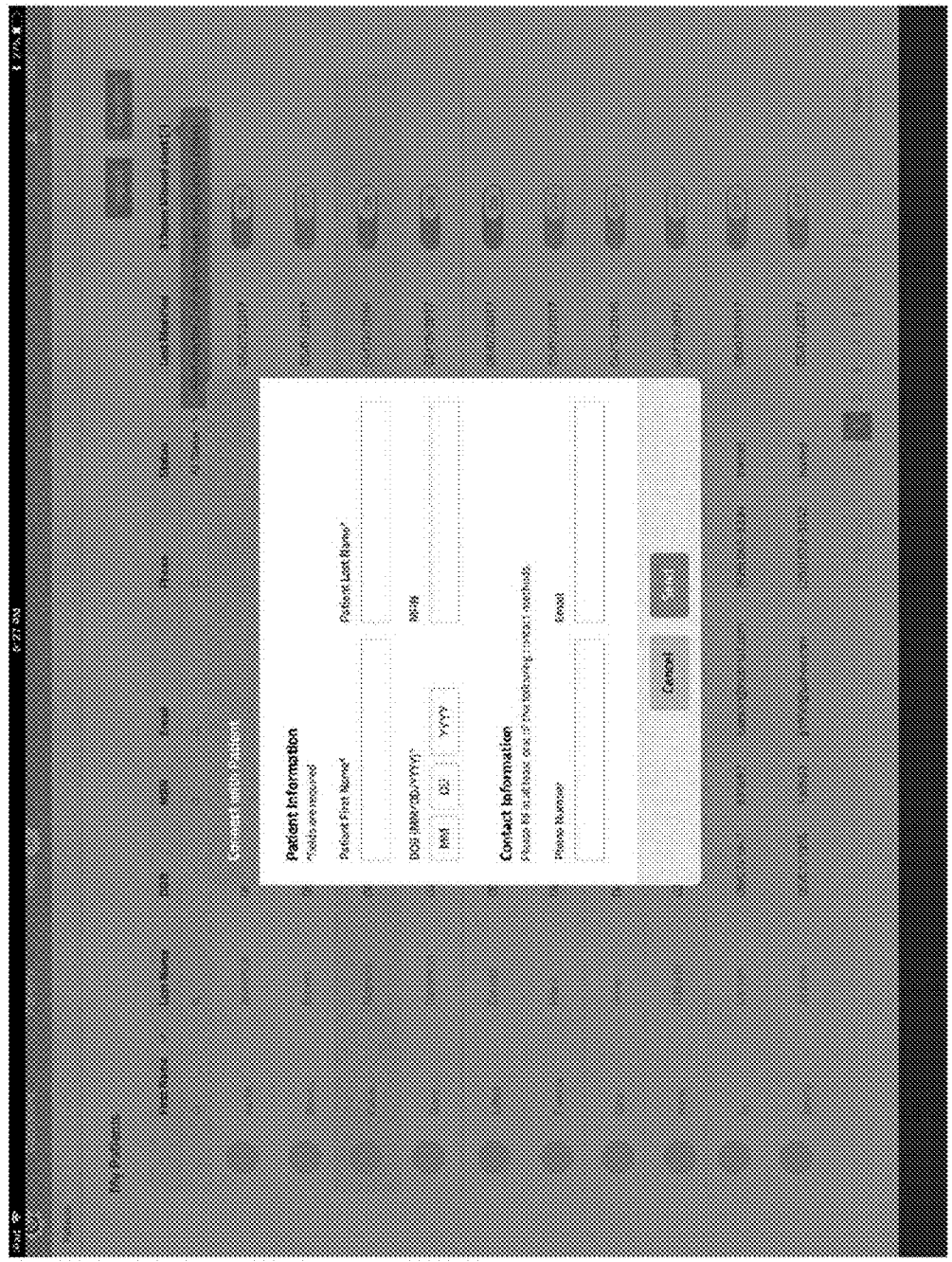
FIG. 18 shows an example of a user interface of a physician's portal of the medication management platform wherein a doctor can easily connect to a patient under their care, according to an aspect.

FIG. 18 shows an example of a user interface of a physician's portal of the medication management platform wherein a doctor can easily connect to a patient under their care, according to an aspect. An advantage may be that a doctor and patient may easily be in contact with one another through the medication management platform. For example, if a change to a patient's prescription must be made, a doctor can easily and quickly contact the patient. As another example, a patient that has questions or concerns about their prescription may quickly and easily contact their doctor. A patient may also similarly contact other users of the medication management platform for social support, for example.

Figure 19A:
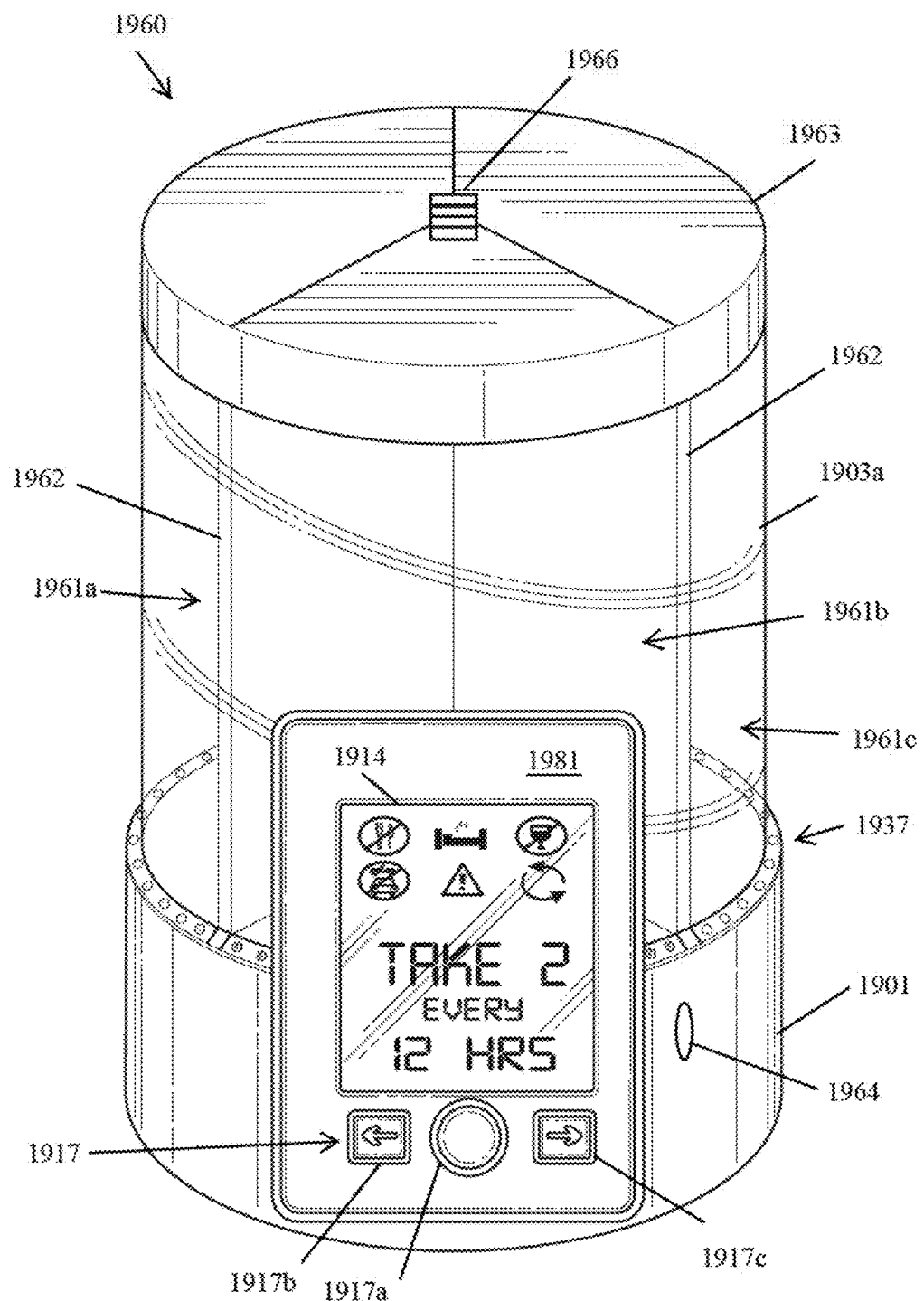
FIGS. 19A-19B illustrate a front, top perspective view, and a rear, top perspective view, respectively, of a compartmental medication dispensing apparatus, according to an aspect.
Figure 19B:
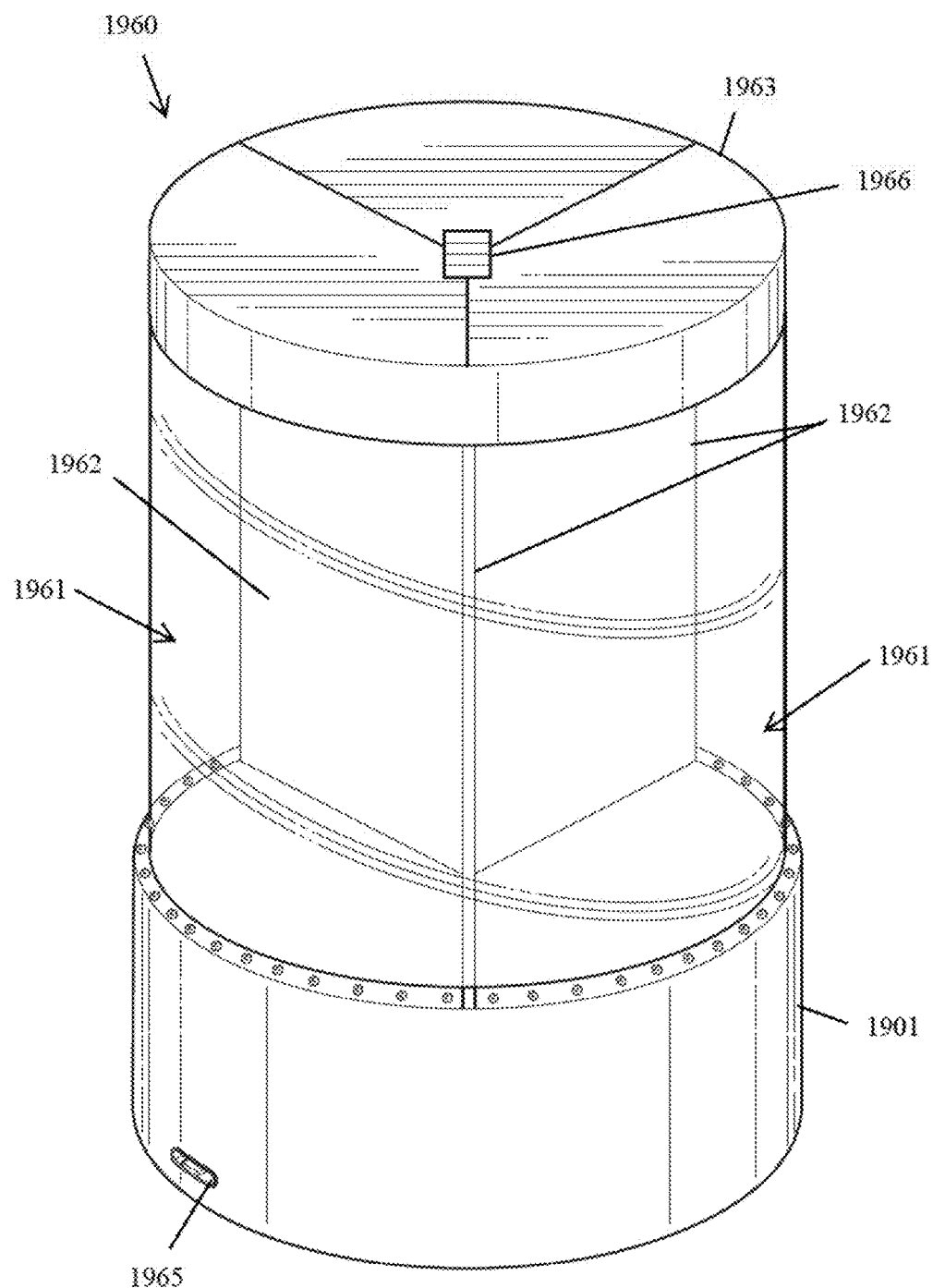

FIGS. 19A-19B illustrate a front, top perspective view, and a rear, top perspective view, respectively, of a compartmental medication dispensing apparatus ("compartmental medication dispensing apparatus," "compartmental dispenser," "compartmental medication dispenser" "compartmental medication delivery apparatus," "compartmental medication dispenser," "compartmental dispensing apparatus," or "compartmental apparatus") 1960, according to an aspect. The compartmental medication dispensing apparatus 1960 may be similar to the compact medication dispenser shown and described when referring to FIGS. 1A-6D, for example, and may include a plurality of compartments ("compartments," "pill sections," "sections," or "chambers") 1961 within, which may be interior spaces formed inside of the compartmental dispenser, such that a plurality of different medications may be stored in and dispensed from the various chambers 1961 of the compartmental dispenser. An advantage may be that a patient who requires or uses multiple kinds of medications may be able to store and carry all of their medications using only a single dispenser. As an example, an advantage of the compact dispenser shown and described when referring to FIGS. 1A-6D may be that a patient who only needs a single type of medication may not need any additional features used for managing multiple medications. The compartmental dispenser shown and described when referring to FIGS. 19A-26D may also be configured to connect to and work with a medication management platform, such as the platform shown and described when referring to FIGS. 8A-18.

As an example, three chambers are shown in FIG. 19A, where the three chambers or compartments are distinguished individually by 1961a, 1961b, and 1961c. Two of the three chambers of FIG. 19A are shown by 1961 in FIG. 19B, where two chambers are visible and a third chamber is not visible in this view. The chambers 1961 may be divided by walls ("walls" or "dividers") 1962. A compartmental dispenser 1960 having three chambers 1961 may thus have three walls 1962.

Similar to the compact dispenser shown and described when referring to FIGS. 1A-6D, the compartmental dispenser 1960 may be provided with a base 1901, a main body ("main body," "casing," or "medicine container") 1903a (which may be a glass casing similar to the glass casing shown by 103 in FIGS. 1A-1B), and lights 1937 (which may be LED lights, for example). The base 1901 may be cylindrical, and the lights 1937 may be provided at a top end of the base 1901, which may also receive the casing 1903a. The casing 1903a may also be cylindrical, and may function or act as a medicine container. Similar to the tabletop dispenser shown and described when referring to FIGS. 7A-7C, the compartmental dispenser 1960 may be provided with a screen 1914 and a control panel 1917, which may be provided together on a digital display monitor ("display monitor" or "display panel") 1981 on the base 1901. As shown as an example, the control panel 1917 may include a power button 1917a, a left button 1917b, and a right button 1917c. The base 1901 may also be provided with a speaker 1964, and a port 1965 (which may be a micro USB port, for example). The lights 1937 may be capable of providing a variety of different colors, which may signify different types of alerts or notifications to the user. It should also be understood that an alert notifying a user that they are schedule to take a medication may comprise blinking lights, auditory noise from the speaker, visual cues from the screen 1914, and so on.

The screen 1914 may provide the following exemplary warnings, alerts, and notifications: drug-to-drug interactions, drug and allergy alerts, low battery, a time zone change, and notices about syncing, pairing, or connecting to an electronic or mobile device. These alerts may be accompanied by flashing or steady lights from the lights 1937, for example, or an auditory alert from the speaker 1964.

The compact dispenser may also be provided with a sliding door cap ("sliding door cap," "sliding cap," or "door cap") 1963, which may be provided on the top end of the glass casing 1903. The sliding door cap 1963 may provide a closure for the compartmental dispenser 1960, which may be opened by a user to access medication, and may be closed by the user such that the medication stored inside is sealed. The door cap 1963 may be rotatable in a clockwise or counterclockwise direction on top of the casing 1903a, such that the sliding door (shown in further detail in FIGS. 25A-25D) may be positioned over any chamber of the compartmental dispenser 1960. The rotation of the sliding door cap 1963 may be performed manually, or may be automatically performed by the compartmental dispenser 1960. The door cap 1963 may be provided with a slider 1966 which may be used as a handle, and used to open and close the sliding door. In FIGS. 19A-19B, the sliding door 1967 of the sliding door cap 1963 is shown in a closed state, and thus, the slider 1966 is shown at the center of the door cap 1963.

Figure 20:
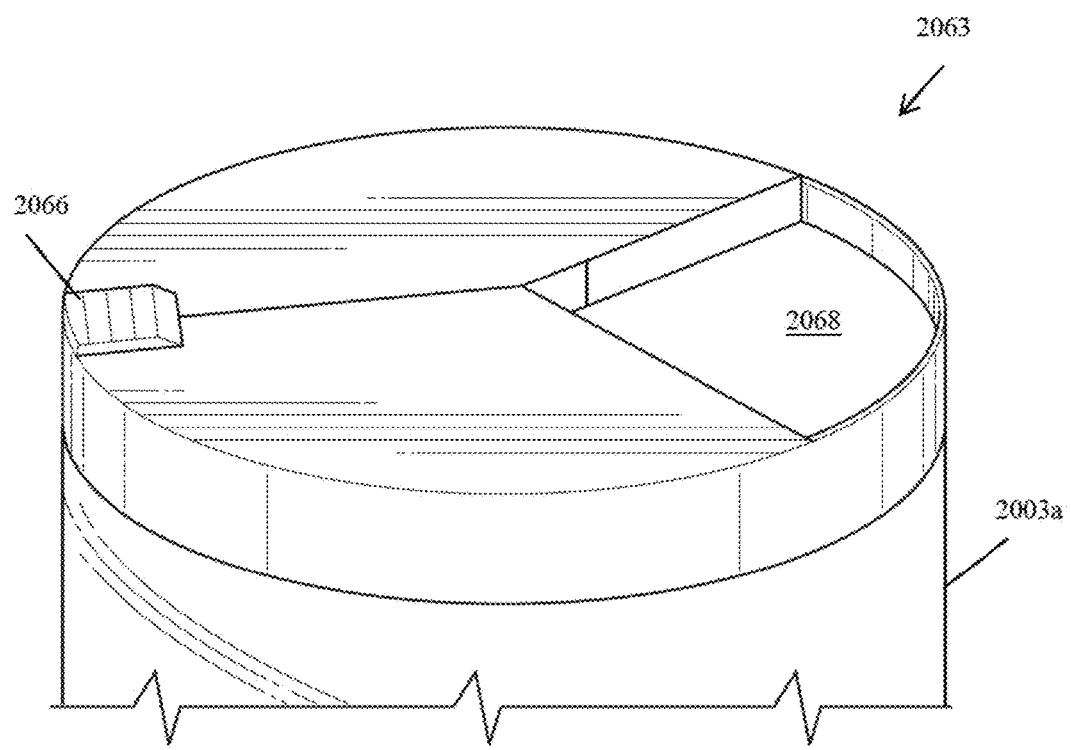
FIG. 20 illustrates the side perspective view of the sliding door cap with the sliding door in an open state and thus not visible, according to an aspect.

FIG. 20 illustrates the side perspective view of the sliding door cap 2063 with the sliding door in an open state and thus not visible, according to an aspect. The sliding door cap 2063 is shown in this view on a partially shown casing 2003a. As an example, when the sliding door (as shown by 1967 in FIGS. 19A-19B) is in an open state such that an opening 2068 is created, the sliding door may be completely underneath the other portions of the door cap 2063 and thus not visible. When the sliding door is in an open state, the slider 2066 may be at an edge of the door cap 2063.

Figure 21A:
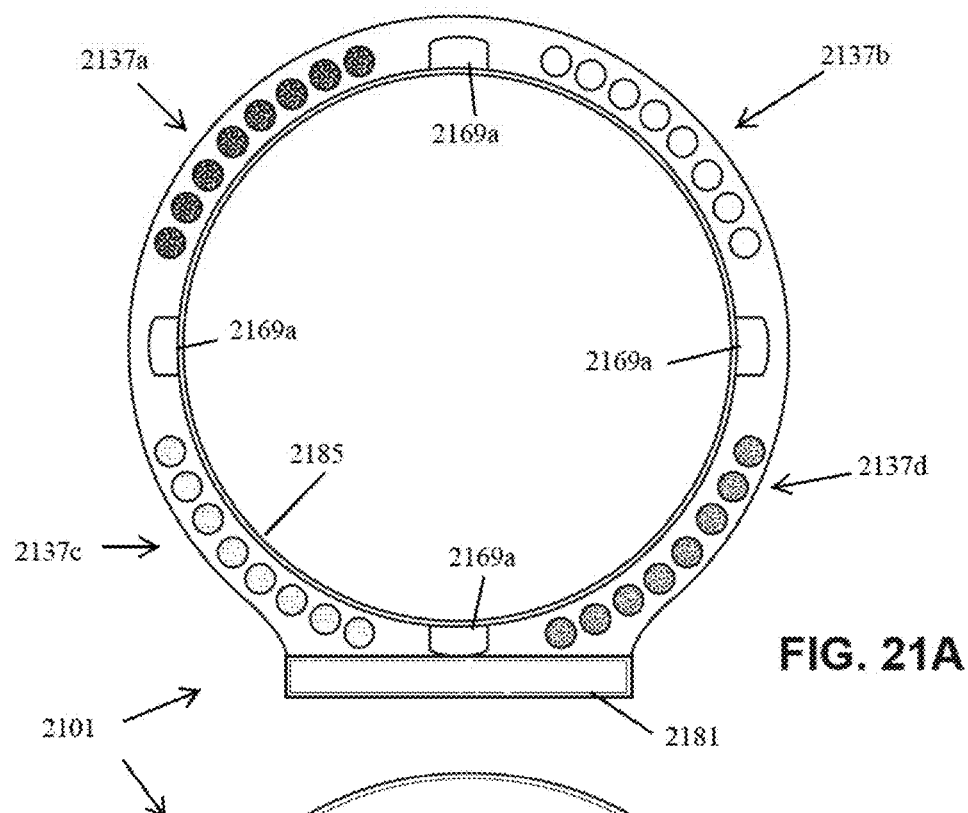
FIGS. 21A-21D illustrate the top plan view, the bottom plan view, the front elevation view, and the rear elevation view, respectively, of the base, according to an aspect.
Figure 21B:
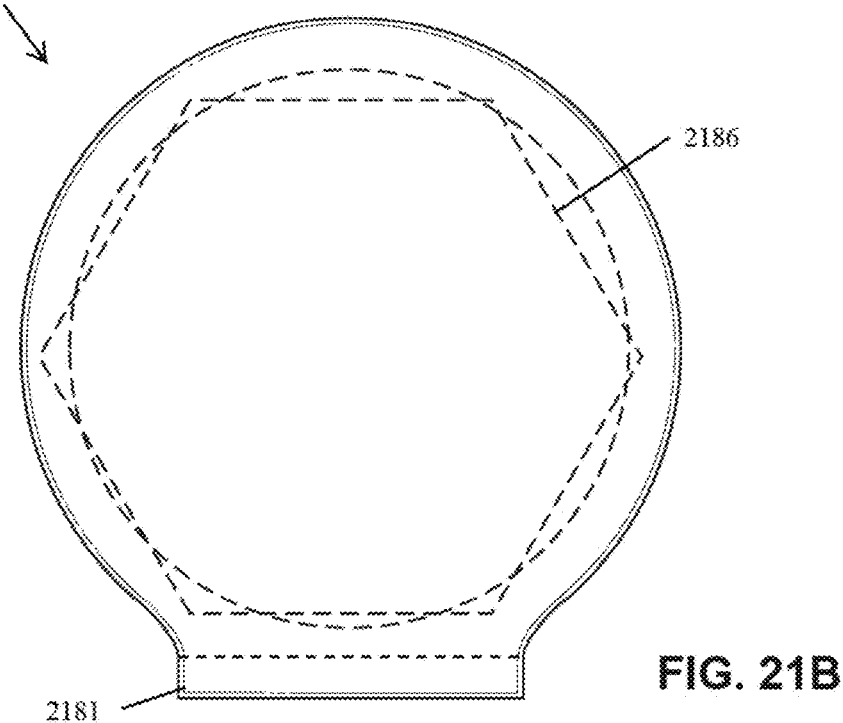
Figure 21C:
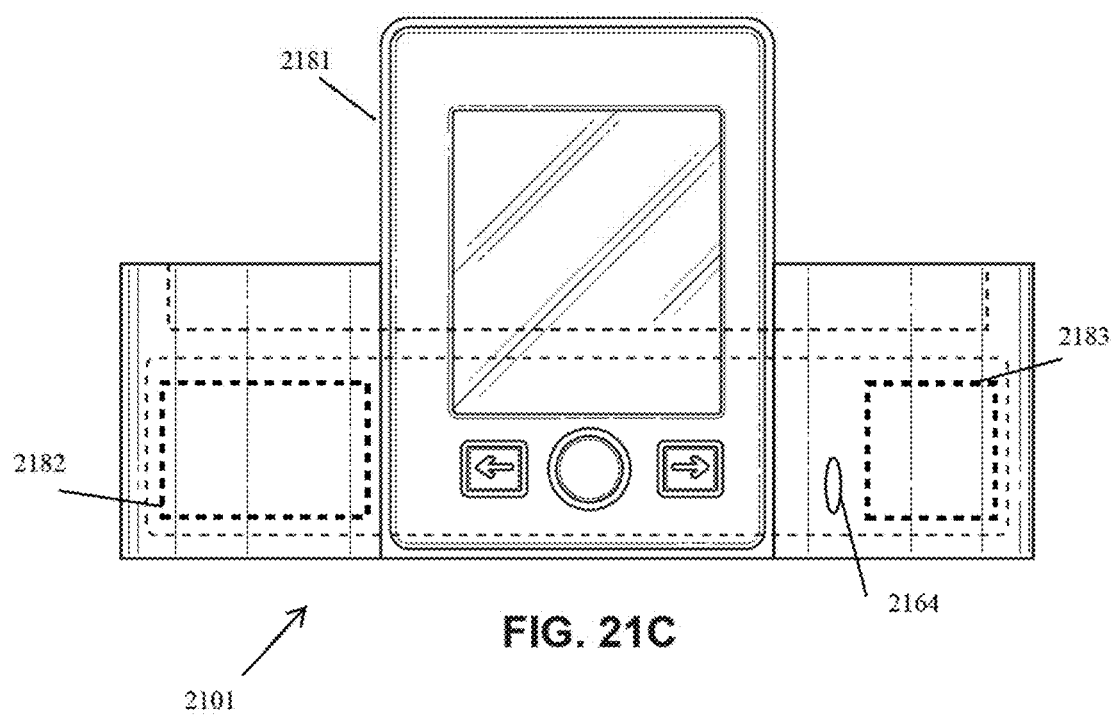
Figure 21D:
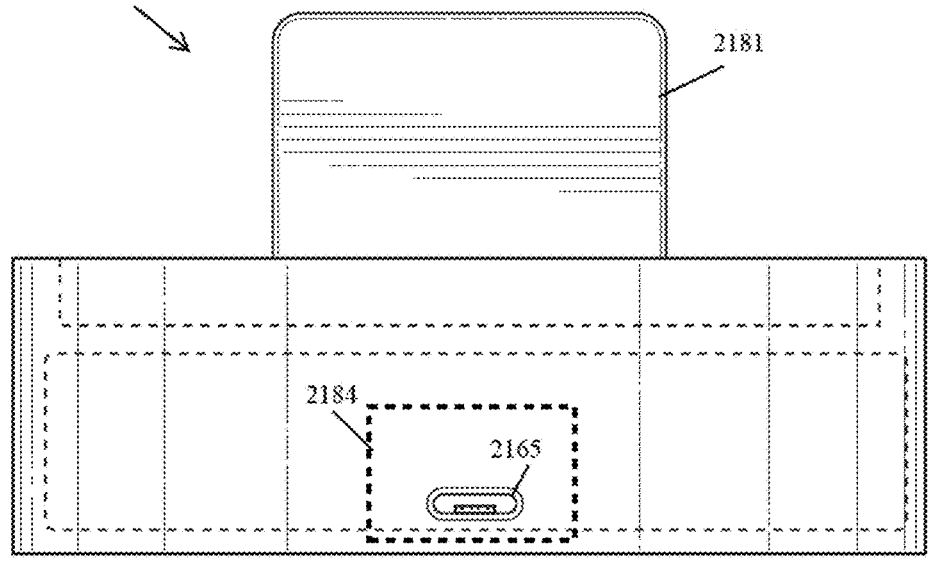

FIGS. 21A-21D illustrate the top plan view, the bottom plan view, the front elevation view, and the rear elevation view, respectively, of the base 2101, according to an aspect. The base 2101 may be provided with a digital display monitor 2181, a speaker 2164, a port 2165, magnets (which may be locking magnets having a particular shape, as will be discussed further herein) 2169a, and lights, which may be grouped into sets, as an example. FIG. 21A shows an example of lights that are provided in four groups, shown by 2137a-2137d. As an example, a medicine container having four compartments may be used with the base 2101 shown in FIG. 21A, such that each individual compartment is paired with one of the four groups 2137a-2137d, and such that the lights corresponding to a compartment may light up or blink to alert or notify the user about their medication. Each light group 2137a-2137d may be provided with a different or unique color of light. The lights of light groups 2137a-2137d may be capable of providing a variety of different colors, which may signify different types of alerts or notifications to the user, or signify different medications. As an example, the lights of the light groups 2137a-2137d may provide a white light color to show that the corresponding pill section is not being used. Other suitable colors and meaning associated with the colors may also be used.

As shown in the top view of FIG. 21A, the base 2101 may be provided with a locking channel 2185, which may receive the medicine container (shown by 1903a in FIG. 19A). When the medicine container is received into the locking channel 2185, the locking magnets 2169a may also help to lock the medicine container in place, with the medicine container having corresponding elements (shown in further detail in FIGS. 22A-22B). As an example, the magnets 2169 may be copper metal electrical plates.

The bottom of the base 2101 may be provided with a sensor or any other suitable measuring means 2186 (not visible in this view, and represented by broken lines). The sensor or measuring means 2186 may, for example, be a weighted pendulum, a tilt circuit capable of detecting changes in the tilt of the dispenser, a sensor capable of detecting changes in weight, or any other suitable means for measuring, recording, and comparing the weight or orientation of the contents of a medicine container, for example.

The base 2101 may also house a circuit board 2182, a computer memory and/or processor 2183, and a battery 2184, which may be housed within the interior of the base and thus not be visible in the views shown FIGS. 21A-21D. Thus, the locations of these elements are represented in broken lines. The battery 2184 may be associated with the port 2165, which may provide power to and thus charge the battery 2184. The compartmental dispenser may also have power provided to it by any other suitable means.

Figure 22A:
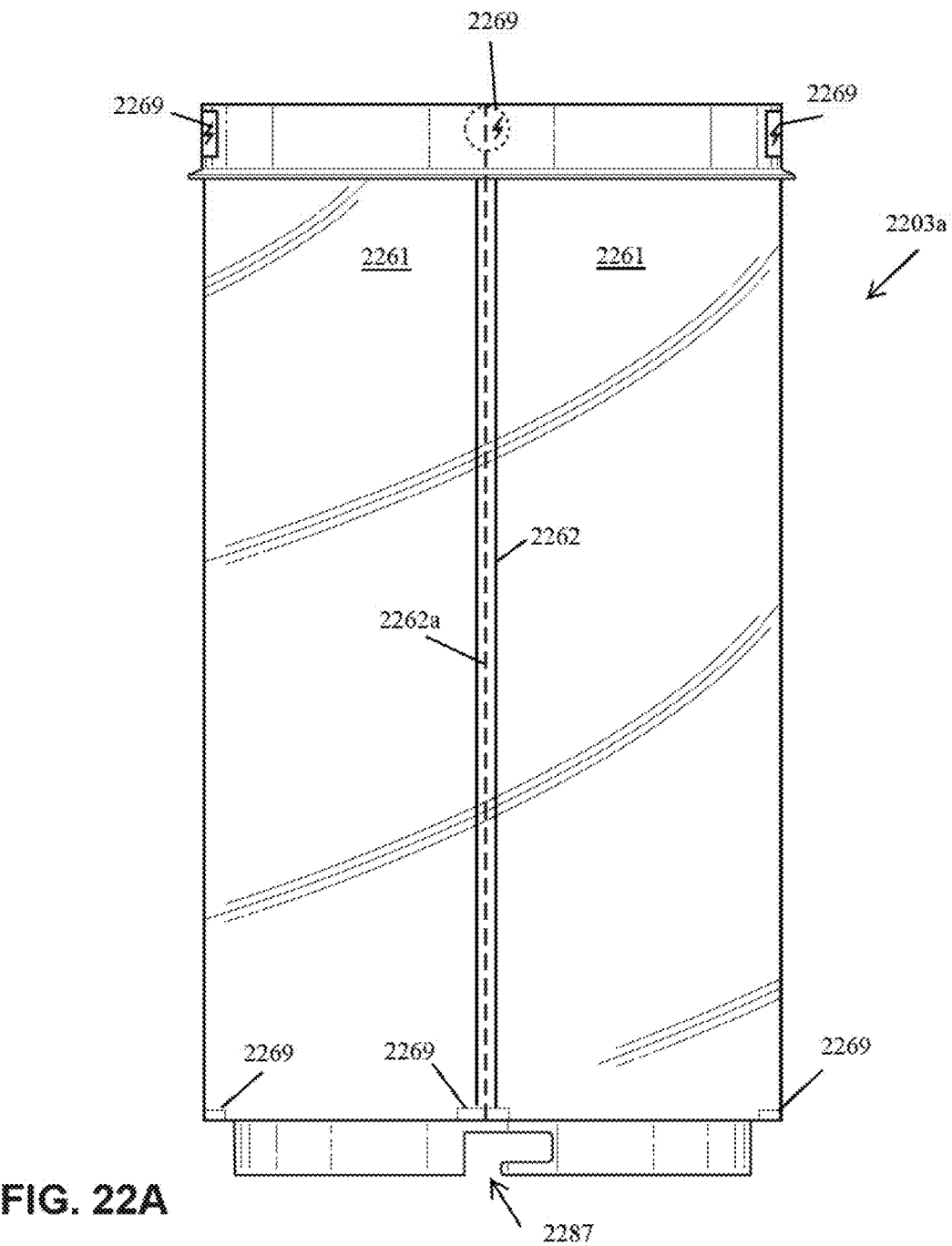
FIGS. 22A-22C illustrate the side elevation view, the top plan view, and the bottom plan view, respectively, of the casing, according to an aspect.
Figure 22B:
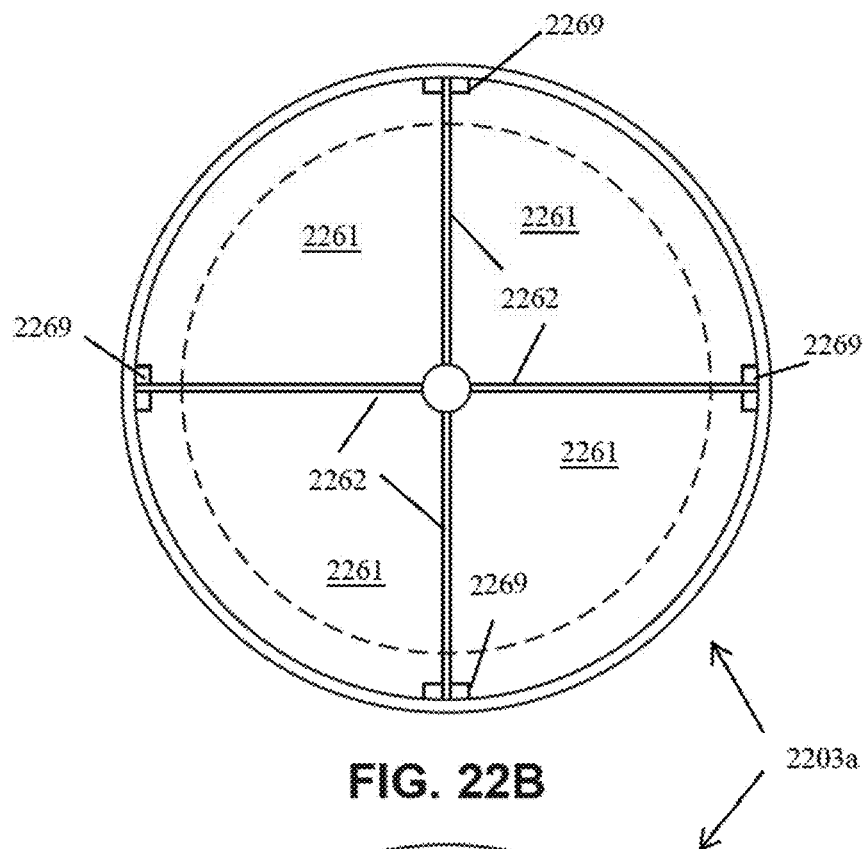
Figure 22C:
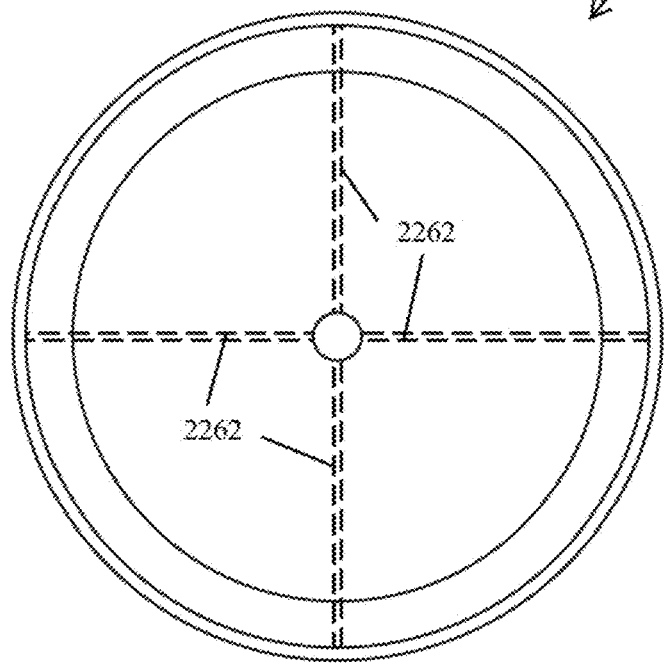

FIGS. 22A-22C illustrate the side elevation view, the top plan view, and the bottom plan view, respectively, of the casing 2203a, according to an aspect. For visual clarity, the casing 2203a is shown separated from the base (as shown by 1901 in FIGS. 19A-19B) and the sliding door cap (as shown by 1963 in FIGS. 19A-19B). The casing 2203a may be a medicine container and may hold medications within it. The casing 2203a may be provided with walls 2263, which may form a plurality of interior spaces, which may be individual compartments 2261. Individual compartments 2261 may separate different types of medication within the casing 2203a. A casing 2203a having four compartments 2261 is shown as an example in FIGS. 22B-22C. However, it should be understood that a casing 2203a may have any suitable number of compartments, such that a user may be able to carry any number of medication types or pill types within a single compartmental dispenser. Each wall 2262 may have a copper metal wire (represented by a broken line) 2262a or any other suitable connector or conductor embedded within the wall, such that the wire can conduct a magnetic circuit between the base, the casing, and the sliding door cap (as shown by 1901, 1903a, and 1963, respectively, in FIG. 19A) when the elements are connected or associated together. The locking channel (shown by 2185 in FIG. 21A) and the shape of the notches may be similar to a hook, such that a plurality of notched hooks 2287 may ensure that the casing 2203a can only be locked onto the base in one direction, when the casing is rotated on the base such that each notched hook is locked onto a locking magnet of a plurality of locking magnets. An advantage may be that the user can easily lock and unlock the elements of the compartmental dispenser from one another, such as when cleaning of the parts is needed. As an example, the casing 2203a may be constructed from dishwasher-safe materials, such that a user can easily remove residue from medications. To clean or perform maintenance on the compartmental dispenser 1960, the base 1901, the casing 1903a, and the sliding door cap 1963 may be separated from one another for ease of cleaning.

The top end of the casing 2203a may be provided with magnets 2269, which may be associated with the sliding door cap or any other type of cap. The bottom end of the casing 2203a may also be provided with magnets 2269. The bottom end of the casing 2203a may also be provided with a plurality of notches 2287 (not shown for visual clarity in FIG. 22C). A notch 2287 may be associated with a locking magnet (as shown and described by 2169a when referring to FIG. 21A), and may slide around the locking magnet and thus lock the casing 2203a onto the base, for example.

As an example, the casing 2203a may be open on the top end, and closed on the bottom end, such that the walls 2262 are visible in the top view of FIG. 22B, and not visible in the bottom view of FIG. 22C, and thus, the walls are represented by broken lines in FIG. 22C. It should be understood, however, that the casing 2203a may have opaque portions, or may be completely opaque, or may be completely transparent, and thus, the walls 2262 may be visible from the bottom view in some embodiments of the compartmental dispenser.

Figure 23A:
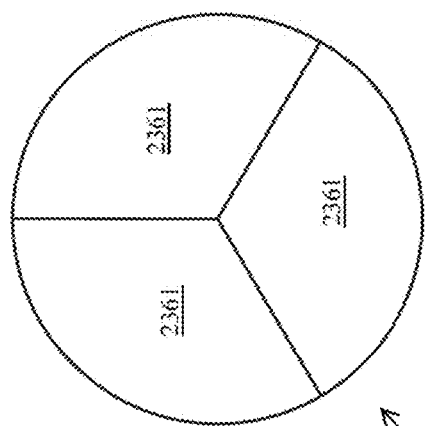
FIGS. 23A-23D illustrate top plan views of examples of the casing having a plurality of compartments 2361, according to an aspect.
Figure 23B:
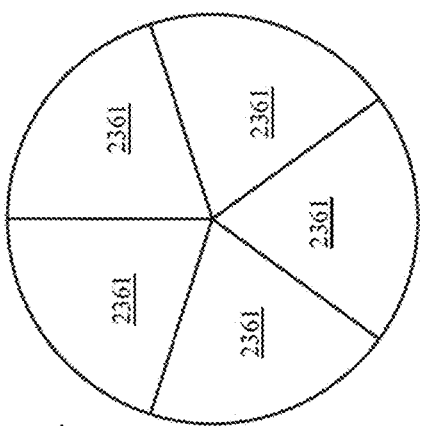
Figure 23C:
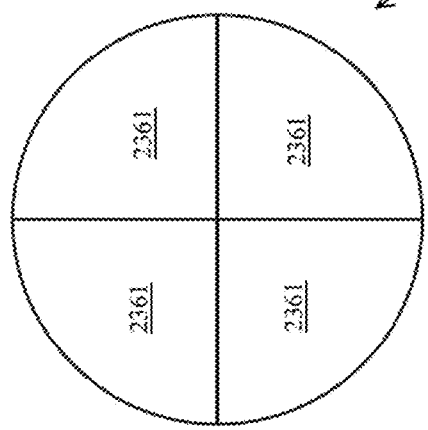
Figure 23D:
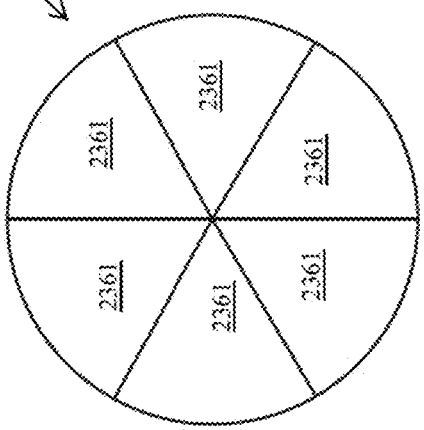

FIGS. 23A-23D illustrate top plan views of examples of the casing 2303a having a plurality of compartments 2361, according to an aspect. Again as previously described, a compartmental dispenser may be provided with any suitable number of compartments 2361. As shown as examples, a casing 2303a may have four compartments as shown in FIG. 23A, three compartments as shown in FIG. 23B, six compartments as shown in FIG. 23C, or five compartments as shown in FIG. 23D. It should be understood that a sliding door cap may be provided such that the sliding door is aligned properly with an individual compartment, for any given casing 2303a.

Figure 24A:
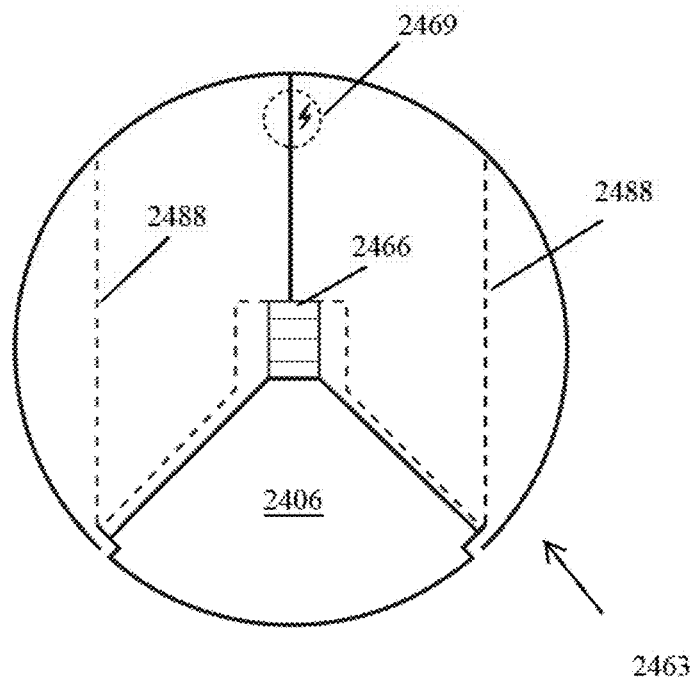
FIGS. 24A-24B illustrate top plan views of a sliding door cap in a closed state and in an open state, respectively, according to an aspect.
Figure 24B:
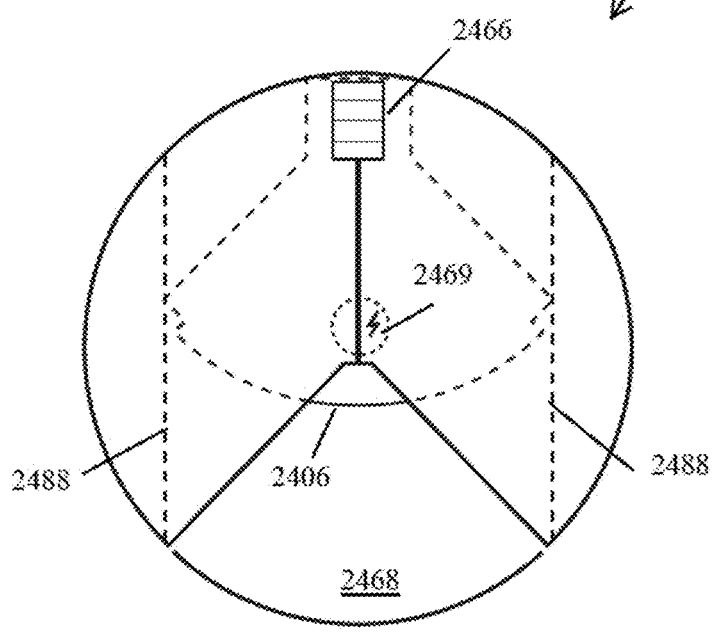
Figure 25A:
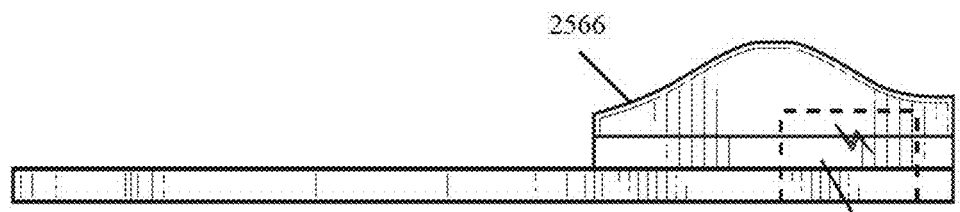
FIGS. 25A-25D illustrate the side elevation view, the front elevation view, the top plan view, and the bottom plan view, respectively, of the sliding door, according to an aspect.
Figure 25B:
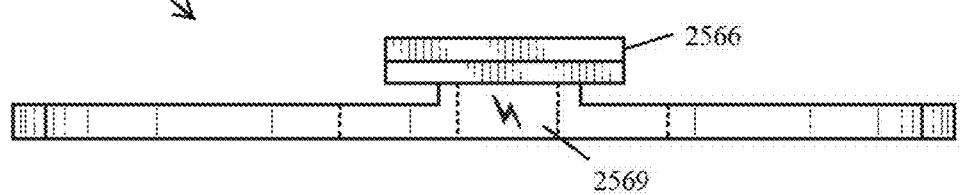
Figures 25C, 25D:
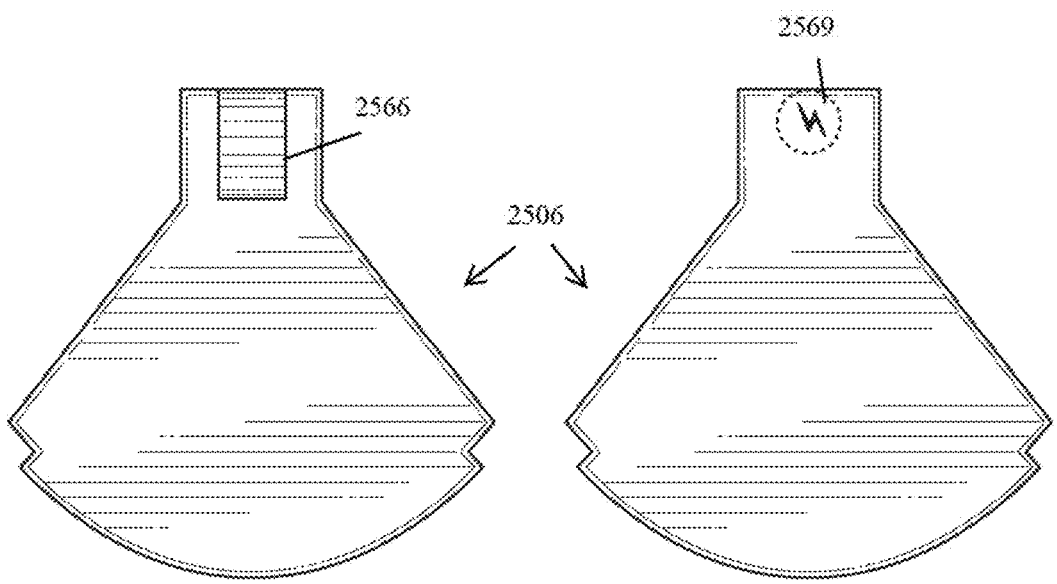

FIGS. 24A-24B illustrate top plan views of a sliding door cap 2463 in a closed state and in an open state, respectively, according to an aspect. The sliding door 2406 is shown fully extended outwards and thus closed in FIG. 24A. The sliding door 2406 may be closed by placing the slider 2466 into the center of the sliding door cap 2469. The sliding door 2406 may be opened by moving the sliding 2466 towards an edge of the sliding door cap 2463, thus, pulling the sliding door 2406 back underneath the remaining portions of the cap 2463. The sliding door 2406 is partially visible in FIG. 24B within the open space 2468, and the portions of the sliding door 2406 not visible under the cap are represented in broken lines.

FIGS. 25A-25D illustrate the side elevation view, the front elevation view, the top plan view, and the bottom plan view, respectively, of the sliding door 2506, according to an aspect. The movements of the sliding door 2506 during opening or closing may activate the magnets 2569 and complete an electrical connection, which may then signal to the memory and/or processor (as shown by 2183 in FIG. 21C) that the door has been opened or closed, such that the medication management platform may log or record data. Additionally, the magnets may also make electrical connections when the cap is rotated about the casing. Thus, the magnets may conduct a connection (which may indicate that a connection is made or not made, or "on" or "off"), and the system may be verify that the open section of the cap (as shown by 2068 in FIG. 20) is over the corresponding section that the medication is in, for which the alert was triggered. Next, the lights corresponding with the same section may light up. The magnets may connect to the magnets 2269 on either side of the corresponding section or compartment. The path along with the sliding door 2506 may travel during opening or closing is shown by broken lines 2488, which may represent guide tracks. The sliding door cap 2563 may be provided with a magnet 2569, or a plurality of magnets, which may interact with the wire (shown by 2262a in FIG. 22A) of the casing.

As shown, a magnet 2569 may be provided underneath the slider 2566 on the bottom side of the sliding door 2506. Thus, movements of the slider 2566 and thus the sliding door 2506 may cause associations with other magnets within the cap and may create electrical connections.

FIGS. 26A-26D illustrate the front elevation view, the right side elevation view, the bottom plan view, and the top plan view, respectively, of the sliding door cap 2663, shown without a slider for visual clarity, according to an aspect. As an example, two magnets, shown by a first cap magnet 2669b and a second cap magnet 2669c, may be provided in the sliding door cap 2663. The placement of the first magnet is represented by 2669b but may be obscured or may not be visible in the front elevation view of FIG. 26A. When the sliding door (shown by 2406 in FIGS. 24A-24B) is a closed position and next moved into an open position, the first magnet 2669b may move from the position 2669b-1 represented by broken lines in the direction indicated by arrow 2689, and next to the position shown by 2669b in FIG. 26B. In the open position, the first magnet 2669b may become aligned with the second magnet 2669c, create a magnetic connection and complete an electrical connection, and send a signal to the medication management platform, for example. Guide tracks 2688 along which the sliding door can move are also shown in FIG. 26D.

To use the compartmental dispenser shown and described when referring to FIGS. 19A-26D, the following exemplary process may be carried out. First, the user may confirm that a mobile application for accessing the medication management platform (as shown and described when referring to FIGS. 8A-12C) is installed on their mobile or electronic device, such as a smart phone or tablet. Next, the compartmental dispenser 1960 may be powered on, such as by pressing the power button 1917a. Next, the compartmental dispenser 1960 may be paired with or connected to the mobile or electronic device, such as through a Bluetooth connection. Bluetooth connections may, for example, be accessed through the mobile or electronic device, and the compartmental dispenser 1960 may be findable by the electronic device. The compartmental dispenser 1960 may provide an audio alert through the speaker 1964 and/or a visual alert via the lights 1937 when a successful Bluetooth pairing or connection has been made. Next, the user may make selections on the compartmental dispenser 1960 by using the left arrow 1917b or the right arrow 1917c to select a desired chamber (such as 1961a or 1961b). The sliding door cap 1963 may rotate when the user scrolls through the chamber selections using the left arrow 1917b or the right arrow 1917c. When a particular chamber is selected, the chamber may be highlighted via a portion of the lights 1937, which may be a group of lights such as the groups shown by 2137a-2137d. As an example, empty chambers may be signified by white lights, and filled chambers may be signified by other colors of lights. Next, to fill a currently empty chamber 1961, the user may select the chamber and press and hold the power button 1917a. The compartmental dispenser 1960 may show that the desired chamber has been successfully selected by blinking the lights 1937 associated with the selected chamber. Next, the mobile application for the medication management platform may automatically be launched on the user's mobile or electronic device. The mobile application may launch with a medication scan button available (an example of which is shown in FIG. 8A). Next, the user may scan or manually input their medication information from a prescription or medication bottle into the mobile application. Next, the chamber may be filled with medication by opening the sliding door situated above the highlighted or selected chamber 1961, by moving the slider 1966, and pouring in the medication. Next, the sliding door may be closed by again moving the slider 1966. Next, the user may again hold down the power button 1917a. The lights 1937 may turn off to signal to the user that the medicine filling step has been completed and accepted by the medication management platform system. The above steps and procedures may be repeated as needed in order to fill a desired number of chambers 1961 with a desired amount of medication needed by a user.

To use the compartmental dispenser, in connection with a medication management platform, to assist a user in consuming their medication, the following exemplary process may be carried out. First, when the medication management system determines that it is time for a user to consume medication, the compartmental dispenser 1960 may send an alert through either the lights 1937, the speaker 1964, the screen 1914, or any combination thereof. The screen 1914 may display the dosage and any other medication instructions. Next, the user's adherence to their prescription may be recorded and logged by the following actions. The rotation of the sliding door cap such that the sliding door is situated above a selected or desired chamber may be recorded. The opening of the sliding door cap may be recorded. The tilting of the compartmental dispenser for dispensing pills may be recorded by, for example, the measuring means 2186. As an example, a weighted pendulum may measure equilibrium and changes in equilibrium signaling that a user has tilted the dispenser. As an example, a change in weight within the dispenser may be recorded. Next, when the sliding door is closed and the compartmental dispenser is returned to an upright position, the compartmental dispenser may send an alert to the user (again, by the lights, the speaker, the screen, or any combination thereof) to indicate that adherence to the user's regimen or prescription was met. Alerts and notices may also be sent to the user via the mobile application, for example. The user may manually input whether they have consumed their medication or not.

As an example, the compartmental dispenser working together with the medication management platform may also send reminders to users, such as reminders to refill and pickup medications related to chronic illnesses such as diabetes, hypertension, cholesterol management, mental health, asthma, and diseases such as diabetes requiring treatment with statin. When a refill of medication is received by a user, the following exemplary process may be carried out. First, the user may verify a connection (such as via Bluetooth) between the compartmental dispenser and their electronic or mobile device. Next, the user may scan or manually input their medication information from a prescription or medication bottle into the mobile application. Next, if the medication management platform finds that the medication already exists within the user's profile, the platform may prompt the user to confirm whether the new scan is a refill of the exact medication that previously existed in the system. Next, if the user confirms "Yes" via the mobile application, the mobile application may automatically send a signal to the compartmental dispenser 1960 and highlight a compartment 1961 that housed the same medication using a blinking light or group of lights 1937.

To use the compartmental dispenser, in connection with a medication management platform, to assist a user in canceling their medication, adjusting a prescription, or canceling a prescription, the following exemplary process may be carried out. First, when a caregiver or doctor makes a change to a user's profile within the medication management platform, the user's mobile application may automatically update with the changes. The application may next prompt the compartmental dispenser to send an alert, which may be red flashing or blinking lights, for example. Next, the user may manually or automatically rotate the sliding door cap over a chamber highlighted by lights, which may be red lights, for example. The rotation may cause an electrical connection to be made via the magnets. Next, the sliding door may be opened to complete a second electrical connection. Next, the tilting of the compartmental dispenser for dispensing pills may be recorded by, for example, the measuring means 2186. As an example, a weighted pendulum may measure equilibrium and changes in equilibrium signaling that a user has tilted the dispenser. As an example, a change in weight within the dispenser may be recorded. Next, when the sliding door is closed and the compartmental dispenser is returned to an upright position, the compartmental dispenser may send an alert to the user (again, by the lights, the speaker, the screen, or any combination thereof) to indicate that a prescription was canceled or adjusted. Next, an alert may be sent to the user to confirm the change and that a canceled prescription no longer exists in their user profile.

It should be understood that while the focus in the disclosure is on the medication being prescription medication, the medication dispensing apparatus and medication management platform may be used for any other suitable pharmaceuticals, non-prescription or over-the-counter medication, vitamins, dietary supplements, and so on, and thus, any medication regimen that is prescribed or not prescribed may be used and tracked by the medication management system. It should also be understood that while the focus in the disclosure is on the medication being in pill form, the medication or other pharmaceuticals being used with the medication management system may be in a pill, capsule, or tablet form.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A medication management system, comprising a means for recording a medication regimen; and a medication dispenser capable of separately holding and dispensing medication comprising a first medication and a second medication, the medication dispenser having:
   a dispenser bottom end;
   a dispenser top end;
   a base having:
      a processor;

a control panel comprising buttons;
a screen;
a sensor adapted to detect changes in the medication dispenser; and
a plurality of light sets;
a casing having:
  an open top casing end;
  a bottom casing end adapted to be removably associated with the base;
  a plurality of compartments for storing the medication;
  a plurality of walls separating each compartment of the plurality of compartments, the plurality of walls extending between the open top casing end and the bottom casing end; and
  wires housed within the plurality of walls;
  wherein each compartment of the plurality of compartments has a shape and a set of dimensions at the open top casing end;
  wherein a first compartment of the plurality of compartments is adapted to hold and dispense the first medication; and
  wherein a second compartment of the plurality of compartments is adapted to hold and dispense the second medication;
a cap adapted to be removably associated with the open top casing end, the cap having:
  a door adapted to slide between a closed state and an open state;
  a slider at the dispenser top end capable of sliding the door between the closed state and the open state;
  a first cap magnet; and
  a second cap magnet adapted to be aligned with and make a magnetic connection with the first cap magnet when the door is in the open state, the magnetic connection creating a first electrical signal;
  wherein the cap is adapted to fit onto and rotate on the open top casing end;
  wherein the door has the shape and the set of dimensions such that the door is capable of being aligned with a compartment of the plurality of compartments via a rotation of the cap, such that the compartment of the plurality of compartments is accessible when the door is in the open state and the remaining compartments of the plurality of compartments is not accessible;
wherein the first electrical signal generated within the cap is sent to the processor via the wires;
wherein a first light set of the plurality of light sets corresponds to the first compartment of the plurality of compartments;
wherein a second light set of the plurality of light sets correspond to the second compartment of the plurality of compartments;
wherein the medication management system is adapted to send a first alert to the medication dispenser via the first light set when a user is scheduled within the medication regimen to take the first medication;
wherein the medication management system is adapted to send a second alert to the medication dispenser via the second light set when the user is scheduled within the medication regimen to take the second medication;
such that a removal of the first medication or the second medication from the medication dispenser is detected by the sensor and generates a second electrical signal; and
wherein the second electrical signal is sent to the processor.

2. The medication management system of claim 1, further comprising:
  a medication management platform accessible through an electronic device;
  a medication management platform database for storage of medication information related to a user; and
  means for the medication dispenser to have internet connectivity and wireless communication capability, such that:
    the medication regimen is sent to the medication dispenser via a wireless communication to be stored in the medication management platform database;
    the medication dispenser tracks adherence to the medication regimen to create a user record related to the user; and
    the user record is sent to the medication management platform database via the wireless communication, and wherein the user record becomes part of the medication information related to the user.

3. The medication management system of claim 2, wherein the electronic device is a mobile electronic device having an application for accessing the medication management platform.

4. The medication management system of claim 1, wherein the sensor comprises a tilt sensor, and the changes comprise variations in orientation of the medication dispenser.

5. The medication management system of claim 1, wherein the sensor comprises a scale, and the changes comprise a first weight and a second weight of contents of the plurality of compartments.

6. The medication management system of claim 1, the base further comprising a plurality of locking magnets;
  wherein the bottom casing end is adapted to make a locked connection with the base by having a plurality of notched hooks; and
  wherein the casing is rotated on the base to slide each notched hook of the plurality of notched hooks onto a locking magnet of the plurality of locking magnets.

7. The medication management system of claim 1, the base further comprising a port adapted to receive a power cable; and a speaker.

8. A medication management system, comprising a means for recording a medication regimen; and a medication dispenser capable of holding and dispensing medication, the medication dispenser having:
  a dispenser bottom end;
  a dispenser top end;
  a base having:
    a processor;
    a control panel;
    a screen; and
    a sensor adapted to detect changes in the medication dispenser;
  a casing having:
    an open top casing end;
    a bottom casing end adapted to be removably associated with the base;
    a plurality of compartments for storing the medication;
    a plurality of walls separating each compartment of the plurality of compartments, the plurality of walls extending between the open top casing end and the bottom casing end; and
    wires housed within the plurality of walls;
    wherein each compartment of the plurality of compartments has a shape and a set of dimensions at the open top casing end;

a cap having:
  a door adapted to be in a closed state and in an open state;
  a first cap magnet; and
  a second cap magnet adapted to be aligned with and make a magnetic connection with the first cap magnet when the door is in the open state, the magnetic connection creating a first electrical signal;
  wherein the cap is adapted to fit onto and rotate on the open casing end;
  wherein the door has the shape and the set of dimensions such that the door is capable of being aligned with a compartment of the plurality of compartments via a rotation of the cap, such that the compartment of the plurality of compartments is accessible when the door is in the open state and the remaining compartments of the plurality of compartments is not accessible;
wherein the first electrical signal generated within the cap is sent to the processor via the wires;
such that a removal of the medication from the medication dispenser is detected by the sensor and generates a second electrical signal; and
wherein the second electrical signal is sent to the processor.

9. The medication management system of claim 8, the base further comprising a plurality of light sets;
  wherein each light set of the plurality of light sets corresponds to a compartment of the plurality of compartments.

10. The medication management system of claim 8, the base further comprising a port adapted to receive a power cable; and a speaker.

11. The medication management system of claim 8, wherein the sensor comprises a tilt sensor, and the changes comprise variations in orientation of the medication dispenser.

12. A method of medication management using:
  a means for recording a medication regimen;
  a medication management platform accessible through an electronic device;
  and a medication dispenser capable of holding and dispensing medication, the medication dispenser having:
  a dispenser bottom end;
  a dispenser top end;
  a base having:
    a processor;
    a control panel;
    a screen; and
    a sensor adapted to detect changes in the medication dispenser;
  a casing having:
    an open top casing end;
    a bottom casing end adapted to be removably associated with the base;
    a plurality of compartments for storing the medication;
    a plurality of walls separating each compartment of the plurality of compartments, the plurality of walls extending between the open top casing end and the bottom casing end; and
    wires housed within the plurality of walls;
    wherein each compartment of the plurality of compartments has a shape and a set of dimensions at the open top casing end;
  a cap having:
    a door adapted to be in a closed state and in an open state;
    a first cap magnet; and
    a second cap magnet adapted to be aligned with and make a magnetic connection with the first cap magnet when the door is in the open state, the magnetic connection creating a first electrical signal;
    wherein the cap is adapted to fit onto and rotate on the open casing end;
    wherein the door has the shape and the set of dimensions such that the door is capable of being aligned with a compartment of the plurality of compartments via a rotation of the cap, such that the compartment of the plurality of compartments is accessible when the door is in the open state and the remaining compartments of the plurality of compartments is not accessible;
  wherein the first electrical signal generated within the cap is sent to the processor via the wires;
  wherein the medication management system is adapted to send an alert to the medication dispenser when a user is scheduled within the medication regimen to take the medication;
  such that a removal of the medication from the medication dispenser is detected by the sensor and generates a second electrical signal; and
  wherein the second electrical signal is sent to the processor;
the method comprising the steps of:
  receiving a set of instructions related to the medication regimen;
  accessing the medication management platform through the electronic device;
  importing the medication regimen into a user record stored within a medication management platform database, via the means for recording a medication regimen;
  sending the medication regimen to the medication dispenser;
  selection of a first compartment of the plurality of compartments;
  filling the first compartment of the plurality of compartments with the medication;
  notifying the user with the alert when the user is scheduled within the medication regimen to take the medication; and
  responding to the alert by dispensing the medication from the medication dispenser.

13. The method of claim 12, wherein the filling step is recorded within the medication management platform.

14. The method of claim 12, wherein the sensor comprises a tilt sensor, and the changes comprise variations in orientation of the medication dispenser.

15. The method of claim 14, wherein the responding step comprises tilting the medication dispenser from a first position to a second position to dispense the medication, and returning the medication dispenser to the first position.

16. The method of claim 12, wherein the selection step is performed via the control panel;
  and the method further comprising the step of:
    confirmation of the selection of the first compartment of the plurality of compartments.

17. The method of claim 12, further comprising the steps of:
  recording the dispensing of the pill;
  tracking activity of the user to generate a tracked activity record; and
  sending the tracked activity record to the medication management platform database;

wherein the tracked activity record becomes part of the user record.

18. The method of claim 12, wherein a second user having credentials for prescribing medication has access to the medication management platform to make changes to the medication regimen.

19. The method of claim 12, the base further comprising a port adapted to receive a power cable; and a speaker; and
   the notifying step comprising a noise from the speaker.

20. The method of claim 12, the base further comprising a plurality of light sets;
   wherein each light set of the plurality of light sets corresponds to a compartment of the plurality of compartments; and
   the notifying step comprising a flashing light from a light set of the plurality of light sets.

* * * * *